United States Patent [19]
Preuss et al.

[11] Patent Number: 5,859,020
[45] Date of Patent: Jan. 12, 1999

[54] SUBSTITUTED 4-ALKOXYPYRIMIDINES, PROCESS FOR THEIR PREPARATION, AGENTS CONTAINING THEM, AND THEIR USE AS PESTICIDES

[75] Inventors: Rainer Preuss, Hofheim; Gerhard Salbeck, deceased, late of Kriftel, by Gisela Salbeck, executor; Wolfgang Schaper, Diedorf; Peter Braun, Nieder-Olm; Werner Knauf, Eppstein; Burkhard Sachse, Kelkheim; Anna Waltersdorfer, Frankfurt/Main; Manfred Kern, Lörzweiler; Peter Lümmen, Niedernhausen, all of Germany

[73] Assignee: Hoechst Schering AgrEvo GmbH, Berlin, Germany

[21] Appl. No.: 783,072

[22] Filed: Jan. 15, 1997

Related U.S. Application Data

[63] Continuation of Ser. No. 211,156, filed as PCT/EP92/02181 Sep. 21, 1992.

[30] Foreign Application Priority Data

Sep. 25, 1991 [DE] Germany .......... 41 31 924.9

[51] Int. Cl.⁶ .......... A61K 31/505; C07D 239/52
[52] U.S. Cl. .......... 514/269; 514/259; 514/274; 544/243; 544/253; 544/287; 544/319; 544/321
[58] Field of Search .......... 514/259, 269, 514/274; 544/243, 253, 287, 319, 321

[56] References Cited

U.S. PATENT DOCUMENTS

| | | | |
|---|---|---|---|
| 4,751,225 | 6/1988 | Nishida et al. | 514/277 |
| 4,849,424 | 7/1989 | Ikeda et al. | 514/256 |
| 4,879,292 | 11/1989 | Nishida et al. | 514/241 |
| 4,970,222 | 11/1990 | Nishida et al. | 514/369 |

FOREIGN PATENT DOCUMENTS

| | | |
|---|---|---|
| 0257850 | 3/1988 | European Pat. Off. . |
| 0326329 | 8/1989 | European Pat. Off. . |
| 0331529 | 9/1989 | European Pat. Off. . |
| 0534341 | 3/1993 | European Pat. Off. ......... 544/319 |
| 2360581 | 3/1978 | France . |
| 2140010 | 11/1984 | United Kingdom . |
| 9319050 | 9/1993 | WIPO ......... 544/319 |

OTHER PUBLICATIONS

Chemical Abstracts, vol. 106, 1987, pp. 668–669.
Chemical Abstracts, vol. 105, 1986, p. 724.
Journal of the Chemical Society, Perkin Trans. I. 1987, (London, GB), T.R. Jones, et al., "An azafluorenes containing two bridgehead nitrogen atoms" pp. 2585–2592.
Chemical and Pharmaceutical Bulletin, vol. 27, No. 6, 1979, (Tokyo, JP), H. Asakawa et al., "Chemistry of salicylic acid and anthranilic acid. III. Hypoglycemic screening tests or salicylic and anthranilic acid derivatives", pp. 1468–1472.

*Primary Examiner*—Yogendra N. Gupta
*Attorney, Agent, or Firm*—Frommer Lawrence & Haug LLP

[57] ABSTRACT

The invention relates to substituted 4-alkoxypyrimidines of the formula

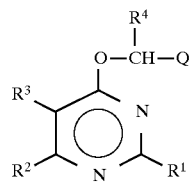

in which $R^1$ is hydrogen, halogen, alkyl or cycloalkyl, $R^2$ is hydrogen, optionally substituted alkyl, optionally substituted alkoxy, optionally substituted alkylthio, alkylamino or dialkylamino, $R^3$ is hydrogen, alkyl, alkoxy, haloalkoxy, halogen, alkylthio, amino, alkylamino or dialkylamino, and $R^4$ is hydrogen, alkyl, cycloalkyl or haloalkyl, where $R^2$ and $R^3$ together with the carbon atoms to which they are attached can also form a ring, and Q is as defined in the description.

The invention furthermore relates to a process for their preparation, to agents containing them, and to their use as pesticides.

14 Claims, No Drawings

SUBSTITUTED 4-ALKOXYPYRIMIDINES, PROCESS FOR THEIR PREPARATION, AGENTS CONTAINING THEM, AND THEIR USE AS PESTICIDES

This application is a continuation of application Ser. No. 08/211,156, filed as PCT/EP92/02181 Sep. 21, 1992, now abandoned.

The invention relates to novel substituted 4-alkoxypyrimidines, to a process for their preparation, and to their use as pesticides, in particular as insecticide, acaricide, nematocide and fungicide.

It has already been disclosed that certain substituted 4-alkoxyquinazolines have a good fungicidal, acaricidal and insecticidal action (cf. EP 326,328, EP 326,329). However, the biological action of these compounds is not satisfactory in all fields of application, in particular when low amounts and low concentrations are applied.

The invention relates to substituted 4-alkoxypyrimidines of the formula I

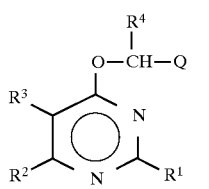
(I)

in which

- $R^1$ is hydrogen, halogen, $(C_1-C_4)$alkyl or $(C_3-C_6)$cycloalkyl,
- $R^2$ is hydrogen, $(C_1-C_4)$alkyl, halogen, $(C_1-C_4)$haloalkyl, $(C_1-C_{10})$alkoxy, phenyl-$(C_1-C_4)$alkoxy, $(C_1-C_{10})$alkoxy-$(C_1-C_{10})$alkoxy, benzyloxy-$(C_1-C_{10})$alkoxy, $(C_1-C_{10})$haloalkoxy, $(C_1-c_{10})$alkoxy-$(C_1-C_{10})$alkyl, $(C_1-C_{10})$alkylthio, $(C_1-C_{10})$alkylthio-$(C_1-C_{10})$alkyl, $(C_1-C_{10})$alkylamino or di-$(C_1-C_{10})$alkylamino, where phenyl in the abovementioned radicals is optionally monosubstituted by $(C_1-C_6)$alkyl, $(C_1-C_6)$alkoxy or halogen,
- $R^3$ is hydrogen, $(C_1-C_4)$alkyl, $(C_1-C_4)$alkoxy, $(C_1-C_4)$haloalkyl, halogen, $(C_1-C_4)$alkylthio, amino, $(C_1-C_4)$alkylamino, $(C_1-C_4)$dialkylamino or
- $R^2$ and $R^3$ together with the carbon atom to which they are bonded form an unsaturated 5-membered ring which contains an oxygen or sulfur atom and is optionally substituted by alkyl or halogen, or
- $R^2$ and $R^3$ together with the carbon atom to which they are bonded form a saturated 5-, 6- or 7-membered ring which can contain an oxygen or sulfur atom and which is optionally substituted by alkyl,
- $R^4$ is hydrogen, $(C_1-C_4)$alkyl, $(C_3-C_6)$cycloalkyl or $(C_1-C_4)$haloalkyl such as $CF_3$,
- Q has the meaning of $Q^1$ and
- $Q^1$ is $(C_1-C_{15})$alkyl which can be up to triunsaturated and which is optionally substituted by one, two or three halogen atoms, a $(C_3-C_8)$cycloalkyl group, a $(C_1-C_{15})$alkoxy group, a $(C_1-C_{15})$alkoxy-$(C_1-C_{15})$alkoxy group, a $(C_3-C_{15})$alkylthio group, a $(C_1-C_{15})$alkylsulfinyl group, a $(C_1-C_{15})$alkylsulfonyl group, a $(C_1-C_{15})$alkanoyl group, a $(C_4-C_8)$cycloalkylalkoxy group, a $(C_4-C_8)$cycloalkylalkylthio group, a benzyloxy or a phenoxybenzyloxy group, or
- Q has the meaning of $Q^2$ and $Q^2$ is a group of the formula IIa–IIj

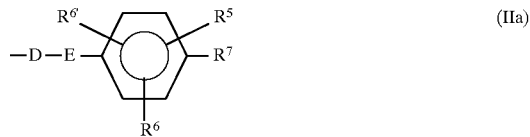
(IIa)

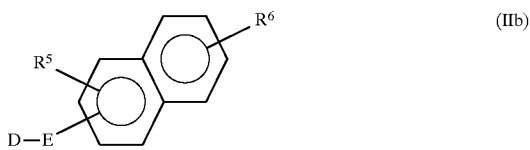
(IIb)

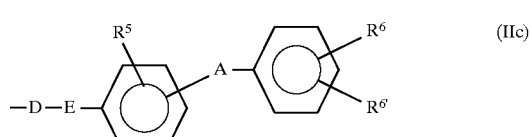
(IIc)

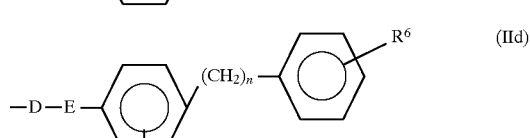
(IId)

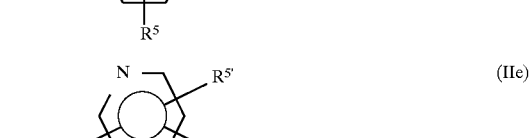
(IIe)

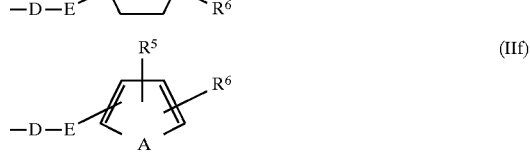
(IIf)

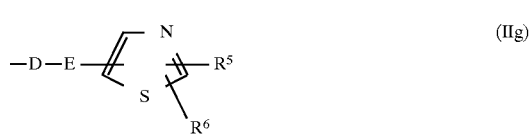
(IIg)

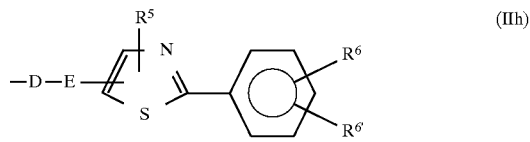
(IIh)

(IIi)

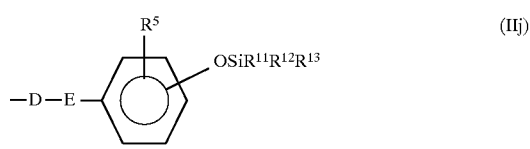
(IIj)

in which n is 0, 1 or 2,
A is oxygen, —O—$CH_2$—, sulfur, sulfinyl or sulfonyl,
A' is oxygen or sulfur,
D is a direct bond or a $(C_1-C_6)$alkylene group,
E is a direct bond and, in the event that D is an alkylene group, is oxygen or imino,
$R^5$, $R^6$ and $R^{6'}$ are identical or different and are in each case hydrogen, halogen, $(C_1-C_8)$alkyl, $(C_2-C_8)$alkenyl, ($C_2$–$C_8$)alkynyl, ($C_3$–$C_6$)cycloalkyl, ($C_1$–$C_8$)haloalkyl, ($C_1$–$C_8$)alkoxy, ($C_1$–$C_8$)alkylthio, ($C_1$–$C_8$)alkylsulfinyl, ($C_1$–$C_8$)alkylsulfonyl, ($C_1$–$C_4$)dialkylamino or nitro, where, in the event that $R^5$, $R^6$ and $R^{6'}$ are alkyl radicals, it is also possible for these to be linked in the form of a cycle, $R^7$ is as defined for $R^5$, $R^6$ and $R^6$ and, in the event that E is a direct bond, is also ($C_1$–$C_4$)alkoxy-($C_1$–$C_4$)alkyl, ($C_1$–$C_4$)alkoxycarbonyl, ($C_1$–$C_8$)alkanoyl or a group of the formula III

in which X and Y are identical or different and are in each case sulfur or oxygen and $R^8$ is hydrogen or ($C_1$–$C_4$)alkyl, or Q has the meaning of $Q^3$ and $Q^3$, if not embraced by the above formula IId, is a group of the formula IV

in which $R^5$ and $R^6$ have the abovementioned meanings,

U is a direct bond, oxygen, sulfur, sulfinyl, sulfonyl or methylene, $R^9$ is phenyl or a heterocyclic radical, where each of the two abovementioned radicals can be unsubstituted or provided with one or two substituents and these substituents are identical or different and are in each case halogen, ($C_1$–$C_4$)alkyl, trifluoromethyl, nitro, ($C_1$–$C_4$)alkoxy, ($C_1$–$C_4$)alkylthio, ($C_1$–$C_4$)alkylsulfinyl, ($C_1$–$C_4$)alkylsulfonyl, ($C_1$–$C_4$)alkoxy-($C_1$–$C_4$)alkyl, phenyl, phenoxy, ($C_1$–$C_4$)alkoxyphenoxy, halophenoxy or ($C_1$–$C_4$)alkylphenoxy, $R^9$, in the event that U is oxygen, is furthermore ($C_1$–$C_4$)haloalkyl or a group of the formula V

in which
W is nitrogen or a group $CR^{10}$ in which
$R^{10}$ is hydrogen, fluorine, cyano, formyl, acetyl nitro, methyl, methoxy or 1,3-dioxolan-2-yl,
$R^{11}$, $R^{12}$ and $R^{13}$ are identical or different and are ($C_1$–$C_{15}$)alkyl which is optionally monosubstituted or polysubstituted by halogen, or is

or

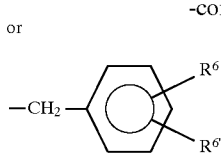

in which $R^6$ and $R^{6'}$ are as defined above.

Preferred compounds of the formula I are those in which
$R^1$ is hydrogen, chlorine or methyl,
$R^2$ is ($C_1$–$C_4$)alkyl, chlorine, trifluoromethyl, methoxy, ethoxy or methoxymethyl,
$R^3$ is hydrogen, ($C_1$–$C_3$)alkyl, methoxy, ethoxy or halogen, or
$R^2$ and $R^3$ together with the carbon atom to which they are bonded form an unsaturated 5-membered ring which contains an oxygen or sulfur atom, or $R^2$ and $R^3$ together with the carbon atom to which they are bonded form a saturated 5- or 6-membered ring which can contain a sulfur atom,
$R^4$ is hydrogen, methyl, ethyl, trifluoromethyl or cyclopropyl, and
Q has the meaning of $Q^1$, $Q^2$ or $Q^3$.

More preferred compounds of the formula I are those in which
$R^1$ is hydrogen or methyl,
$R^2$ is methyl, ethyl, trifluoromethyl, methoxy, ethoxy or methoxymethyl,
$R^3$ is methyl, ethyl, methoxy, chlorine or bromine, or
$R^2$ and $R^3$ together with the carbon atom to which they are bonded form a saturated 5- or 6-membered ring,
$R^4$ is hydrogen, methyl, ethyl, trifluoromethyl or cyclopropyl, and
Q has the meaning of $Q^1$, $Q^2$ or $Q^3$.

Even more preferred compounds of the formula I are those in which
$R^1$ is hydrogen,
$R^2$ is methyl, ethyl or methoxymethyl,
$R^3$ is chlorine, bromine or methoxy, or
$R^2$ and $R^3$ together with the carbon atom to which they are bonded form a saturated 6-membered ring,
$R^4$ is hydrogen, methyl or ethyl, and
Q has the meaning of $Q^1$, $Q^2$ or $Q^3$.

Very particularly preferred compounds of the formula I are those in which
$R^1$ is hydrogen,
$R^2$ is methoxymethyl and $R^3$ is methoxy, or
$R^2$ is methyl or ethyl and $R^3$ is chlorine or bromine, or
$R^2$ and $R^3$ together with the carbon atom to which they are bonded form a saturated 6-membered ring,
$R^4$ is hydrogen, methyl or ethyl, and
Q has the meaning of $Q^1$, $Q^2$ or $Q^3$.

Most preferred compounds of the formula I are those in which
$R^1$ is hydrogen,
$R^2$ is methoxymethyl and $R^3$ is methoxy, or
$R^2$ is ethyl and $R^3$ is chlorine, or
$R^2$ and $R^3$ together with the carbon atom to which they are bonded form a saturated 6-membered ring,
$R^4$ is hydrogen or methyl,
$Q^1$ is a ($C_4$–$C_{10}$)alkyl group or a ($C_1$–$C_3$)alkyl group which is substituted by a cyclohexyl group, ($C_4$–$C_8$)

cycloalkylalkoxy group or a $(C_4-C_8)$ cycloalkylalkylthio group.

Other most preferred compounds of the formula I are those in which
$R^1$ is hydrogen,
$R^2$ is methoxymethyl and $R^3$ is methoxy, or
$R^2$ is ethyl and $R^3$ is chlorine, or
$R^2$ and $R^3$ together with the carbon atom to which they are bonded form a saturated 6-membered ring,
$R^4$ is hydrogen or methyl,
$Q^2$ is a group of the formulae IIa–IIj, preferably IIa, IIb, IIc, IId, IIf, IIi, IIj, in particular IIa, IIi, IIj, in which D is a methylene group and E is a direct bond, $R^5$, $R^6$ and $R^{6'}$ are hydrogen, $(C_1-C_8)$alkyl, $(C_1-C_4)$alkoxy, cyclohexyl or trifluoromethyl, and
$R^7$ is methoxyethyl or ethoxyethyl.

Other most preferred compounds of the formula I are those in which
$R^1$ is hydrogen,
$R^2$ is methoxymethyl and $R^3$ is methoxy, or
$R^2$ is ethyl and $R^3$ is chlorine, or
$R^2$ and $R^3$ together with the carbon atom to which they are bonded form a saturated 5- or 6-membered ring,
$R^4$ is methyl, ethyl or cyclopropyl,
Q has the meaning of $Q^3$,
$R^5$ and $R^6$ are hydrogen,
U is oxygen,
$R^9$ is phenyl or a heterocycle, where each of the two abovementioned radicals can be unsubstituted or provided with one or two substituents and these substituents are identical or different and are in each case halogen, $(C_1-C_4)$alkyl, trifluoromethyl, nitro, $(C_1-C_4)$alkoxy, $(C_1-C_4)$alkylthio or $(C_1-C_4)$alkoxy-$(C_1-C_4)$alkyl.

In the above formula I, "halogen" is understood as meaning a fluorine, chlorine, bromine or iodine atom, preferably a chlorine or bromine atom, the term "$(C_1-C_4)$alkyl" is understood as meaning an unbranched or branched hydrocarbon radical having 1–4 carbon atoms such as, for example, the methyl, ethyl, propyl, 1-methylethyl, 2-methylpropyl or 1,1-dimethylethyl radical, the term "$(C_1-C_8)$alkyl" is understood as meaning the abovementioned alkyl radicals as well as, for example, the pentyl, 2-methylbutyl or the 2,2-dimethylpropyl radical, or the hexyl, heptyl or octyl radical.

The term "$(C_1-C_{15})$" is understood as meaning a branched or unbranched hydrocarbon radical having 1–15 carbon atoms such as, for example, the radicals mentioned above under "$(C_1-C_4)$alkyl" or the pentyl, hexyl, heptyl, octyl, 1-nonyl, 2-nonyl, 1-decyl, 2-decyl, 1-undecyl, 2-undecyl, dodecyl, tridecyl, the tetradecyl or the pentadecyl radical, the term "$(C_3-C_6)$cycloalkyl" is understood as meaning the cyclopropyl, cyclobutyl, cyclopentyl or cyclohexyl group, the term "$(C_1-C_4)$alkoxy" is understood as meaning an alkoxy group whose hydrocarbon radical has the meaning mentioned in the case of the term "$(C_1-C_4)$alkyl", the term "$(C_1-C_{15})$alkoxy" is understood as meaning an alkoxy group whose alkyl groups have the meaning mentioned above in the case of "$(C_1-C_{15})$alkyl", the term "$(C_1-C_4)$alkylthio" is understood as meaning an alkylthio group whose hydrocarbon radical has the meaning given in the case of the term "$(C_1-C_4)$alkyl", the term "$(C_1-C_{15})$alkylthio" is understood as meaning an alkylthio group whose hydrocarbon radical has the meaning given in the case of the term "$(C_1-C_{15})$alkyl", the term "$(C_1-C_4)$alkoxycarbonyl" is understood as meaning a carboxylic ester group whose alkoxy moiety has the meaning given in the case of the term "$(C_1-C_4)$alkoxy", the term "$(C_1-C_4)$haloalkyl" is understood as meaning an alkyl group mentioned in the case of the term "$(C_1-C_4)$alkyl" in which one or more hydrogen atoms are replaced by the abovementioned halogen atoms, preferably chlorine or fluorine, such as, for example, the trifluoromethyl group, the 2,2,2-trifluoroethyl group, the chloromethyl or the fluoromethyl group, the term "$(C_1-C_4)$haloalkoxy" is understood as meaning a haloalkoxy group whose halohydrocarbon radical has the meaning given in the case of the term "$(C_1-C_4)$haloalkyl", the term "$(_1-C_4)$alkoxy-$(C_1-C_4)$alkyl" is understood as meaning, for example, a 1-methoxyethyl group, a 2-methoxyethyl group, a 2-ethoxyethyl group, a methoxymethyl or ethoxymethyl group, a 3-methoxypropyl group or a 4-butoxybutyl group, the term "$(C_1-C_4)$alkylthio-$(C_1-C_4)$alkyl" is understood as meaning, for example, methylthiomethyl, ethylthiomethyl, propylthiomethyl, 2-methylthioethyl, 2-ethylthioethyl or 3-methylthiopropyl, the term "$(C_1-C_4)$alkylamino" is understood as meaning an alkylamino group whose hydrocarbon radical has the meaning given in the case of the term "$(C_1-C_4)$alkyl", preferably the ethylamino and methylamino group, the term "$(C_1-C_4)$dialkylamino" is understood as meaning a dialkylamino group whose hydrocarbon radicals are as defined in the case of the term "$(C_1-C_4)$alkyl", preferably the dimethylamino and diethylamino group, the term "$(C_1-C_6)$alkylsulfinyl" is understood as meaning an alkylsulfinyl group whose hydrocarbon radical is as defined in the case of the term "$(C_1-C_{15})$alkyl", the term "$(C_1-C_{15})$alkylsulfonyl" is understood as meaning an alkylsulfonyl group whose hydrocarbon radical is as defined in the case of the term "$(C_1-C_{15})$alkyl", the term "$(C_4-C_8)$cycloalkylalkoxy" is understood as meaning, for example, the cyclopropylmethoxy group, the cyclopropylethoxy group, the cyclobutylmethoxy group, the cyclopentylmethoxy group, the cyclohexylmethoxy group or the cyclohexylethoxy group, the term "$(C_4-C_8)$cycloalkylalkylthio" is understood as meaning, for example, the cyclopropylmethylthio group, the cyclopropylethylthio group, the cyclobutylmethylthio group, the cyclopentylmethylthio group, the cyclohexylmethylthio group or the cyclohexylethylthio group, the term "$(C_1-C_6)$alkyene" is understood as meaning a straight-chain or branched alkylene chain having 1–6 carbon atoms such as, for example, the methylene group, the ethylene group, the trimethylene group, the tetramethylene group, —CH(CH$_3$)—,

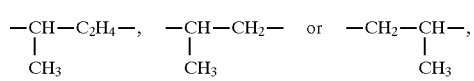

and the term "$(C_1-C_8)$alkanoyl" is understood as meaning a straight-chain or branched alkanoyl group having 1–8 carbon atoms such as, for example, the formyl group, the acetyl group, the propionyl group, the 2-methylpropionyl group, the butyryl group, the pivaloyl group, or the pentanoyl, hexanoyl, heptanoyl or octanoyl group.

A "heterocyclic radical" is preferably a heteroaryl radical having up to 10 carbon atoms or a partially, or temporarily, saturated radical derived therefrom. A "heteroaryl radical" having up to 10 carbon atoms is preferably understood as meaning a mono-, bi- or tricyclic($C_6$–$C_{14}$)aryl radical such as phenyl, naphthyl or anthryl, in which at least one CH is replaced by N and/or where at least two adjacent CH groups are replaced by one NH, O and/or S. Examples of such radicals are thienyl, benzothienyl, furyl, benzofuryl, pyrrolyl, imidazolyl, pyryzolyl, pyridyl, pyrazinyl, pyrimidinyl, pyridazinyl, indolyl, oxazolyl, isoxazolyl, thiazolyl, isothiazolyl, benzoxazolyl, benzothiazolyl, indalizonyl, isoindolyl, indazolyl, quinolizinyl, quinolyl, isoquinolyl, phthalazonyl, quinoxalonyl, quinazolinyl, cinnolinyl, carbozolyl, acridinyl, phenazinyl, phenoxazinyl, phenthiazinyl and tetrazolyl.

The same applies to groups which are not listed individually here and whose carbon number deviates from the abovementioned groups or which are derived from these.

The explanation given above applies analogously to homologues.

The present invention relates to the compounds of the formula I in the form of the free base or of an acid addition salt. Acids which can be used for salt formation are inorganic acids such as hydrochloric acid, hydrobromic acid, nitric acid, sulfuric acid, phosphoric acid, or organic acids such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

In some cases, the compounds of the formula I have one or more asymmetric carbon atoms. Racemates and diastereomers can therefore exist. The invention embraces the pure isomers as well as the mixtures thereof. The diastereomer mixtures can be separated into the components by customary methods, for example by selective crystallization from suitable solvents or by chromatography. Racemates can be resolved into the enantiomers by customary methods, for example by salt formation with an optically active acid, separation of the diastereomeric salts and liberation of the pure enantiomers by means of a base.

The invention furthermore relates to a process for the preparation of compounds of the formula I which comprises reacting a compound of the formula VI

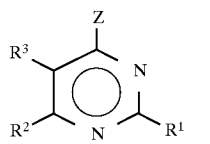
(VI)

in which $R^1$, $R^2$ and $R^3$ are as defined in formula I and Z is a leaving group, for example halogen, alkylthio, alkanesulfonyloxy or arylsulfonyloxy, alkylsulfonyl or arylsulfonyl, with an alcohol of the formula VII

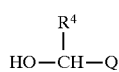
(VII)

in which $R^4$ and Q are as defined in formula I, and, if appropriate, oxidizing the resulting compounds of the formula I on the sulfur of a thioether side chain or chlorinating or brominating these compounds on the $C_5$ atom of the pyrimidine, and, if appropriate, converting the resulting compounds into their salts.

The above-described substitution reaction is known in principle. The leaving group Z can be varied within wide ranges and can be, for example, a halogen atom such as fluorine, chlorine, bromine or iodine, or alkylthio such as methylthio or ethylthio, or alkanesulfonyloxy such as methane-, trifluoromethane- or ethanesulfonyloxy, or arylsulfonyloxy such as benzenesulfonyloxy or toluenesulfonyloxy, or alkylsulfonyl such as methylsulfonyl or ethylsulfonyl, or arylsulfonyl such as phenylsulfonyl or toluenesulfonyl.

The abovementioned reaction is carried out in a temperature range of from 20°–150° C., expediently in the presence of a base and, if appropriate, in an inert organic solvent such as N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the abovementioned solvents can also be used.

Examples of suitable bases are carbonates, hydrogen carbonates, amides or hydrides of alkali metals or alkaline earth metals such as sodium carbonate, sodium hydrogen carbonate, potassium carbonate, sodium amide or sodium hydride, or organolithium compounds such as n-butyllithium.

The invention furthermore relates to a process for the preparation of the compounds of the formula I'

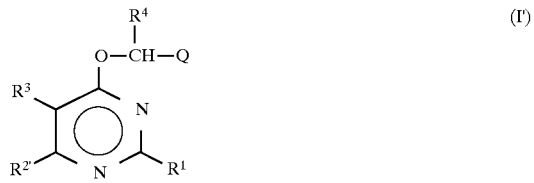
(I')

in which $R^1$, $R^3$, $R^4$ and Q are as defined in formula I and $R^{2'}$ is ($C_1$–$C_{10}$)alkoxy, ($C_1$–$C_{10}$)haloalkoxy, ($C_1$–$C_{10}$)alkylthio, ($C_1$–$C_{10}$)alkylamino or ($C_1$–$C_{10}$)dialkylamino, which comprises reacting a compound of the formula VIII

(VIII)

in which Z and Z' can be identical or different and are a leaving group, for example halogen, alkylthio, alkanesulfonyloxy, arylsulfonyloxy, alkylsulfonyl or arylsulfonyl and $R^1$ and $R^3$ are as defined in formula I', with a compound of the formula VII

(VII)

in which $R^4$ and Q are as defined in formula I', to give a compound of the formula IX

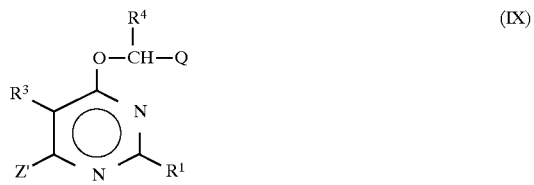
(IX)

in which $R^1$, $R^3$, $R^4$, Q and Z have the abovementioned meanings, and, in a second reaction step, reacting the compound of the formula VIII with a compound of the formula X

HR²' (X)

in which R²' has the abovementioned meaning, and, if appropriate, oxidizing the resulting compound of the formula I' on the sulfur of a thioether side chain or, if appropriate, in the event that R³ is hydrogen, chlorinating or brominating the compound, and, if appropriate, converting the resulting compounds into their salts.

To prepare the compounds of the formula I', a procedure is followed in which the compounds VI are reacted with the compounds VII, completely analogously to the above-described preparation of the compounds of the formula I.

The leaving group Z', which is required in the second reaction step, is defined like the abovementioned leaving group Z. As regards the reaction conditions, the same solvents, auxiliary bases and reaction temperatures can be used in the second reaction step as in the abovedescribed preparation of the compounds of the formula I from the compounds of the formulae VI and VII. Both reaction steps can be carried out as a one-pot reaction with working-up after the first reaction stage.

The invention furthermore relates to a process for the preparation of compounds of the formula I', which comprises reacting a compound of the abovementioned formula VIII with a compound of the formula X to give a compound of the formula XI

(XI)

in which R¹ and R³ are as defined in formula I', R² is ($C_1$–$C_4$)alkoxy, ($C_1$–$C_4$)haloalkoxy, ($C_1$–$C_4$)alkylthio, ($C_1$–$C_4$)alkylamino or ($C_1$–$C_4$)dialkylamino and Z is as defined in formula VI, reacting the compound of the formula XI with an alcohol of the formula VII, and, if appropriate, oxidizing the resulting compound of the formula I' on the sulfur of a thioether side chain or, in the event that R³ is hydrogen, chlorinating or brominating the compound.

As regards the reaction conditions, the same solvents, auxiliary bases and reaction temperatures can be used for both reaction steps as in the above-described preparation of the compounds of the formula I from the compounds of the formulae VI and VII.

Alternatively, both reaction steps can be carried out as a one-pot reaction, without working-up after the first reaction stage.

The starting compounds of the formula VI can be prepared analogously to known processes. The starting materials used are acetacetate derivatives which are converted into the halopyrimidines via the corresponding hydroxypyrimidines:

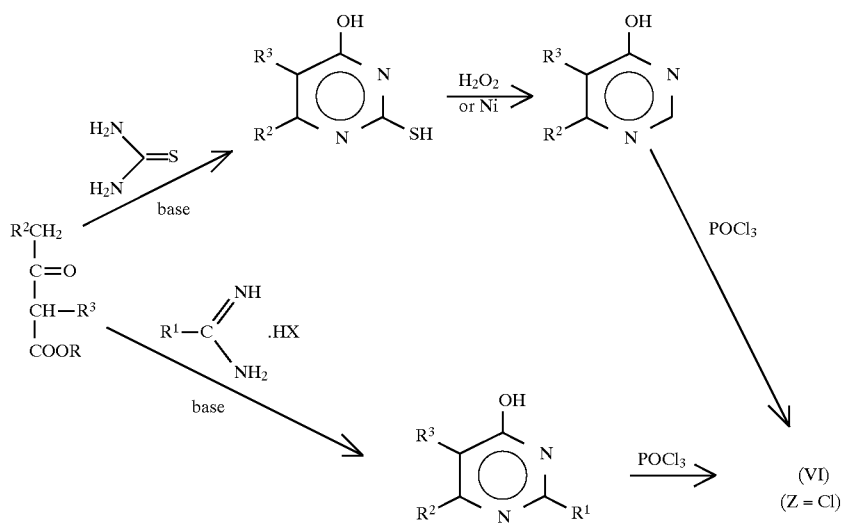

The starting compounds of the formula VII can be obtained from malonate derivatives analogously to known processes:

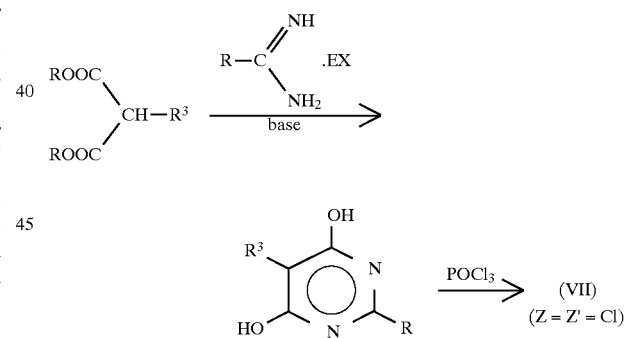

The alcohols of the formula VII, which are required as starting materials, can be prepared by known processes.

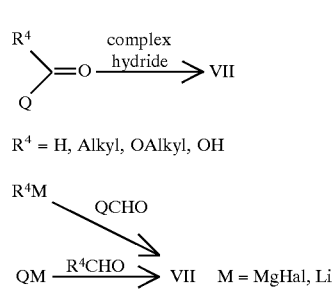

$R^4$ = H, Alkyl, OAlkyl, OH

M = MgHal, Li

-continued

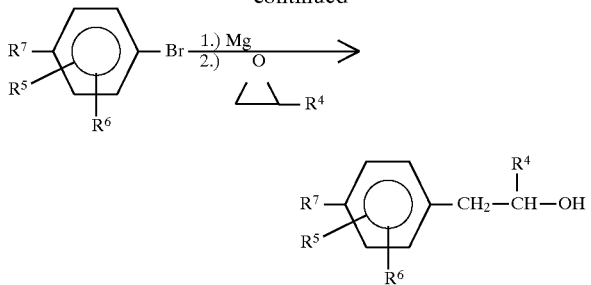

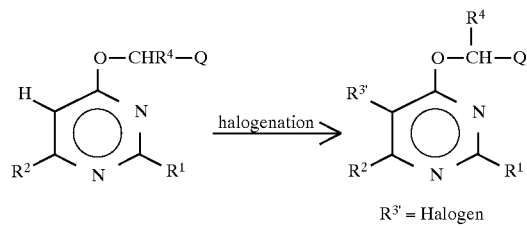

The compounds of the formula V in which R is halogen can be halogenated by known processes.

Examples of substances which can be used in the case of the 5-chloro derivatives are elemental chlorine, sodium hypochlorite, sulfuryl chloride or N-chlorosuccinimide, and elemental bromine or N-bromosuccinimide are particularly suitable for the bromination. Examples of suitable solvents are dichloromethane, chloroform or glacial acetic acid.

The active compounds are well-tolerated by plants and are suitable for controlling animal pests, in particular insects, arachnids, helminths and molluscs, very particularly preferably for controlling insects and arachnids which can be found in agriculture, in livestock breeding, in forests, in the protection of stored products and materials, and in the hygiene field.

A quality of the active compounds which must be emphasized is the fact that they are taken up by the plant via stalk and leaves and transported down to the roots by means of basipetal transport, thus allowing an effective control of nematodes.

The active compounds are active against normally-sensitive and resistant species and against all or individual development stages. The abovementioned pests includes:

From the order of the Acarina, for example *Acarus siro*, Agras spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp., Eutetranychus spp.

From the order of the Isopoda, for example *Oniscus asselus, Armadium vulgare, Porcellio scaber.*

From the order of Diplopoda, for example *Blaniulus guttulatus.*

From the order of Chilopoda, for example *Geophilus carpophagus*, Scutigera spp.

From the order of Symphyla, for example *Scutigerella immaculata.*

From the order of Thysanura, for example *Lepisma saccharina.*

From the order of Collembola, for example *Onychiurus armatus.*

From the order of Orthoptera, for example *Blatta orientalis, Periplaneta americana, Leucophaea maderae,* *Blattella germanica, Acheta domesticus,* Gryllotalpa spp., *Locusta migratoria igratorioides, Melanoplus differentialis, Schistocerca gregaria.*

From the order of Isoptera, for example Reticulitermes spp.

From the order of Anoplura, for example *Phylloxera vastatrix,* Pemphigus spp., *Pediculus humanus corporis,* Haematopinus spp., Linognathus spp.

From the order of Mallophaga, for example Trichodectes spp., Damalinea spp.

From the order of Thysanoptera, for example *Hercinothrips femoralis, Thrips tabaci.*

From the order of Heteroptera, for example Eurygaster spp., *Dysdercus intermedius, Piesma quadrata, Cimex lectularius, Rhodnius prolixus,* Iriatoma spp.

From the order of Homoptera, for example *Aleurodes brassicae, Bemisia tabaci, Trialeurodes vaporariorum, Aphis gossypii, Brevicornyne brassicae, Cryptomyzus ribis, Doralis fabae, Doralis pomi, Eriosoma lanigerum, Hyalopterus arundinis, Macrosiphium avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., Psylla spp.

From the order of Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana.*

From the order of Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonumus spp., Sitophilus spp., *Otiorrhynchus sulcatus, Cosmopolites sordidus, Ceuthorrhynchus assimilis, Hypera postica,* Dermestes spp., Trogoderma, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica.*

From the order of Hymenoptera, for example Diprion spp., Hoplocampa spp., Lasius spp., *Monomorium pharaonis,* Vespa spp.

From the order of Diptera, for example Aedes spp., Anopheles spp., Culex spp., *Drosophila melanogaster,* Musca spp., Fannia spp., *Calliophora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa.*

From the order of Siphonaptera, for example *Xenopsylla cheopsis,* Ceratophyllus spp.

From the order of Arachnida, for example *Scorpio maurus, Latrodectus mactans.*

From the class of the Helminthes, for example Haemonchus, Trichostrongulus, Ostertagia, Cooperia, Chabertia, Strongyloides, Oesophagostomum, Hyostrongulus, Ancylostoma, Ascaris and Heterakis as well as Fasciola, and phytopathogenic nematodes, for example those of the genera Meloidogyne, Heterodera, Ditylenchus, Aphelenchoides, Radopholus, Globodera, Pratylenchus, Longidorus and Xiphinema.

From the class of the Gastropoda, for example Deroceras spp., Arion spp., Lymnaea spp., Galba spp., Succinea spp., Biophalaria spp., Bulinus spp., Oncomelania spp.

From the class of the Bivalva, for example Dreissena spp.

The invention also relates to insecticidal and acaricidal agents which besides the compounds of the formula I contain suitable formulation auxiliaries.

As a rule, the agents according to the invention contain 1 to 95% by weight of the active compounds of the formulae I.

They can be formulated in various ways, depending on the given biological and/or physicochemical parameters.

Examples of possible formulations which are suitable are therefore: wettable powders (WP), emulsifiable concentrates (EC), aqueous solutions (SC), emulsions, sprayable solutions, dispersions on an oil or water base (SC), suspoemulsions (SC), dusting agents (DP), seed-dressing agents, granules in the form of microgranules, spray granules, coated granules and adsorption granules, water-dispersible granules (WG), ULV formulations, microcapsules, waxes or baits.

These individual formulation types are known in principle and described, for example, in: Winnacker-Küchler, "Chemische Technologie" [Chemical Technology], Volume 7, C. Hauser Verlag, Munich, 4th Ed. 1986; van Falkenberg, "Pesticides Formulations", Marcel Dekker, N.Y., 2nd Ed. 1972–73; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust DiluEd., and Carriers", 2nd Ed., Darland Books, Caldwell N.J.; H. v. Olphen, "Introduction to Clay Colloid Chemistry", 2nd Ed., J. Wiley & Sons, New York; Marsden, "Solvents Guide", 2nd Ed., Interscience, New York 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., New York 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other pesticidally active compounds, fertilizers and/or growth regulators, for example in the form of a readymix or a tank mix. Wettable powders are preparations which are uniformly dispersible in water and which, besides the active compound and in addition to a diluent or inert substance, also contain wetting agents, for example polyoxyethylated alkylphenols, polyoxyethylated fatty alcohols, alkyl- or alkylphenol-sulfonates and dispersing agents, for example sodium ligninsulfonate, sodium 2,2'-dinaphthylmethane-6,6'-disulfonate or sodium oleoylmethyltaurate. Emulsifiable concentrates are prepared by dissolving the active compound in an organic solvent, for example butanol, cyclohexanone, dimethylformamide, xylene or else higher-boiling aromatics or hydrocarbons, with the addition of one or more emulsifiers. Emulsifiers which can be used are, for example: calcium salts of alkylarylsulfonic acids, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talc or natural clays, such as kaolin, bentonite, pyrophyllite, or diatomaceous earth. Granules can be prepared either by atomizing the active compound onto adsorptive, granulated inert material or by applying active compound concentrates onto the surface of carrier materials such as sand, kaolinites or of granulated inert material by means of adhesives, for example polyvinyl alcohol, sodium polyacrylate or alternatively mineral oils. Suitable active compounds can also be granulated in the manner which is conventional for the preperation of fertilizer granules, if desired as a mixture with fertilizers.

The active compound concentration in wettable powders is, for example, about 10 to 90% by weight; the remainder to 100% by weight is composed of conventional formulation components. In the case of emulsifiable concentrates, the active compound concentration can be about 5 to 80% by weight. Formulations in the form of dusting agents usually contain 5 to 20% by weight of active compound, sprayable solutions about 2 to 20% by weight. In the case of granules, the active compound content depends partly on whether the active compound is liquid or solid and on which granulation auxiliaries, fillers etc. are used.

In addition, the active compound formulations mentioned contain, if appropriate, the adhesives, wetting agents, dispersing agents, emulsifiers, penetrants, solvents, fillers or carrier materials which are conventional in each case.

For use, the concentrates present in commercially available form are diluted, if appropriate, in a conventional manner, for example using water in the case of wettable powders, emulsifiable concentrates, dispersions and in some cases also microgranules. Preparations in the form of dusting agents and granules and also sprayable solutions are usually not further diluted with other inert substances before use.

The application rate required varies with the external conditions, such as temperature and humidity, inter alia. It can vary within wide limits, for example between 0.005 and 10.0 kg/ha or more of active ingredient; preferably, however, it is between 0.01 and 5 kg/ha.

The active compounds according to the invention can exist in their commercially available formulations and in the use forms prepared from these formulations in the form of mixtures with other active compounds such as insecticides, attractants, sterilants, acaricides, nematicides, fungicides, growth-regulating substances or herbicides.

The pesticides include, for example, phosphates, carbamates, carboxylates, formamidines, tin compounds, and substances produced by microorganisms, inter alia.

Preferred components in the mixture are.

1. from the group comprising the phosphorus compounds acephate, azamethiphos, azinphos-ethyl, azinphosmethyl, bromophos, bromophos-ethyl, chlorfenvinphos, chlormephos, chlorpyrifos, chlorpyrifos-methyl, demeton, demeton-S-methyl, demeton-S-methyl-sulfone, dialifos, diazinon, dichlorvos, dicrotophos, O,O-1,2,2,2-tetrachloroethyl phosphorothioate (SD 208 304), dimethoate, disulfoton, EPN, ethion, ethoprophos, etrimfos, famphur, fenamiphos, fenitrothion, fensulfothion, fenthion, fonofos, formothion, heptenophos, isazofos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, propetamphos, prothiofos, pyraclofos pyridapenthion, quinalphos, sulprofos, temephos, terbufos, tetraclorvinphos, thiometon, triazophos, trichlorphon, vamidothion;

2. from the group comprising the carbamates aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenylbutyryl(methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio (ethylideneamino) N-methyl-N-(morpholinothio) carbamate (UC 51717);

3. from the group comprising the carboxylates allethrin, alphametrin, 5-benzyl-3-furylmethyl (E)-(1R) -cis-2,2-dimethyl-3-(2-oxothiolan-3-ylidenemethyl)cyclo-propanecarboxylate, bioallethrin, bioallethrin ((S)-cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cyclroprothrin, cyfluthrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D-isomer), permethrin, phenothrin ((R)-isomer), d-pralethrin, pyrethrins (natural products), resmethrin, tefluthrin, tetramethrin, tralomethrin;

4. from the group comprising the amidines amitraz, chlordimeform;

5. from the group comprising the tin compounds cyhexatin, fenbutatin oxide;

6. others abamectin, *Bacillus thuringiensis*, bensultap, binapacryl, bromopropylate, buprofezin, camphechlor, cartap, chlorbenzilate, chlorfluazuron, 2-(4-chloro-phenyl)-4,5-diphenylthiophene (UBI-T 930), clorfentezine, 2-naphthylmethyl cyclopropanecarboxy-late (Ro 12-0470), cyromazin, ethyl N-(3,5-dichloro-4-(1,1,2,3,3,3-hexafluoro-1-propoxy)phenyl) carbamoyl)-2-chlorobenzocarboximidate, DDT, dicofol, N-(N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidine)-2,4-xylidine, dinobuton, dinocap, endosulfan, ethofenprox, (4-ethoxyphenyl)(dimethyl)(3-(3-phenoxyphenyl) propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl) diphenyl ether (MTI 800) granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam and triflumuron.

The active substance content of the use forms prepared from the commercially available formulations can be from 0.00000001 to 100% by weight of active substance, preferably between 0.00001 and 1% by weight.

Application is effected in a conventional fashion, matched to the use forms.

The active substances according to the invention are also suitable for combating endo- and ectoparasites in the veterinary medicine field or in the field of animal husbandry.

The active substances according to the invention are administered in a known manner such as by oral administration in the form of, for example, tablets, capsules, drinks, granules, by dermal administration, for example in the form of dipping, spraying, pouring-on and spotting-on and applying a powder, as well as by parenteral administration, for example in the form of an injection.

Accordingly, the novel compounds of the formula I according ing to the invention can also be employed particularly advantageously in livestock breeding (for example cattle, sheep, pigs and poultry such as, inter alia, chickens and geese). In a preferred embodiment of the invention, the novel compounds, if appropriate in the form of suitable formulations (cf. above) and, if appropriate, together with the drinking water or feed, are administered orally to the animals. Since the novel compounds are effectively excreted with the feces, the development of insects in the feces of the animals can thus be prevented in a very simple manner. The dosage rates and formulations which are suitable in each case depend in particular on the species and the development state of the livestock and also on the infection pressure and readily be used in cattle, for example at dosage rates of 0.01 to 1 mg/kg of body weight, using customary methods.

The compounds of the formula I according to the invention are distinguished by an outstanding fungicidal action. Fungal pathogens which have already penetrated the plant tissue can be successfully controlled in a curative fashion. This is particularly important and advantageous in the case of those fungal diseases where a control with otherwise customary fungicides is no longer effective once infection has taken place. The centre of action of the compounds claimed embraces a large number of various economically important phytopathogenic fungi such as, for example, *Pyricularia oryzae, Venturia inaequalis, Cercospora beticola*, powdery mildew species, Fusarium species, *Plasmopora viticola*, various rusts and *Pseudocercoporella herpotrichoides*.

Moreover, the compounds according to the invention are also suitable for use in industrial sectors, for example as a wood preservative, as a preservative in paints, in cooling lubricants for metalworking, or as preservatives in drilling and cutting oils.

The invention also relates to fungicidal agents which contain the compounds of the formula I together with suitable formulation auxiliaries. As a rule, the agents according to the invention contain 1 to 95% by weight of the active substances of the formula I.

They can be formulated in various ways, depending on the given biological and/or physicochemical parameters. Examples of possible formulations are therefore: wettable powders (WP), emulsifiable concentrates (EC), aqueous dispersions (SC), dusting agents (DP), seed-dressing agents, granules in the form of water-dispersible granules (WG), ULV formulations, microcapsules, waxes or baits.

These individual formulation types are known in principle and are described, for example, in: Winnacker-Küchler, "Chemische Technologie [Chemical Technology]", Volume 7, C. Hauser Verlag Munich, 4th Ed., 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The necessary formulation auxiliaries such as inert materials, surfactants, solvents and other additives are also known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, New York; Marsden, "Solvents Guide", 2nd Ed., Interscience, New York 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts]", Wiss. Verlagsgesell., Stuttgart 1976; Winnacker-Küfchler, "Chemische Technologie [Chemical Technology]", Volume 7, C. Hauser Verlag Munich, 4th Ed. 1986.

Based on these formulations, it is also possible to prepare combinations with other pesticidally active substances, fertilizers and/or growth regulators, for example in the form of a readymix or a tank mix.

Wettable powders are preparations which are uniformly dispersible in water and which, besides the active substance and in addition to a diluent or inert substance, also contain wetting agents, for example polyoxethylated alkylphenols, polyoxethylated fatty alcohols, alkyl- or alkylphenolsulfonates, and dispersing agents, for example sodium ligninsulfonate, sodium 2,2'-dinaphthylmethane-6, 6'-disulfonate, sodium dibutylnaphthalenesulfonate, or sodium oleylmethyltaurate. Emulsifiable concentrates are prepared by dissolving the active substance in an organic solvent, for example butanol, cyclohexanone, dimethylformamide, xylene or else higher-boiling aromatics or hydrocarbons, with the addition of one or more emulsifiers. Emulsifiers which can be used are, for example: calcium salts of alkylarylsulfonic acids, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, sorbitan fatty acid esters, polyoxyethylene sorbitan fatty acid esters or polyoxyethylene sorbitol esters.

Dusting agents are obtained by grinding the active substance with finely divided solid substances, for example talc or natural clays, such as kaolin, bentonite, pyrophyllite or diatomaceous earth. Granules can be prepared either by atomizing the active substance onto adsorptive, granulated inert material or by applying active substance concentrates onto the surface of carrier materials such as sand, kaolinites or of granulated inert material by means of adhesives, for example polyvinyl alcohol, sodium polyacrylate or, alternatively mineral oils. Suitable active substances can also be granulated in the manner which is conventional for the preparation of fertilizer granules, if desired as a mixture with fertilizers.

The active substance concentration in wettable powders is, for example, about 10 to 90% by weight; the remainder to 100% by weight is composed of conventional formulation components. In the case of emulsifiable concentrates, the active substance concentration can be about 5 to 80% by weight. Formulations in the form of dusting agents usually contain 5 to 20% by weight. In the case of granules, the active substance content depends partly on whether the active compound is liquid or solid and on which granulation auxiliaries, fillers etc. are used.

In addition, the active substance formulations mentioned contain, if appropriate, the adhesives, wetting agents, dispersing agents, emulsifiers, penetrants, solvents, fillers or carrier materials which are conventional in each case.

For use, the concentrates present in commercially available form are diluted, if appropriate, in a conventional manner, for example using water in the case of wettable powders, emulsifiable concentrates, dispersions and in some cases, also microgranules.

Preparations in the form of dusts or granules and also sprayable solutions are usually not further diluted with other inert substances before use.

The application rate varies with the external conditions, such as temperature and humidity, inter alia. It can vary within wide limits, for example between 0.005 and 10.0 kg/ha or more of active ingredient; preferably, however, it is between 0.01 and 5 kg/ha.

In their commercially available formulations, the active substances according to the invention can be applied either by themselves or in combination with other fungicides known from the literature.

Suitable fungicides known from the literature which can be combined according to the invention with the compounds of the formula I are: anilazine, benalaxyl, benodanil, benomyl, binapacryl, bitertanol, buthiobate, captafol, captan, carbendazim, carboxin, CGD-94240 F, chlobenzthiazone, chlorthalonil, cymoxanil, cyproconazole, cyprofuram, dichlofluanid, dichlomezin, diclobutrazol, diethofencarb, difluconazole, dimethirimol, dimetlomorph, diniconazole, dinocap, dithianon, dodemorph, dodine, edifenfos, ethirimol, etridiazol, fenarimol, fenfuram, fenpiclonil, fenpropidin, fenpropomorph, fentin acetate, fentin hydroxide, fluaziram, fluobenzimine, fluorimide, flusilazole, furalaxyl, furmecyclox, guazatine, hexaconazole, imazalil, iprobenfos, iprodione, isoprothiolane, copper compounds such as copper oxychloride, oxinecopper, copper oxide, mancozeb, maneb, mepronil, metalaxyl, methasulfocarb, methfuroxam, myclobutanil, nabam, nitrothal-isopropyl, nuarimol, ofurace, oxadixyl, oxycarboxin, penconazole, pencycuron, PP 969, probenazole, probineb, prochloraz, procymidon, propamocarb, propiconazole, prothiocarb, pyracarbolide, pyrifenox, pyroquilon, rabenzazole, sulfur, tebuconazole, thiabendazole, thiofanate-methyl, thiram, tolclofos-methyl, tolylfluanid, triadimefon, triadimenol, tricyclazole, tridemorph, triflumizol, triforine, vinchlozolin, zineb, sodium dodecylsulfonate, sodium dodecylsulfate, sodium C13/C15-alcohol ether sulfonate, sodium cetostearyl phosphates, dioctylsodium sulfosuccinate, sodium isopropylnaphthalenesulfonate, sodium methylenebisnaphthalenesulfonate, cetyltrimethylammonium chloride, salts of long-chain primary, secondary or tertiary amines, alkylproypleneamines, laurylpyrimidinium bromide, ethoxylated quaternized fatty amines, alkyldimethylbenzylammonium chloride and 1-hydroxyethyl-2-alkylimidazoline.

The abovementioned components represent known active substances, many of which are described in C. R. Worthing, S. B. Walker, The Pesticide Manual, 7th Edition (1983), British Crop Protection Council.

Moreover, the active substances according to the invention, in particular those of the examples mentioned, can exist in their commercially available formulations and in the use forms prepared from these formulations in the form of mixtures with other active substances such as insecticides, attractants, sterilants, acaricides, nematicides, fungicides, growth-regulating substances or herbicides.

The active substance content of the use forms prepared from the commercially available formulations can vary within wide limits, the active substance concentration of the use forms can be between 0.0001 and 100% by weight of active substance, preferably between 0.001 and 1% by weight. Application is effected in a conventional fashion, matched to the use forms.

The examples which follow are intended to illustrate the invention.

A. Formulation Examples a) A dusting agent is obtained by mixing 10 parts by is weight of active substance and 90 parts by weight of talc as inert substance and comminuting the mixture in a hammer mill.

b) A wettable powder which is readily dispersible in water is obtained by mixing 25 parts by weight of active substance, 64 parts by weight of kaolin-containing quartz as inert substance, 10 parts by weight of potassium ligninsulfonate and 1 part by weight of sodium oleoylmethyltaurate as wetting and dispersing agent, and grinding the mixture in a pinned-disk mill.

c) A dispersion concentrate which is readily dispersible in water is obtained by mixing 40 parts by weight of active substance with 7 parts by weight of a sulfosuccinic monoester, 2 parts by weight of a sodium ligninsulfonate and 51 parts by weight of water, and grinding the mixture in a ball mill to a fineness of below 5 microns.

d) An emulsifiable concentrate is obtained from 15 parts by weight of active substance, 75 parts by weight of cyclohexanone as the solvent and 10 parts by weight of oxyethylated nonylphenol (10 EO) as emulsifier.

e) Granules can be prepared from 2 to 15 parts by weight of active substance and an inert granule carrier material such as attapulgite, pumice granules and/or quartz sand. It is expedient to use a suspension of the wettable powder of Example b) with a solids content of 30%, which is sprayed onto the surface of attapulgite granules, and this is then dried and mixed intimately. The proportion by weight of the wettable powder is approx. 5% and that of the inert carrier material approx. 95% of the finished granules.

B) Chemical Examples

EXAMPLE A

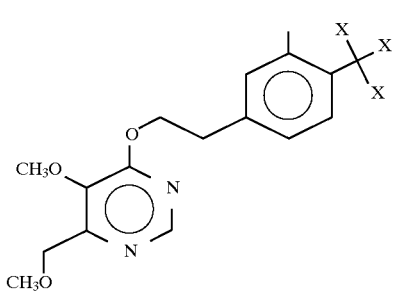

5.4 g (0.03 mol) of 2-(4-tert-butylphenyl)ethanol were added dropwise at 50° C. to a suspension of 1.2 g (0.03 mol) of sodium hydride (60% dispersion in oil) in 50 ml of dry dimethylformamide, and the mixture was stirred until the evolution of hydrogen had ceased. The mixture was cooled to 0° C., and 4.7 g (0.025 mol) of 4-chloro-5-methoxy-6-methoxymethylpyrimidine (Coll. Czechoslov. Chem. Commun. 33, 2266 (1968)) were added. The mixture was stirred for 1 hour at room temperature and for 2 hours at 100° C. After the solvent had been stripped off, the residue was taken up in dichloromethane/water, and the organic phase was dried and evaporated on a rotary evaporator. The crude product was chromatographed on silica gel using ethyl acetate. 3.8 g (46% of theory) of 4-[2-(4-tert-butylphenyl)ethoxy]-5 -methoxy-6 -methoxymethylpyrimidine were obtained in the form of a yellow oil.

EXAMPLE B

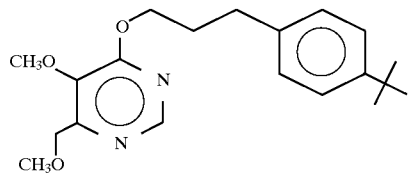

A solution of 5.8 g (0.03 mol) of 3-(4-tert.-butylphenyl)propanol in 20 ml of dry dimethylformamide was added dropwise at 10°–20° C. to a mixture of 1.2 g (0.03 mol) of sodium hydride (60% dispersion in oil) and 5.7 g (0.03 mol) of 4-chloro-5-methoxy-6-methoxymethylpyrimidine in 50 ml of dry dimethylformamide. The mixture was stirred for 1 hour at room temperature and for 2 hours at 100° C. Work-up and chromatographic purification analogous to Example A gave 2.5 g (24%) of 4-[3-(4-tert.-butylphenyl)propoxy]-5-methoxy-6-methoxymethylpyrimidine in the form of a yellow oil.

EXAMPLE C

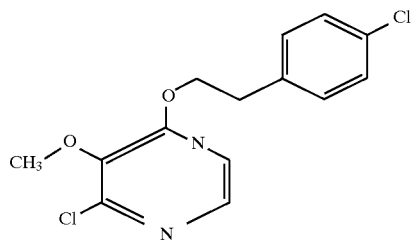

2.40 g (15.2 mmol) of 2-(4-chlorophenyl)ethanol were added dropwise at 40° C. to a suspension of 680 mg (22.7 mmol) of sodium hydride (80% suspension in oil) in 40 ml of dry tetrahydrofuran, and the mixture was stirred until the evolution of hydrogen had ceased. The mixture was then allowed to cool to room temperature, whereupon 2.7 g (15.2 mmol) of 4,6-dichloro-5-methoxypyrimidine (Monatshefte Chem. 96, 1661 (1965) were added in portions. The mixture was stirred for 1 hour at room temperature and for 4 hours at 40° C. For work-up, the reaction mixture was poured into saturated ammonium chloride solution and extracted with diethyl ether. The combined organic phase was dried over magnesium sulfate and concentrated in vacuo. The residue was chromatographed on silica gel using n-heptane/ethyl acetate (4:1). 4.0 g (88% of theory) of 4-[2-(4-chlorophenyl)ethoxy]-5-methoxy-6-chloropyrimidine was obtained in the form of a viscous oil which crystallized slowly upon drying (melting point 70°–71° C.).

EXAMPLE D

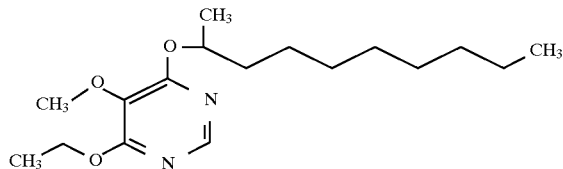

2.7 g (17.0 mmol) of 2-decanol were added dropwise at 50° C. to a suspension of 650 mg (21.6 mmol) of sodium hydride (80% suspension in oil) in 60 ml of dry dimethylformamide, and the mixture was stirred until the evolution of hydrogen had ceased. The mixture was cooled to room temperature and 3.0 g (15.9 mmol) of 4-chloro-5-methoxy-6-ethoxypyrimidine (preparation analogously to Example C) were added in portions. After 30 minutes, the reaction temperature was increased to 50° C., and stirring was continued for 12 hours. The reaction mixture was poured into saturated ammonium chloride solution and subsequently extracted with diethyl ether. The combined organic phase was washed with water, dried over magnesium sulfate and concentrated in vacuo. The residue was chromatographed on silica gel using n-heptane/ethyl acetate (4:1). 1.4 g (28% of theory) of 4-(2-decyloxy)-5-methoxy-6-ethoxypyrimidine were obtained in the form of a yellow oil.

EXAMPLE E

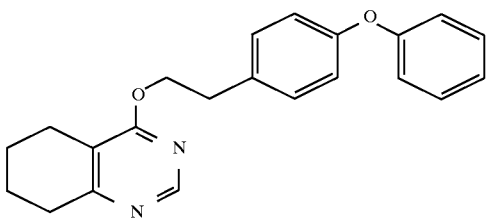

3.8 g (17.8 mmol) of 2-[4-(phenoxy)phenyl]ethanol were added to a suspension of 700 mg (23.3 mmol) of sodium hydride (80% suspension in oil) in 50 ml of dry tetrahydrofuran, and the mixture was stirred at 50° C. until the evolution of hydrogen had ceased. The mixture was cooled to room temperature, and 3.0 g (17.8 mmol) of 4-chloro-5,6,7,8-tetrahydroquinazoline were added. The mixture was then heated for 5 hours at 40° C. The reaction mixture was poured into saturated ammonium chloride solution and subsequently extracted with diethyl ether. The combined organic phase was dried over magnesium sulfate and concentrated in vacuo. The residue was chromatographed on silica gel using n-heptane/ethyl acetate (2:1). 3.2 g of 4-[2-(4-(phenoxy)phenyl)ethoxy]-5,6,7,8-tetrahydroquinazoline were obtained in the form of a viscous yellow oil.

Further examples can be found in Table I below. The radicals $R^1$ to $R^4$ and Q which are mentioned in the table correspond to the symbols in formula I

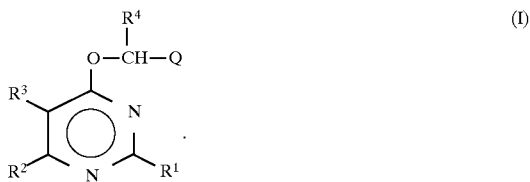

(I)

| Example No. | $R^1$ | $R^2$ | $R^3$ | $R^4$ | Q | M.p. |
|---|---|---|---|---|---|---|
| 001 | H | $CH_2OCH_3$ | $OCH_3$ | $CH_3$ | $(CH_2)_3CH_3$ | oil |
| 002 | H | $CH_2OCH_3$ | $OCH_3$ | $CH_3$ | $(CH_2)_5CH_3$ (R-Form) | oil |
| 003 | H | $CH_2OCH_3$ | $OCH_3$ | $CH_3$ | $(CH_2)_5CH_3$ (S-Form) | oil |
| 004 | H | $CH_2OCH_3$ | $OCH_3$ | $CH_3$ | $(CH_2)_7CH_3$ | oil |
| 005 | H | $CH_2OCH_3$ | $OCH_3$ | H | $(CH_2)_8CH_3$ | oil |
| 006 | H | $CH_2OCH_3$ | $OCH_3$ | $CF_3$ | $(CH_2)_7CH_3$ | oil |
| 007 | H | $-(CH_2)_4-$ | | $CF_3$ | $(CH_2)_7CH_3$ | oil |
| 008 | H | $CH_2OCH_3$ | $OCH_3$ | $C_2H_5$ | $(CH_2)_4CH_3$ | oil |
| 009 | H | $OCH_3$ | $OCH_3$ | $CH_3$ | $(CH_2)_7CH_3$ | oil |
| 010 | H | Cl | $OCH_3$ | $CH_3$ | $(CH_2)_7CH_3$ | oil |
| 011 | H | $OC_2H_5$ | $OCH_3$ | $CH_3$ | $(CH_2)_7CH_3$ | oil |
| 012 | H | $C_2H_5$ | $OCH_3$ | $CH_3$ | $(CH_2)_7CH_3$ | oil |
| 013 | H | $C_2H_5$ | $C_2H_5$ | $CH_3$ | $(CH_2)_7CH_3$ | oil |
| 014 | H | $-(CH_2)_4-$ | | $CH_3$ | $(CH_2)_7CH_3$ | oil |
| 015 | H | $CH_2OCH_3$ | $OCH_3$ | H | $CH_2O(CH_2)_5CH_3$ | oil |
| 016 | H | $CH_2OCH_3$ | $OCH_3$ | H | $CH_2O(CH_2)_7CH_3$ | oil |
| 017 | H | $CH_2OCH_3$ | $OCH_3$ | H | $CH_2O(CH_2)_9CH_3$ | oil |
| 018 | H | Cl | $OCH_3$ | H | $(CH_2)O(CH_2)_5CH_3$ | oil |
| 019 | H | Cl | $OCH_3$ | H | $CH_2O(CH_2)_7CH_3$ | oil |
| 020 | H | Cl | $OCH_3$ | H | $CH_2O(CH_2)_9CH_3$ | oil |
| 021 | H | $OCH_3$ | $OCH_3$ | H | $CH_2O(CH_2)_7CH_3$ | oil |
| 022 | H | $OCH_3$ | $OCH_3$ | H | $CH_2O(CH_2)_9CH_3$ | 32 |
| 023 | H | $CH_2OCH_3$ | $OCH_3$ | H | $(CH_2)_3CH-(CH_2)_3CH(CH_3)_2CH_3$ | Oil |
| 024 | H | $CH_2OCH_3$ | Cl | $CH_3$ | $(CH_2)_7CH_3$ | oil |
| 025 | H | $CF_3$ | Cl | $CH_3$ | $(CH_2)_7CH_3$ | oil |

-continued

| | | | | | | |
|---|---|---|---|---|---|---|
| 026 | H | CH₂OCH₃ | OCH₃ | H | CH₂—O—C₆H₄—C(CH₃)₃ (4-tert-butylphenoxymethyl) | oil |
| 027 | H | OCH₃ | OCH₃ | H | CH₂—O—C₆H₄—C(CH₃)₃ (4-tert-butylphenoxymethyl) | oil |
| 028 | H | Cl | OCH₃ | H | CH₂—O—C₆H₄—C(CH₃)₃ (4-tert-butylphenoxymethyl) | oil |
| 029 | H | —(CH₂)₄— | | H | CH₂—O—C₆H₄—C(CH₃)₃ (4-tert-butylphenoxymethyl) | oil |
| 030 | H | —(CH₂)₄— | | H | CH₂—O—(2,5-dimethylphenyl) | 62–66 |
| 031 | H | Cl | OCH₃ | H | CH₂—O—(2,5-dimethylphenyl) | oil |
| 032 | H | Cl | OCH₃ | H | CH₂—O—C₆H₄—O—C₆H₅ (4-phenoxyphenoxymethyl) | 55 |
| 033 | H | CH₂OCH₃ | OCH₃ | H | CH₂—O—C₆H₄—O—C₆H₅ (4-phenoxyphenoxymethyl) | oil |
| 034 | H | CH₂OCH₃ | OCH₃ | H | CH₂—O—(4-methylphenyl) | oil |
| 035 | H | CH₂OCH₃ | OCH₃ | H | CH₂—O—(2,5-dimethylphenyl) | oil |
| 036 | H | CH₂OCH₃ | OCH₃ | H | CH₂O—C₆H₄—O—(2,4-dichlorophenyl) | oil |
| 037 | H | Cl | OCH₃ | H | CH₂O—C₆H₄—O—(2,4-dichlorophenyl) | oil |
| 038 | H | —(CH₂)₄— | | H | CH₂O—C₆H₄—O—(2,4-dichlorophenyl) | 77–79 |

-continued
| | | | | | | |
|---|---|---|---|---|---|---|
| 039 | H | —(CH$_2$)$_4$— | | H | 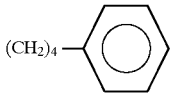 | oil |
| 040 | H | CH$_2$OCH$_3$ | OCH$_3$ | H | 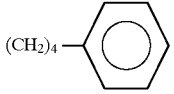 | oil |
| 041 | H | H | OCH$_3$ | H | 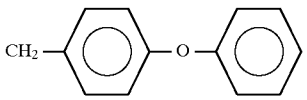 | 42–43 |
| 042 | H | H | OCH$_3$ | H | 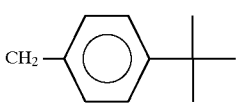 | oil |
| 043 | H | —(CH$_2$)$_4$— | | H | 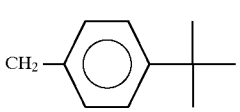 | 62–63 |
| 044 | H | —(CH$_2$)$_4$— | | H | 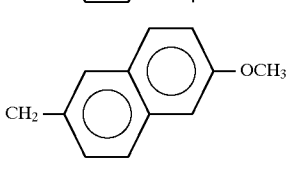 | 87–89 |
| 045 | H | CH$_2$OCH$_3$ | OCH$_3$ | H | 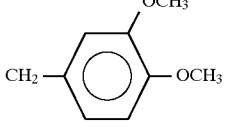 | oil |
| 046 | H | CH$_2$OCH$_3$ | OCH$_3$ | H | 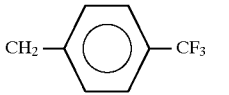 | oil |
| 047 | H | C$_2$H$_5$ | C$_2$H$_5$ | H | 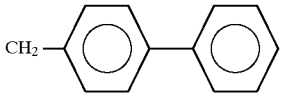 | oil |
| 048 | H | C$_2$H$_5$ | C$_2$H$_5$ | H |  | 65–67 |
| 049 | H | —(CH$_2$)$_4$— | | H | 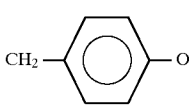 | oil |
| 050 | H | —(CH$_2$)$_4$— | | H | 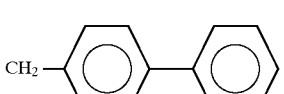 | 94–95 |
| 051 | H | C$_2$H$_5$ | C$_2$H$_5$ | H | 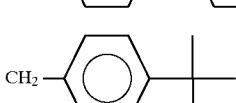 | Oil |
| 052 | H | C$_2$H$_5$ | C$_2$H$_5$ | H | 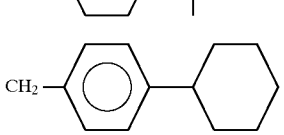 | Oil |
| 053 | H | C$_2$H$_5$ | H | H | (CH$_2$)$_6$CH$_3$ | Oil |

-continued

| No. | | | | | R group | Yield |
|---|---|---|---|---|---|---|
| 054 | H | CH₂OCH₃ | OCH₃ | H | CH₂–C₆H₄–C₆H₅ (biphenylmethyl) | Oil |
| 055 | H | Cl | OCH₃ | C₂H₅ | (CH₂)₆CH₃ | 63 |
| 056 | H | C₂H₅ | Cl | H | CH₂–C₆H₄–C₆H₅ (biphenylmethyl) | oil |
| 057 | H | —(CH₂)₄— | | H | CH₂–C₆H₄–C₆H₅ (biphenylmethyl) | 83 |
| 058 | H | CH₂OCH₃ | OCH₃ | H | CH₂OCH₂–C₆H₅ | oil |
| 059 | H | OCH₃ | OCH₃ | H | CH₂OCH₂–C₆H₅ | oil |
| 060 | H | C₂H₅ | Cl | H | CH₂OCH₂–C₆H₅ | oil |
| 061 | H | Cl | OCH₃ | H | CH₂OCH₂–C₆H₅ | oil |
| 062 | H | CH₂OCH₃ | OCH₃ | C₂H₅ | –C₆H₄–O–C₆H₄–CH₃ | oil |
| 063 | H | CH₂OCH₃ | OCH₃ | H | C(CH₃)₂CH₂OCH₂–C₆H₄–O–C₆H₅ | oil |
| 064 | H | CH₂OCH₃ | OCH₃ | H | –C₆H₅ | oil |
| 065 | H | CH₂OCH₃ | OCH₃ | H | –C₆H₄–C(CH₃)₃ | oil |
| 066 | H | CH₂OCH₃ | OCH₃ | H | –C₆H₄–O–C₆H₅ | oil |
| 067 | H | CH₂OCH₃ | OCH₃ | H | –C₆H₃(F)–O–C₆H₅ | oil |

-continued

| | | | | | | |
|---|---|---|---|---|---|---|
| 068 | H | Cl | OCH₃ | H | 4-phenoxyphenyl | oil |
| 069 | H | C₂H₅ | H | H | 4-methylphenyl | oil |
| 070 | H | C₂H₅ | Cl | C₂H₅ | 4-(4-methylphenoxy)phenyl | oil |
| 071 | H | CF₂CH₂O | H | H | 2-fluoro-4-phenoxyphenyl | oil |
| 072 | H | CH₂OCH₃ | OCH₃ | H | —CH₂—(4-chlorophenyl) | oil |
| 073 | H | CH₂OCH₃ | OCH₃ | H | —CH₂—(4-tert-butylphenyl) | oil |
| 074 | H | CH₂OCH₃ | OCH₃ | H | —CH₂—(4-phenylphenyl) | oil |
| 075 | H | CH₂OCH₃ | OCH₃ | H | —CH₂—(4-phenoxyphenyl) | oil |
| 076 | H | CH₂OCH₃ | OCH₃ | H | —CH₂—(2-naphthyl) | oil |
| 077 | H | CH₂OCH₃ | OCH₃ | H | —CH₂—(4-methylphenyl) | oil |
| 078 | H | CH₂OCH₃ | OCH₃ | H | —CH₂—(4-fluorophenyl) | oil |
| 079 | H | CH₂OCH₃ | OCH₃ | H | —CH₂—(6-methoxy-2-naphthyl) | 43–45 |
| 080 | H | CH₂OCH₃ | OCH₃ | H | —C(CH₃)₂—(4-methoxyphenyl) | oil |

-continued

| | | | | | | |
|---|---|---|---|---|---|---|
| 081 | H | CH$_2$OCH$_3$ | OCH$_3$ | H | 4-C(CH$_3$)$_2$, 4-OC$_2$H$_5$ substituted phenyl | oil |
| 082 | H | CH$_2$OCH$_3$ | OCH$_3$ | H | CH$_2$CH$_2$-(4-methylphenyl) | oil |
| 083 | H | Cl | OCH$_3$ | H | CH$_2$-(4-methylphenyl) | oil |
| 084 | H | Cl | OCH$_3$ | H | CH$_2$-(4-fluorophenyl) | 57–59 |
| 085 | H | Cl | OCH$_3$ | H | CH$_2$-(2-naphthyl) | 79–81 |
| 086 | H | Cl | OCH$_3$ | H | CH$_2$-(6-methoxy-2-naphthyl) | 81 |
| 087 | H | Cl | OCH$_3$ | H | CH$_2$-(4-phenoxyphenyl) | oil |
| 088 | H | Cl | OCH$_3$ | H | CH$_2$-(4-phenylphenyl) | oil |
| 089 | H | Cl | OCH$_3$ | H | CH$_2$-(4-chlorophenyl) | 70–71 |
| 090 | H | Cl | OCH$_3$ | H | CH$_2$-(4-tert-butylphenyl) | oil |
| 091 | H | Cl | OCH$_3$ | H | CH$_2$-(3,4-dimethylphenyl) | oil |
| 092 | H | OCH$_3$ | OCH$_3$ | H | —CH$_2$-(4-tert-butylphenyl) | oil |
| 093 | H | CH$_2$OCH$_3$ | OCH$_3$ | C$_2$H$_5$ | 4-(4-chlorophenoxy)phenyl | oil |
| 094 | H | C$_2$H$_5$ | Cl | C$_2$H$_5$ | 4-(4-chlorophenoxy)phenyl | oil |

-continued
| | | | | | | | |
|---|---|---|---|---|---|---|---|
| 095 | H | C₂H₅ | | Cl | H |  | oil |
| 096 | H | C₂H₅ | | Cl | H | 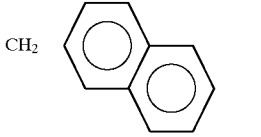 | oil |
| 097 | H | C₂H₅ | | Cl | H | 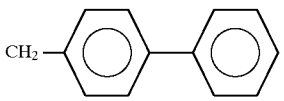 | oil |
| 098 | H | C₂H₅ | | Cl | H | 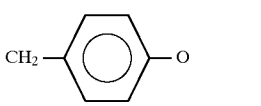 | oil |
| 099 | H | C₂H₅ | | Cl | H | 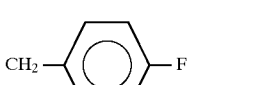 | oil |
| 100 | H | OC₂H₅ | | H | H | 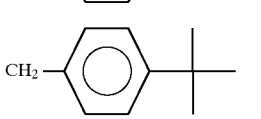 | oil |
| 101 | H | OCH₂CF₃ | | H | H | 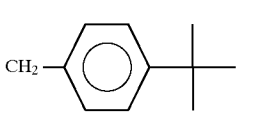 | oil |
| 102 | H | OCH₃ | | H | H | 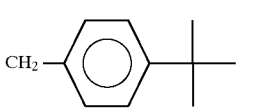 | oil |
| 103 | H | | —(CH₂)₄— | | C₂H₅ | 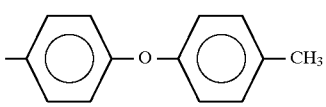 | oil |
| 104 | H | | —(CH₂)₄— | | C₂H₅ | 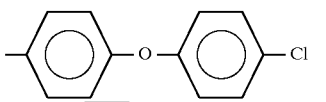 | oil |
| 105 | H | CH₂OCH₃ | | OCH₃ | CH₃ | 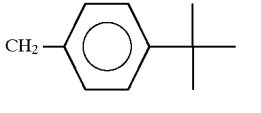 | oil |
| 106 | H | C₂H₅ | | Cl | CH₃ | 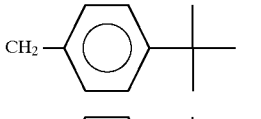 | oil |
| 107 | H | | —(CH₂)₃— | | CH₃ | 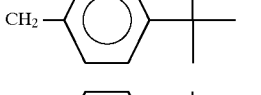 | oil |
| 108 | H | | —(CH₂)₄— | | CH₃ | 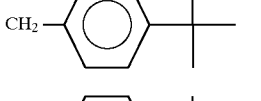 | oil |
| 109 | CH₃ | CH₂OCH₃ | | OCH₃ | H | 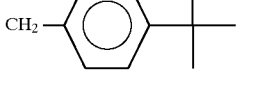 | oil |

| | | | | | |
|---|---|---|---|---|---|
| 110 | H | CH$_2$OCH$_3$ | OCH$_3$ | C$_2$H$_5$ | 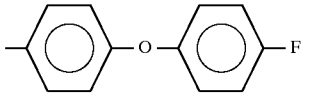 |
| 111 | H | C$_2$H$_5$ | Cl | C$_2$H$_5$ | 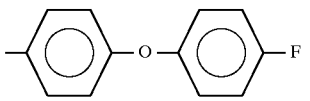 |
| 112 | H | —(CH$_2$)$_4$— | | C$_2$H$_5$ | 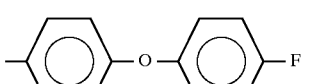 |
| 113 | H | CH$_2$OCH$_3$ | OCH$_3$ | C$_2$H$_5$ | 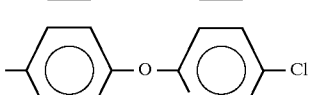 |
| 114 | H | C$_2$H$_5$ | Cl | C$_2$H$_5$ |  |
| 115 | H | —(CH$_2$)$_4$— | | C$_2$H$_5$ | 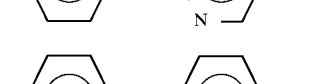 |
| 116 | H | CH$_2$OCH$_3$ | OCH$_3$ | C$_2$H$_5$ | 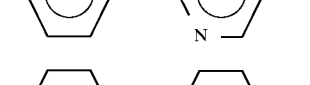 |
| 117 | H | C$_2$H$_5$ | Cl | C$_2$H$_5$ | 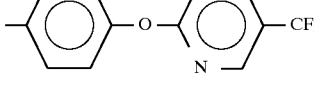 |
| 118 | H | —(CH$_2$)$_4$— | | C$_2$H$_5$ | 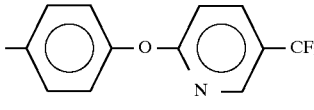 |
| 119 | H | CH$_2$OCH$_3$ | OCH$_3$ | C$_2$H$_5$ | 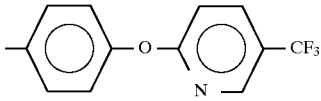 |
| 120 | H | C$_2$H$_5$ | Cl | C$_2$H$_5$ | 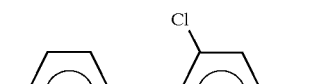 |
| 121 | H | —(CH$_2$)$_4$— | | C$_2$H$_5$ | 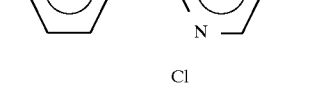 |
| 122 | H | CH$_2$OCH$_3$ | OCH$_3$ | C$_2$H$_5$ | 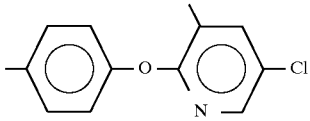 |

-continued
| | | | | | |
|---|---|---|---|---|---|
| 123 | H | C₂H₅ | Cl | C₂H₅ | 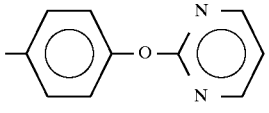 |
| 124 | H | —(CH₂)₄— | | C₂H₅ | 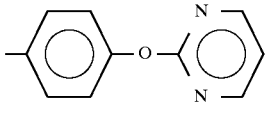 |
| 125 | H | CH₂OCH₃ | OCH₃ | C₂H₅ | 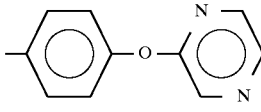 |
| 126 | H | C₂H₅ | Cl | C₂H₅ | 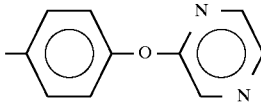 |
| 127 | H | —(CH₂)₄— | | C₂H₅ | 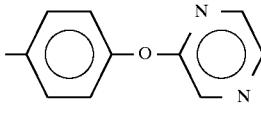 |
| 128 | H | CH₂OCH₃ | OCH₃ | C₂H₅ | 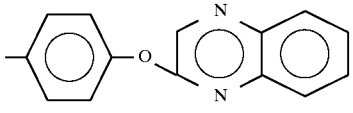 |
| 129 | H | C₂H₅ | Cl | C₂H₅ | 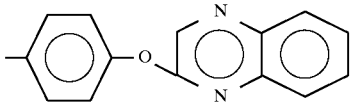 |
| 130 | H | —(CH₂)₄— | | C₂H₅ | 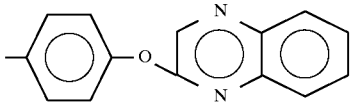 |
| 131 | H | CH₂OCH₃ | OCH₃ | C₂H₅ | 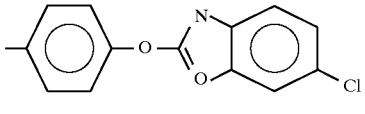 |
| 132 | H | C₂H₅ | Cl | C₂H₅ | 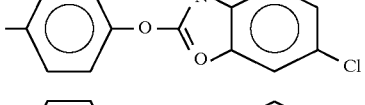 |
| 133 | H | —(CH₂)₄— | | C₂H₅ | 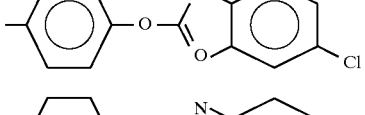 |
| 134 | H | CH₂OCH₃ | OCH₃ | C₂H₅ | 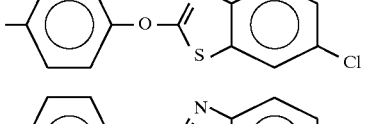 |
| 135 | H | C₂H₅ | Cl | C₂H₅ | 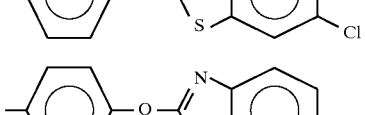 |
| 136 | H | —(CH₂)₄— | | C₂H₅ | 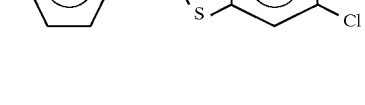 |

-continued
| | | | | | | |
|---|---|---|---|---|---|---|
| 137 | H | CH₂OCH₃ | OCH₃ | C₂H₅ | 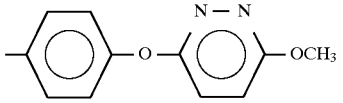 | |
| 138 | H | C₂H₅ | Cl | C₂H₅ | 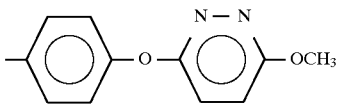 | |
| 139 | H | —(CH₂)₄— | | C₂H₅ | 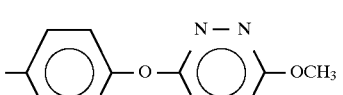 | |
| 140 | H | CH₂OCH₃ | OCH₃ | C₂H₅ | 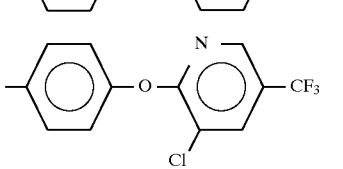 | |
| 141 | H | C₂H₅ | Cl | C₂H₅ | 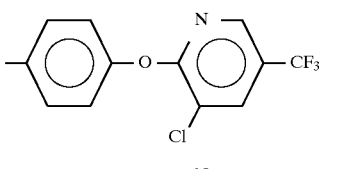 | |
| 142 | H | —(CH₂)₄— | | C₂H₅ | 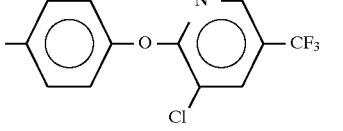 | |
| 143 | H | CH₂OCH₃ | OCH₃ | H | 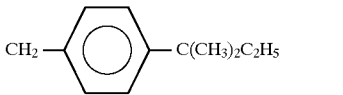 | oil |
| 144 | H | C₂H₅ | Cl | H | 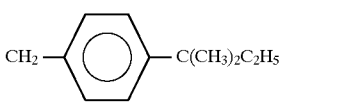 | oil |
| 145 | H | —(CH₂)₄— | | H | 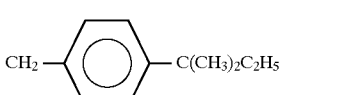 | oil |
| 146 | H | —(CH₂)₄— | | CH₃ | 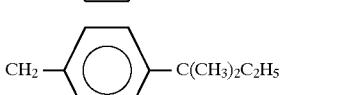 | oil |
| 147 | H | CH₂OCH₃ | OCH₃ | CH₃ | 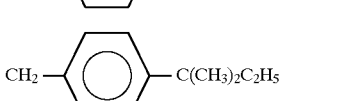 | oil |
| 148 | H | C₂H₅ | Cl | CH₃ | 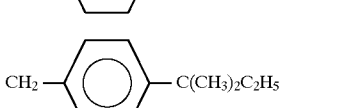 | oil |
| 149 | H | C₂H₅ | Cl | H | 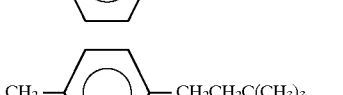 | oil |
| 150 | H | CH₂OCH₃ | OCH₃ | H | 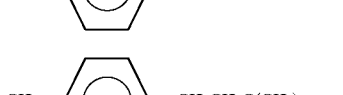 | oil |

-continued
| | | | | | | |
|---|---|---|---|---|---|---|
| 151 | H | —(CH₂)₄— | | H | 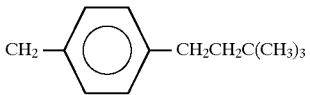 | |
| 152 | H | —(CH₂)₄— | | H | 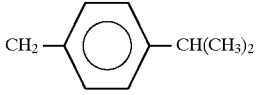 | oil |
| 153 | H | C₂H₅ | Cl | H | 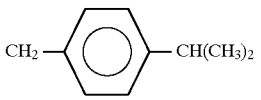 | |
| 154 | H | CH₂OCH₃ | OCH₃ | H | 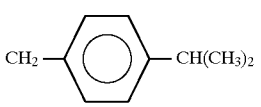 | oil |
| 155 | H | CH₂OCH₃ | OCH₃ | H | 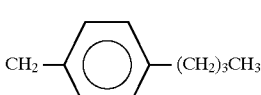 | oil |
| 156 | H | C₂H₅ | Cl | H | 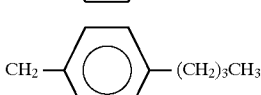 | |
| 157 | H | —(CH₂)₄— | | H | 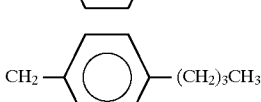 | oil |
| 167 | H | —(CH₂)₄— | | H | 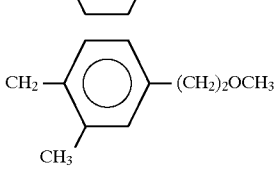 | |
| 168 | H | CH₂OCH₃ | OCH₃ | H | 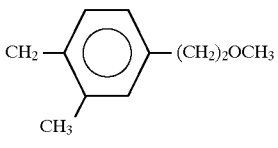 | |
| 169 | H | C₂H₅ | Cl | H | 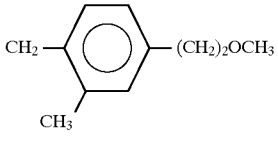 | |
| 170 | H | C₂H₅ | Cl | H | 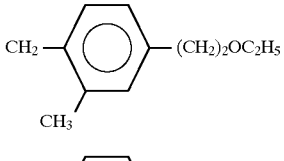 | |
| 171 | H | CH₂OCH₃ | OCH₃ | H | 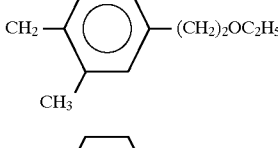 | |
| 172 | H | —(CH₂)₄— | | H | 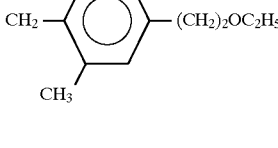 | |

| | | | | | |
|---|---|---|---|---|---|
| 173 | H | —(CH₂)₄— | | H | 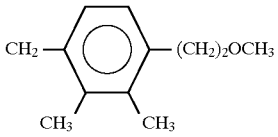 |
| 174 | H | C₂H₅ | Cl | H | 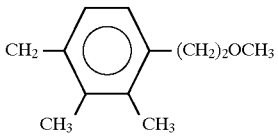 |
| 175 | H | CH₂OCH₃ | OCH₃ | H | 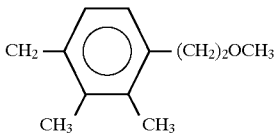 |
| 176 | H | CH₂OCH₃ | OCH₃ | H | 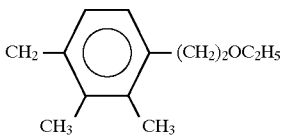 |
| 177 | H | C₂H₅ | Cl | H | 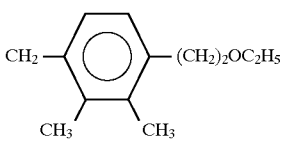 |
| 178 | H | —(CH₂)₄— | | H | 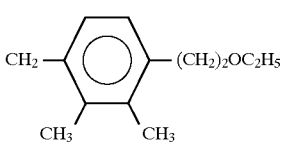 |
| 179 | H | —(CH₂)₄— | | H | 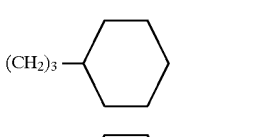 |
| 180 | H | CH₂OCH₃ | OCH₃ | H | 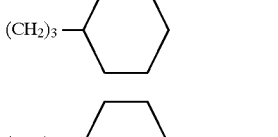 |
| 181 | H | C₂H₅ | Cl | H | 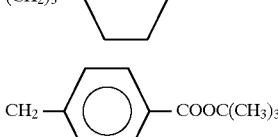 |
| 182 | H | C₂H₅ | Cl | H | 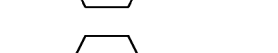 |
| 183 | H | CH₂OCH₃ | OCH₃ | H | 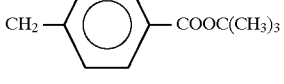 |
| 184 | H | —(CH₂)₄— | | H | 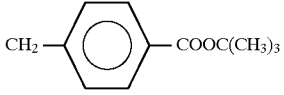 |
| 185 | H | —(CH₂)₄— | | H | 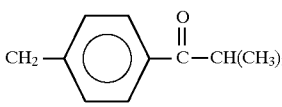 |

-continued

| | | | | | | |
|---|---|---|---|---|---|---|
| 186 | H | CH₂OCH₃ | OCH₃ | H | CH₂–C₆H₄–C(=O)–CH(CH₃)₃ | |
| 187 | H | C₂H₅ | OCH₃ | H | CH₂–C₆H₄–C(=O)–CH(CH₃)₃ | |
| 188 | H | C₂H₅ | OCH₃ | H | CH₂–C₆H₄–C(=O)–CH₂CH₂CH₃ | |
| 189 | H | CH₂OCHH₃ | OCH₃ | H | CH₂–C₆H₄–C(=O)–CH₂CH₂CH₃ | |

Tabelle I

| Example No. | R¹ | R² | R³ | R⁴ | Q | M.p. [°C.] |
|---|---|---|---|---|---|---|
| 186 | H | CH₂OCH₃ | OCH₃ | H | CH₂–C₆H₄–C(=O)–C(CH₃)₃ | |
| 187 | H | C₂H₅ | OCH₃ | H | CH₂–C₆H₄–C(=O)–C(CH₃)₃ | |
| 188 | H | C₂H₅ | OCH₃ | H | CH₂–C₆H₄–C(=O)–CH₂CH₂CH₃ | |
| 189 | H | CH₂OCH₃ | OCH₃ | H | CH₂–C₆H₄–C(=O)–CH₂CH₂CH₃ | |
| 190 | H | (CH₂)₄ | | H | CH₂–C₆H₄–C(=O)–CH₂CH₂CH₃ | |
| 191 | H | (CH₂)₄ | | H | CH₂–C₆H₄–C(=O)–(CH₂)₆CH₃ | |
| 192 | H | CH₂OCH₃ | OCH₃ | H | CH₂–C₆H₄–C(=O)–(CH₂)₆CH₃ | |
| 193 | H | C₂H₅ | OCH₃ | H | CH₂–C₆H₄–C(=O)–(CH₂)₆CH₃ | |

| No. Example | R¹ | R² | R³ | R⁴ | Q | M.p. |
|---|---|---|---|---|---|---|

-continued

| No. Example | R¹ | R² | R³ | R⁴ | Q | M.p. |
|---|---|---|---|---|---|---|
| 190 | H | (CH₂)₄ | | H | CH₂-C₆H₄-C(=O)-CH₂CH₂CH₃ | |
| 191 | H | (CH₂)₄ | | H | CH₂-C₆H₄-C(=O)-(CH₂)₆CH₃ | |
| 192 | H | CH₂OCH₃ | OCH₃ | H | CH₂-C₆H₄-C(=O)-(CH₂)₆CH₃ | |
| 193 | H | C₂H₅ | OCH₃ | H | CH₂-C₆H₄-C(=O)-(CH₂)₆CH₃ | |
| 194 | H | —(CH₂)₃—S | | H | CH₂-C₆H₄-C(CH₃)₃ | 74 |

| Bei- No. Example | R¹ | R² | R³ | R⁴ | Q | M.p. |
|---|---|---|---|---|---|---|
| 195 | H | —(CH₂)₃—S | | H | CH₂-C₆H₄-(CH₂)₃CH₃ | |
| 196 | H | —(CH₂)₃—S | | H | CH₂-C₆H₄-CH(CH₃)₂ | |
| 197 | H | —(CH₂)₃—S | | C₂H₅ | C₆H₄-O-C₆H₄-Cl | |
| 198 | H | —(CH₂)₃—S | | H | CH₂-C₆H₄-C₆H₅ | 55 |
| 199 | H | —(CH₂)₄ | | H | CH₂-C₆H₄-CF₃ | |
| 200 | H | Cl | OCH₃ | CH₃ | (CH₂)₃CH₃ | oil |
| 201 | H | Cl | OCH₃ | C₂H₅ | (CH₂)₆CH₃ | oil |
| 202 | H | CH₂OCH₃ | OCH₃ | H | CH₂O(CH₂)₂OCH₃ | oil |
| 203 | H | O(CH₂)₂O(CH₂)₇CH3 | OCH₃ | H | CH₂O(CH₂)₂OCH₃ | oil |
| 204 | H | CH₂OCH₃ | OCH₃ | CH₃ | (CH₂)₂CH=C(CH₃)CH₂CH₂CH=C(CH₂)₂ | oil |
| 205 | H | O(CH₂)O(CH₂)₉CH₃ | OCH₃ | H | CH₂O(CH₂)₉CH₃ | 32° C. |
| 206 | H | —(CH₂)₄— | | H | CH₂O₂C(CH₂)₂CH₃ | oil |
| 207 | H | —(CH₂)₄— | | H | CH₂O₂C(CH₂)₃CH₃ | oil |

| No. Example | R¹ | R² | R³ | R⁴ | Q | M.p. |
|---|---|---|---|---|---|---|
| 208 | H | Cl | OCH₃ | C₂H₅ | (CH₂)₆CH₃ | oil |
| 209 | H | C₂H₅ | Cl | CH₃ | (CH₂)₇CH₃ | oil |

-continued
| No. | | | | | | |
|---|---|---|---|---|---|---|
| 210 | H | CH₂OCH₃ | OCH₃ | H | 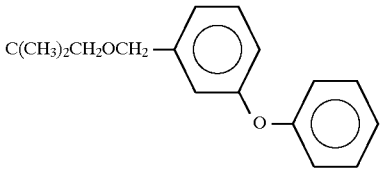 | oil |
| 211 | H | —(CH₂)₄— | | H | 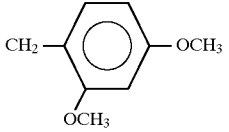 | 77–80° C. |
| 212 | H | —(CH₂)₄— | | H | 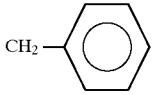 | oil |
| 213 | H | —(CH₂)₅— | | H | 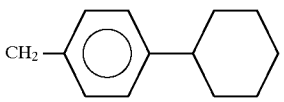 | oil |
| 214 | H | Cl | OCH₃ | H | 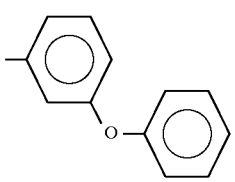 | oil |
| 215 | H | O(CH₂)OCH₂ | OCH₃ | H | 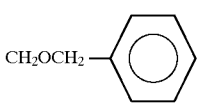 | oil |
| 216 | H | C₂H₅ | Cl | H | 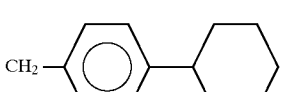 | oil |
| 217 | H | CH₂OCH₃ | OCH₃ | H | 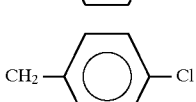 | oil |
| 218 | H | C₂H₅ | Cl | H | 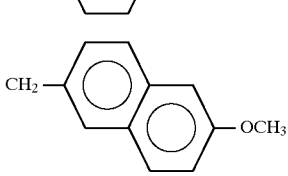 | 68° C. |
| 219 | H | OCH₂CH₂ | OCH₃ | H | 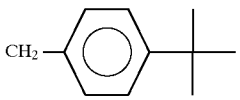 | 69–73° C. |
| 220 | H | —(CH₂)₃— | | H | 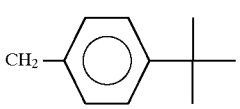 | oil |
| 221 | H | —(CH₂)₅— | | H | 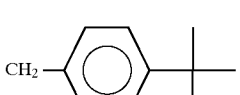 | oil |
| 222 | H | —(CH₂)₄— | | H | 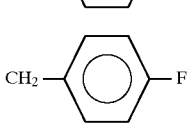 | 50° C. |

-continued

| | | | | | Q | M.p. |
|---|---|---|---|---|---|---|
| 223 | H | —(CH$_2$)$_4$— | | H | 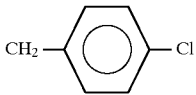 CH$_2$—◯—Cl | 49° C. |
| 224 | H | —(CH$_2$)$_4$— | | H | 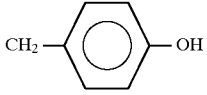 CH$_2$—◯—OH | Oil |
| 225 | H | —(CH$_2$)$_4$— | | H |  CH$_2$—◯—Br | Oil |
| 226 | H | —(CH$_2$)$_4$— | | CH$_3$ | 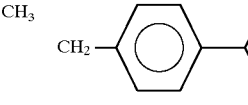 CH$_2$—◯—⬡ | 82° C. |
| 227 | H | CH$_2$OCH$_3$ | OCH$_3$ | CH$_3$ | 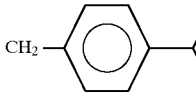 CH$_2$—◯—⬡ | Oil |
| 228 | H | —(CH$_2$)$_4$— | | H | 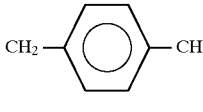 CH$_2$—◯—CH(CH$_3$)CH$_2$CH$_3$ | Oil |
| 229 | H | CH$_2$OCH$_3$ | OCH$_3$ | H | 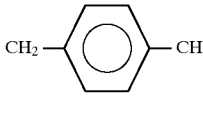 CH$_2$—◯—CH(CH$_3$)CH$_2$CH$_3$ | Oil |
| 230 | H | —(CH$_2$)$_4$— | | CH$_3$ | 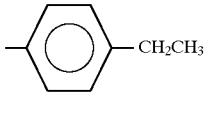 —◯—CH$_2$CH$_3$ | Oil |
| 231 | H | CH$_2$OCH$_3$ | OCH$_3$ | CH$_3$ | 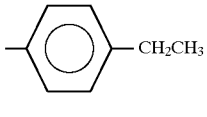 —◯—CH$_2$CH$_3$ | Oil |
| 232 | H | C$_2$H$_5$ | Cl | CH$_3$ | 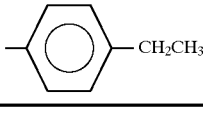 —◯—CH$_2$CH$_3$ | Oil |

| Example No. | R$^1$ | R$^2$ | R$^3$ | R$^4$ | Q | M.p. |
|---|---|---|---|---|---|---|
| 233 | H | —(CH)$_4$— | | CH$_3$ | 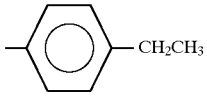 —◯—CH$_2$CH$_3$ | Oil |
| 234 | H | —(CH$_2$)$_4$— | | CH$_3$ | 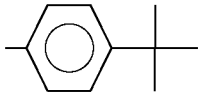 —◯—C(CH$_3$)$_3$ | 92° C. |
| 235 | H | CH$_2$OCH$_3$ | OCH$_3$ | CH$_3$ | 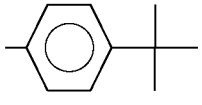 —◯—C(CH$_3$)$_3$ | Oil |
| 236 | H | —(CH$_2$)$_4$— | | CH$_3$ | 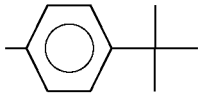 —◯—C(CH$_3$)$_3$ | Oil |

-continued
| | | | | | | |
|---|---|---|---|---|---|---|
| 237 | H | C₂H₅ | Cl | CH₃ | 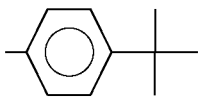 | Oil |
| 238 | H | —(CH₂)₄— | | CH₃ | 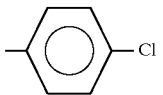 | Oil |
| 239 | H | CH₂OCH₃ | OCH₃ | CH₃ | 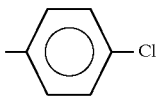 | Oil |
| 240 | H | —(CH)₄— | | CH₃ | 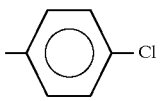 | Oil |
| 241 | H | —C₂H₅ | Cl | CH₃ | 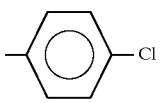 | Oil |
| 242 | H | —(CH₂)₄— | | CH₃ | 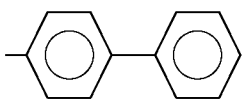 | Oil |
| 243 | H | CH₂OCH₃ | OCH₃ | CH₃ | 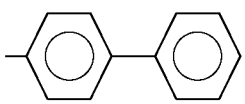 | Oil |
| 244 | H | —(CH)₄— | | CH₃ | 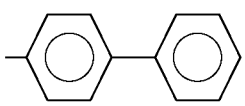 | Oil |
| 245 | H | C₂H₅ | Cl | CH₃ | 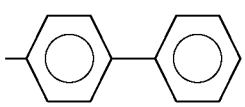 | Oil |
| 246 | H | C₂H₅ | Cl | H | 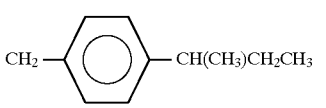 | Oil |
| 247 | H | C₂H₅ | Cl | H | 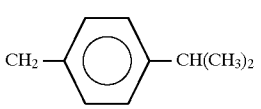 | Oil |
| 248 | H | C₂H₅ | Cl | H | 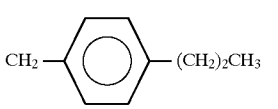 | Oil |
| 249 | H | C₂H₅ | Cl | H | 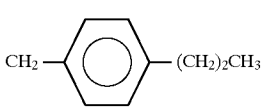 | Oil |
| 250 | H | C₂H₅ | Cl | H | 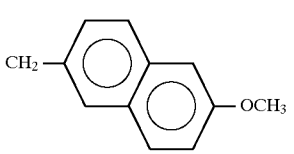 | 68° C. |

-continued
| No. Example | R¹ | R² | | R³ | R⁴ | Q | M.p. |
|---|---|---|---|---|---|---|---|
| 251 | H | C₂H₅ | | Cl | C₂H₅ | 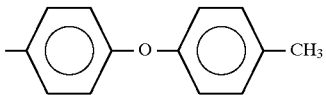 | Oil |
| 252 | H | | —(CH₂)₄— | | CH₃ | 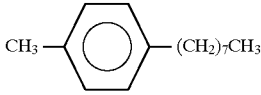 | Oil |
| 253 | H | CH₂OCH₃ | | OCH₃ | CH₃ | 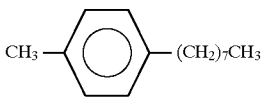 | Oil |
| 254 | H | C₂H₅ | | Cl | CH₃ | 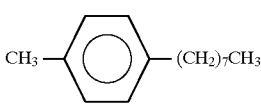 | Oil |
| 255 | H | | —(CH₂)₄— | | H | 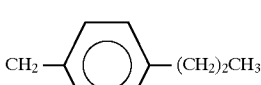 | Oil |
| 256 | H | CH₂OCH₃ | | OCH₃ | H | 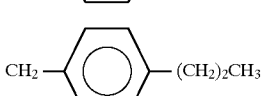 | Oil |
| 257 | H | C₂H₅ | | Cl | H | 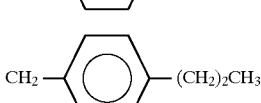 | Oil |
| 258 | H | | —(CH₂)₄— | | H |  | Oil |
| 259 | H | | —(CH₂)₄— | | H | 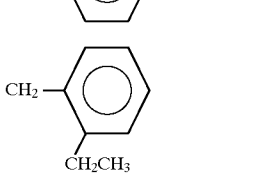 | oil |
| 260 | H | CH₂OCH₃ | | OCH₃ | H | 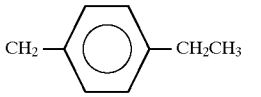 | oil |
| 261 | H | CH₂OCH₃ | | OCH₃ | H |  | oil |
| 262 | H | | —(CH₂)₄— | | H | 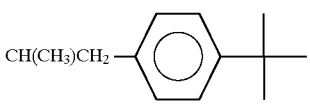 | oil |
| 263 | H | CH₂OCH₃ | | OCH₃ | H | 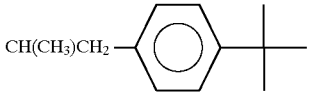 | oil |
| 264 | H | | —(CH₂)— | | H | 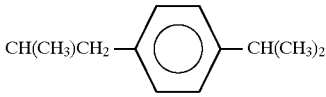 | oil |

-continued
| 265 | H | CH₂OCH₃ | OCH₃ | H | 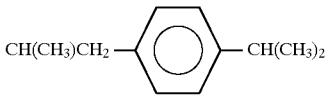 | oil |
| --- | --- | --- | --- | --- | --- | --- |
| 266 | H | —(CH₂)₄— | | H | 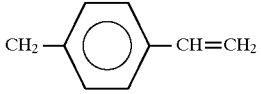 | oil |
| 267 | H | CH₂OCH₃ | OCH₃ | H | 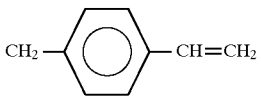 | Oil |
| 268 | H | C₂H₅ | Cl | H | 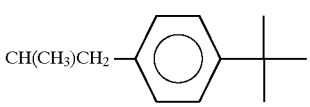 | Oil |
| 269 | H | —(CH₂)₄— | | H | 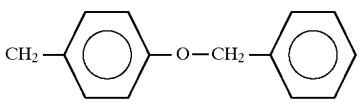 | Oil |
| 270 | H | CH₂OCH₃ | OCH₃ | H | 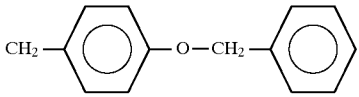 | Oil |
| 271 | H | C₂H₅ | Cl | H | 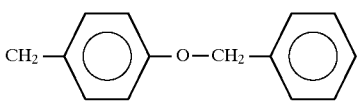 | Oil |
| 272 | H | —(CH₂)₄— | | H | 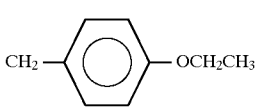 | |
| 273 | H | CH₂OCH₃ | OCH₃ | H | 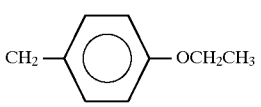 | |
| 274 | H | C₂H₅ | Cl | H | 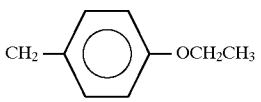 | |
| 275 | H | —(CH₂)₄— | | H | 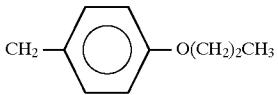 | Oil |
| 276 | H | CH₂OCH₃ | OCH₃ | H | 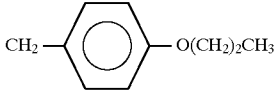 | Oil |
| 277 | H | C₂H₅ | Cl | H | 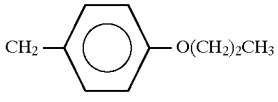 | Oil |
| 278 | H | —(CH₂)₄— | | H | 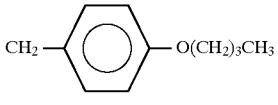 | |
| 279 | H | CH₂OCH₃ | OCH₃ | H | 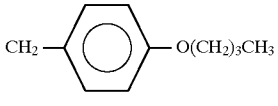 | |

-continued
| Example No. | $R^1$ | $R^2$ | $R^3$ | $R^4$ | Q | M.p. |
|---|---|---|---|---|---|---|
| 280 | H | $C_2H_5$ | Cl | H | 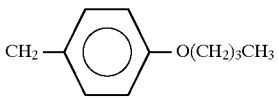 | |
| 281 | H | $-(CH_2)_4-$ | | H | 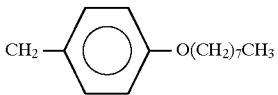 | |
| 282 | H | $CH_2OCH_3$ | $OCH_3$ | H | 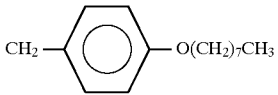 | |
| 283 | H | $C_2H_5$ | Cl | H | 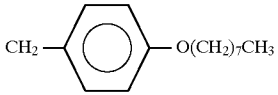 | |
| 284 | H | $-(CH_2)_4-$ | | H | 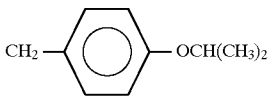 | Oil |
| 285 | H | $CH_2OCH_3$ | $OCH_3$ | H | 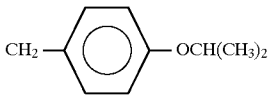 | Oil |
| 286 | H | $C_2H_5$ | Cl | H | 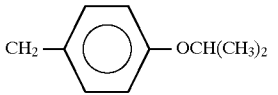 | |
| 287 | H | $-(CH_2)_4-$ | | H | 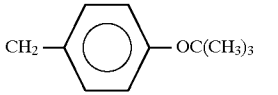 | |
| 288 | H | $CH_2OCH_3$ | $OCH_3$ | H | 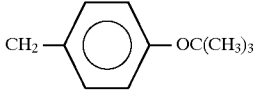 | |
| 289 | H | $C_2H_5$ | Cl | H | 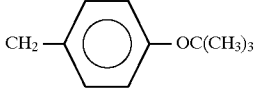 | |
| 290 | H | $-(CH_2)_4-$ | | H | 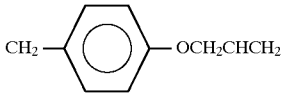 | Oil |
| 291 | H | $CH_2CH_3$ | $OCH_3$ | H | 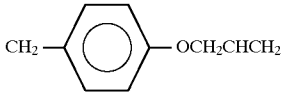 | |
| 292 | H | $C_2H_5$ | Cl | H | 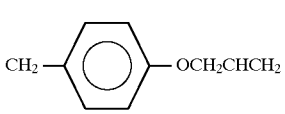 | |
| 293 | H | $-(CH_2)_4-$ | | H | 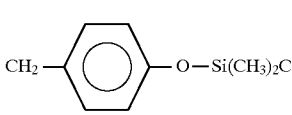 | Oil |

-continued

| | | | | | | |
|---|---|---|---|---|---|---|
| 294 | H | CH$_2$OCH$_3$ | OCH$_3$ | H | CH$_2$—⟨C$_6$H$_4$⟩—O—Si(CH$_3$)$_2$C(CH$_3$)$_3$ | |
| 295 | H | C$_2$H$_5$ | Cl | H | CH$_2$—⟨C$_6$H$_4$⟩—O—Si(CH$_3$)$_2$C(CH$_3$)$_3$ | |
| 296 | H | —(CH$_2$)$_4$— | | H | CH$_2$—⟨C$_6$H$_4$⟩—Si(CH$_3$)$_2$CH$_2$Cl | Oil |
| 297 | H | CH$_2$OCH$_3$ | OCH$_3$ | H | CH$_2$—⟨C$_6$H$_4$⟩—Si(CH$_3$)$_2$CH$_2$Cl | |
| 298 | H | C$_2$H$_5$ | Cl | H | CH$_2$—⟨C$_6$H$_4$⟩—Si(CH$_3$)$_2$CH$_2$Cl | |
| 299 | H | —(CH$_2$)$_4$— | | H | CH$_2$—⟨C$_6$H$_4$⟩—Si(CH$_3$)$_3$ | Oil |
| 300 | H | CH$_2$OCH$_3$ | OCH$_3$ | H | CH$_2$—⟨C$_6$H$_4$⟩—Si(CH$_3$)$_3$ | Oil |
| 301 | H | C$_2$H$_5$ | Cl | H | CH$_2$—⟨C$_6$H$_4$⟩—Si(CH$_3$)$_3$ | Oil |
| 302 | H | —(CH$_2$)$_4$— | | H | CH$_2$—⟨C$_6$H$_4$⟩—Si(CH$_3$)$_2$(CH$_2$)$_7$CH$_3$ | Oil |
| 303 | H | CH$_2$OCH$_3$ | OCH$_3$ | H | CH$_2$—⟨C$_6$H$_4$⟩—Si(CH$_3$)$_2$(CH$_2$)$_7$CH$_3$ | Oil |
| 304 | H | C$_2$H$_5$ | Cl | H | CH$_2$—⟨C$_6$H$_4$⟩—Si(CH$_3$)$_2$(CH$_2$)$_7$CH$_3$ | |
| 305 | H | —(CH$_2$)$_4$— | | H | CH$_2$—⟨C$_6$H$_4$⟩—Si(C$_2$H$_5$)$_3$ | Oil |
| 306 | H | CH$_2$OCH$_3$ | OCH$_3$ | H | CH$_2$—⟨C$_6$H$_4$⟩—Si(C$_2$H$_5$)$_3$ | Oil |
| 307 | H | C$_2$H$_5$ | Cl | H | CH$_2$—⟨C$_6$H$_4$⟩—Si(C$_2$H$_5$)$_3$ | |
| 308 | H | —(CH$_2$)$_4$— | | H | CH$_2$—⟨C$_6$H$_4$⟩—Si(CH$_3$)$_2$—⟨C$_6$H$_5$⟩ | |

-continued
| | | | | | | |
|---|---|---|---|---|---|---|
| 309 | H | CH₂OCH₃ | | OCH₃ | H |  |
| 310 | H | C₂H₅ | | Cl | H | 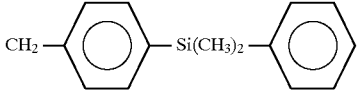 |
| 311 | H | —(CH₂)₄— | | | H | 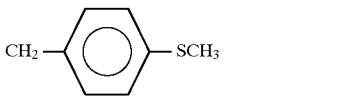 Oil |
| 312 | H | CH₂OCH₃ | | OCH₃ | H | 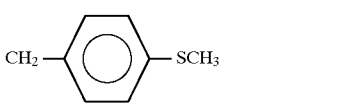 Oil |
| 313 | H | C₂H₅ | | Cl | H | 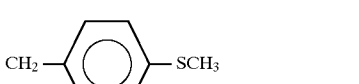 Oil |
| 314 | H | —(CH₂)₄— | | | H | 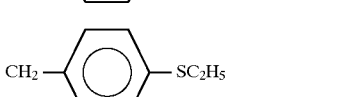 |
| 315 | H | CH₂OCH₃ | | OCH₃ | H | 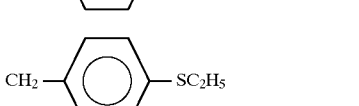 |
| 316 | H | C₂H₅ | | Cl | H |  |
| 317 | H | —(CH₂)₄— | | | H |  |
| 318 | H | CH₂OCH₃ | | OCH₃ | H |  |
| 319 | H | C₂H₅ | | Cl | H | 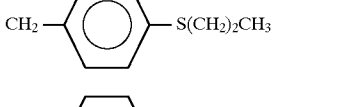 |
| 320 | H | —(CH₂)₄— | | | H | 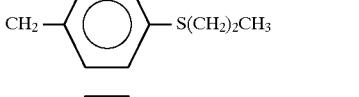 Oil |
| 321 | H | CH₂OCH₃ | | OCH₃ | H | 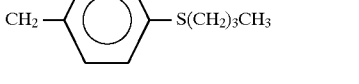 Oil |
| 322 | H | C₂H₅ | | Cl | H | 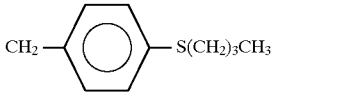 Oil |
| 323 | H | —(CH₂)₄— | | | H | 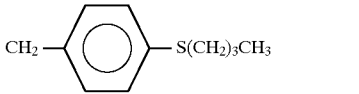 |

-continued

| | | | | | |
|---|---|---|---|---|---|
| 324 | H | CH₂OCH₃ | OCH₃ | H | CH₂—⟨C₆H₄⟩—S(CH₂)₄CH₃ |
| 325 | H | C₂H₅ | Cl | H | CH₂—⟨C₆H₄⟩—S(CH₂)₄CH₃ |
| 326 | H | —(CH₂)₄— | | H | CH₂—⟨C₆H₄⟩—S(CH₂)₅CH₃ |
| 327 | H | CH₂OCH₃ | OCH₃ | H | CH₂—⟨C₆H₄⟩—S(CH₂)₅CH₃ |
| 328 | H | C₂H₅ | Cl | H | CH₂—⟨C₆H₄⟩—S(CH₂)₅CH₃ |
| 329 | H | —(CH₂)₄— | | H | CH₂—⟨C₆H₄⟩—S(CH₂)₆CH₃ |
| 330 | H | CH₂OCH₃ | OCH₃ | H | CH₂—⟨C₆H₄⟩—S(CH₂)₆CH₃ |
| 331 | H | C₂H₅ | Cl | H | CH₂—⟨C₆H₄⟩—S(CH₂)₆CH₃ |
| 332 | H | —(CH₂)₄— | | H | CH₂—⟨C₆H₄⟩—S(CH₂)₇CH₃ |
| 333 | H | CH₂OCH₃ | OCH₃ | H | CH₂—⟨C₆H₄⟩—S(CH₂)₇CH₃ |
| 334 | H | C₂H₅ | Cl | H | CH₂—⟨C₆H₄⟩—S(CH₂)₇CH₃ |
| 335 | H | —(CH₂)₄— | | H | CH₂—⟨C₆H₄⟩—S—C(CH₃)₃ |
| 336 | H | CH₂OCH₃ | OCH₃ | H | CH₂—⟨C₆H₄⟩—S—C(CH₃)₃ |
| 337 | H | C₂H₅ | Cl | H | CH₂—⟨C₆H₄⟩—S—C(CH₃)₃ |
| 338 | H | —(CH₂)₄— | | H | CH₂—⟨C₆H₄⟩—S—CH₂—⟨C₆H₅⟩ |

-continued

| | | | | | |
|---|---|---|---|---|---|
| 339 | H | CH₂OCH₃ | OCH₃ | H | CH₂–⟨C₆H₄⟩–S–CH₂–⟨C₆H₅⟩ |
| 340 | H | C₂H₅ | Cl | H | CH₂–⟨C₆H₄⟩–S–CH₂–⟨C₆H₅⟩ |
| 341 | H | –(CH₂)₄– | | H | CH₂–⟨C₆H₄⟩–SCH₂–⟨C₆H₄⟩–C(CH₃)₃ |
| 342 | H | CH₂OCH₃ | OCH₃ | H | CH₂–⟨C₆H₄⟩–SCH₂–⟨C₆H₄⟩–C(CH₃)₃ |
| 343 | H | C₂H₅ | Cl | H | CH₂–⟨C₆H₅⟩   SCH₂–⟨C₆H₄⟩–C(CH₃)₃ |
| 344 | H | –(CH₂)₄– | | H | CH₂–⟨C₆H₄⟩–S–CH₂–⟨C₆H₄⟩–OCH₃ |
| 345 | H | CH₂OCH₃ | OCH₃ | H | CH₂–⟨C₆H₄⟩–S–CH₂–⟨C₆H₄⟩–OCH₃ |
| 346 | H | C₂H₅ | Cl | H | CH₂–⟨C₆H₄⟩–S–CH₂–⟨C₆H₄⟩–OCH₃ |
| 347 | H | –(CH₂)₄– | | H | CH₂–⟨C₆H₄⟩–S–CH₂–⟨C₆H₄⟩–Cl |
| 348 | H | CH₂OCH₃ | OCH₃ | H | CH₂–⟨C₆H₄⟩–S–CH₂–⟨C₆H₄⟩–Cl |
| 349 | H | C₂H₅ | Cl | H | CH₂–⟨C₆H₄⟩–S–CH₂–⟨C₆H₄⟩–Cl |
| 350 | H | –(CH₂)₄– | | H | CH₂–⟨C₆H₄⟩–S–⟨C₆H₅⟩ |
| 351 | H | CH₂OCH₃ | OCH₃ | H | CH₂–⟨C₆H₄⟩–S–⟨C₆H₅⟩ |
| 352 | H | C₂H₅ | Cl | H | CH₂–⟨C₆H₄⟩–S–⟨C₆H₅⟩ |
| 353 | H | –(CH₂)₄– | | H | CH₂–⟨C₆H₄⟩–S–⟨C₆H₄⟩–Cl |

-continued
| 354 | H | CH₂OCH₃ | OCH₃ | H | 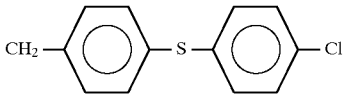 |
| 355 | H | C₂H₅ | Cl | H | 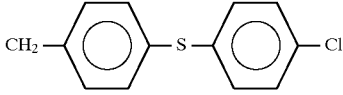 |
| 356 | H | —(CH₂)₄— | | H | 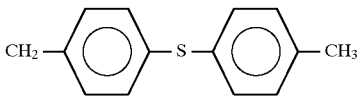 |
| 357 | H | CH₂OCH₃ | OCH₃ | H | 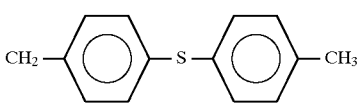 |
| 358 | H | C₂H₅ | Cl | H | 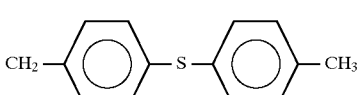 |
| 359 | H | —(CH₂)₄— | | H | 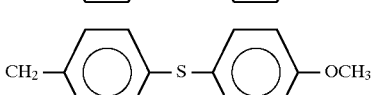 |
| 360 | H | CH₂OCH₃ | OCH₃ | H | 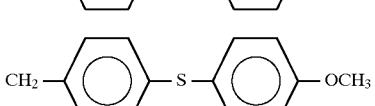 |
| 361 | H | C₂H₅ | Cl | H | 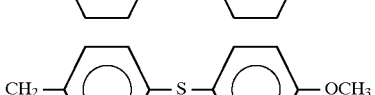 |
| 362 | H | —(CH₂)₄— | | H | 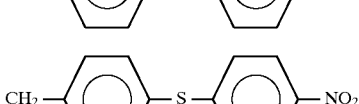 |
| 363 | H | CH₂OCH₃ | OCH₃ | H |  |
| 364 | H | C₂H₅ | Cl | H |  |
| 365 | H | —(CH₂)₄— | | CH₃ | 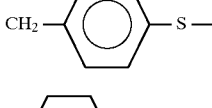 |
| 366 | H | CH₂OCH₃ | OCH₃ | CH₃ | 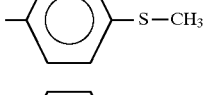 |
| 367 | H | C₂H₅ | Cl | CH₃ | 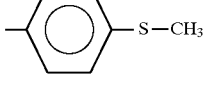 |
| 368 | H | —(CH₂)₄— | | CH₃ | 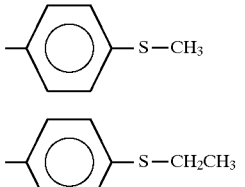 |

-continued

| | | | | | Q | M.p. |
|---|---|---|---|---|---|---|
| 369 | H | CH$_2$OCH$_3$ | OCH$_3$ | CH$_3$ | 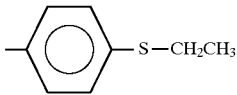 —C$_6$H$_4$—S—CH$_2$CH$_3$ | |
| 370 | H | C$_2$H$_5$ | Cl | CH$_3$ | 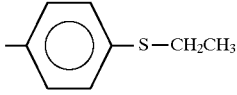 —C$_6$H$_4$—S—CH$_2$CH$_3$ | |
| 371 | H | —(CH$_2$)$_4$— | | CH$_3$ | 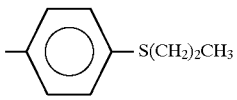 —C$_6$H$_4$—S(CH$_2$)$_2$CH$_3$ | |
| 372 | H | CH$_2$OCH$_3$ | OCH$_3$ | CH$_3$ | 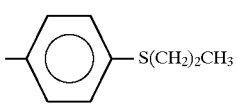 —C$_6$H$_4$—S(CH$_2$)$_2$CH$_3$ | |
| 373 | H | C$_2$H$_5$ | Cl | CH$_3$ | 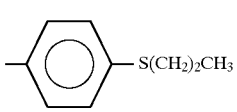 —C$_6$H$_4$—S(CH$_2$)$_2$CH$_3$ | |

| Bei-Example No. | R$^1$ | R$^2$ | R$^3$ | R$^4$ | Q | M.p. |
|---|---|---|---|---|---|---|
| 374 | H | —(CH$_2$)$_4$— | | CH$_3$ | 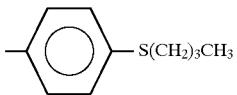 —C$_6$H$_4$—S(CH$_2$)$_3$CH$_3$ | |
| 375 | H | CH$_2$OCH$_3$ | OCH$_3$ | CH$_3$ | 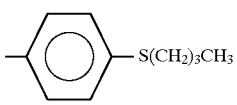 —C$_6$H$_4$—S(CH$_2$)$_3$CH$_3$ | |
| 376 | H | C$_2$H$_5$ | Cl | CH$_3$ | 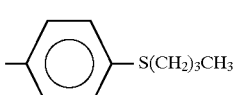 —C$_6$H$_4$—S(CH$_2$)$_3$CH$_3$ | |
| 377 | H | —(CH$_2$)$_4$— | | CH$_3$ | 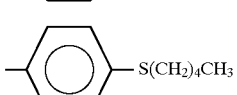 —C$_6$H$_4$—S(CH$_2$)$_4$CH$_3$ | |
| 378 | H | CH$_2$OCH$_3$ | OCH$_3$ | CH$_3$ | 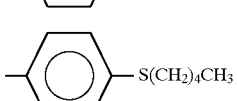 —C$_6$H$_4$—S(CH$_2$)$_4$CH$_3$ | |
| 379 | H | C$_2$H$_5$ | Cl | CH$_3$ | 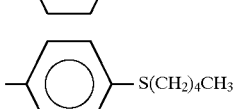 —C$_6$H$_4$—S(CH$_2$)$_4$CH$_3$ | |
| 380 | H | —(CH$_2$)$_4$— | | CH$_3$ | 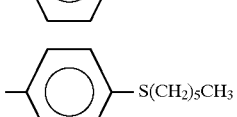 —C$_6$H$_4$—S(CH$_2$)$_5$CH$_3$ | |
| 381 | H | CH$_2$OCH$_3$ | OCH$_3$ | CH$_3$ |  —C$_6$H$_4$—S(CH$_2$)$_5$CH$_3$ | |
| 382 | H | C$_2$H$_5$ | Cl | CH$_3$ |  —C$_6$H$_4$—S(CH$_2$)$_5$CH$_3$ | |

-continued
| Example No. | R¹ | R² | R³ | R⁴ | Q | M.p. |
|---|---|---|---|---|---|---|
| 383 | H | —(CH₂)₄— | | CH₃ | 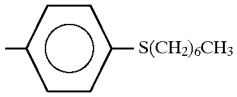 | |
| 384 | H | CH₂OCH₃ | OCH₃ | CH₃ | 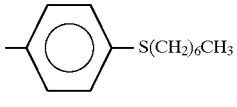 | |
| 385 | H | C₂H₅ | Cl | CH₃ | 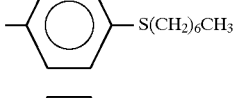 | |
| 386 | H | —(CH₂)₄— | | CH₃ | 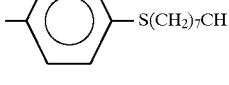 | |
| 387 | H | CH₂OCH₃ | OCH₃ | CH₃ | 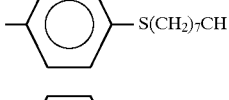 | |
| 388 | H | C₂H₅ | Cl | CH₃ |  | |
| 389 | H | —(CH₂)₄— | | CH₃ | 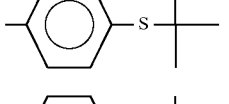 | |
| 390 | H | CH₂OCH₃ | OCH₃ | CH₃ |  | |
| 391 | H | C₂H₅ | Cl | CH₃ |  | |
| 392 | H | —(CH₂)₄— | | CH₃ | 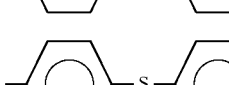 | |
| 393 | H | CH₂OCH₃ | OCH₃ | CH₃ | 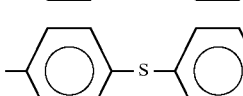 | |
| 394 | H | C₂H₅ | Cl | CH₃ | 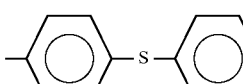 | |
| 395 | H | —(CH₂)₄— | | CH₃ | 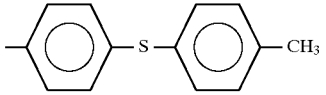 | |
| 396 | H | CH₂OCH₃ | OCH₃ | CH₃ |  | |

-continued
| 397 | H | C₂H₅ | Cl | CH₃ | 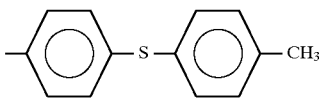 |
| 398 | H | —(CH₂)₄— | | CH₃ | 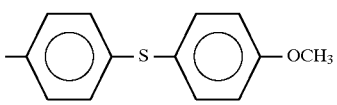 |
| 399 | H | CH₂OCH₃ | OCH₃ | CH₃ | 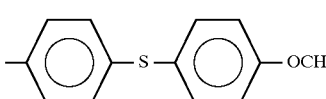 |
| 400 | H | C₂H₅ | Cl | CH₃ | 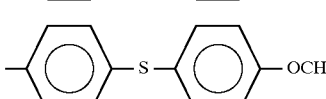 |
| 401 | H | —(CH₂)₄— | | CH₃ | 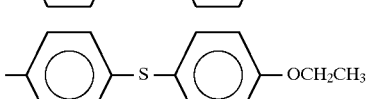 |
| 402 | H | CH₂OCH₃ | OCH₃ | CH₃ | 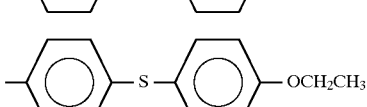 |
| 403 | H | C₂H₅ | Cl | CH₃ | 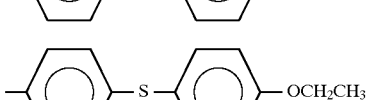 |
| 404 | H | —(CH₂)₄— | | CH₃ | 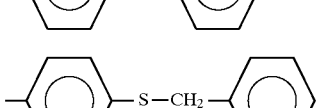 |
| 405 | H | CH₂OCH₃ | OCH₃ | CH₃ |  |
| 406 | H | C₂H₅ | Cl | CH₃ | 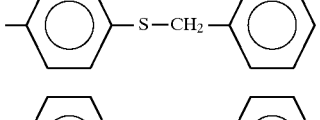 |
| 407 | H | —(CH₂)₄— | | CH₃ | 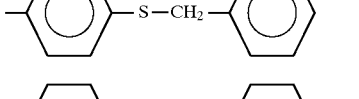 |
| 408 | H | CH₂OCH₃ | OCH₃ | CH₃ | 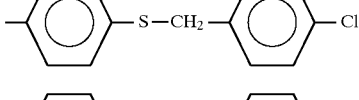 |
| 409 | H | C₂H₅ | Cl | CH₃ | 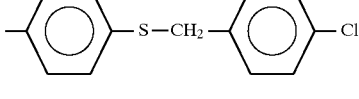 |
| 410 | H | —(CH₂)₄— | | CH₃ | 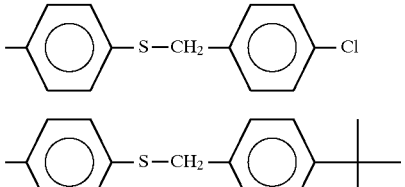 |
| 411 | H | CH₂OCH₃ | OCH₃ | CH₃ | 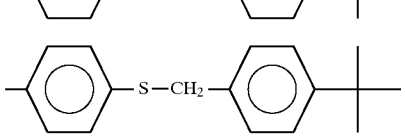 |

-continued
| | | | | | | |
|---|---|---|---|---|---|---|
| 412 | H | C₂H₅ | Cl | CH₃ | 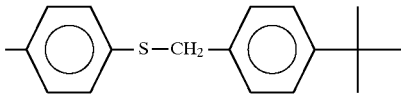 | |
| 413 | H | —(CH₂)₄— | | H |  | |
| 414 | H | CH₂OCH₃ | OCH₃ | H | 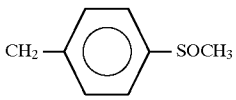 | |
| 415 | H | C₂H₅ | Cl | H | 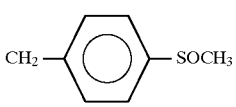 | |
| 416 | H | —(CH₂)₄— | | H | 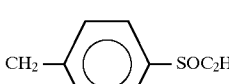 | |
| 417 | H | CH₂OCH₃ | OCH₃ | H | 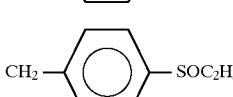 | |
| 418 | H | C₂H₅ | Cl | H | 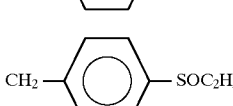 | |
| 419 | H | —(CH₂)₄— | | H | 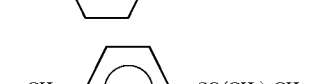 | |
| 420 | H | CH₂OCH₃ | OCH₃ | H |  | |
| 421 | H | C₂H₅ | Cl | H |  | |
| 422 | H | —(CH₂)₄— | | H |  | Oil |
| 423 | H | CH₂OCH₃ | OCH₃ | H | 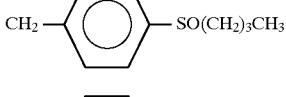 | |
| 424 | H | C₂H₅ | Cl | H | 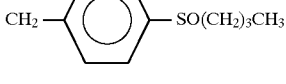 | |
| 425 | H | —(CH₂)₄— | | H | 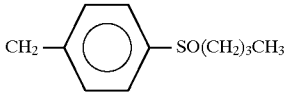 | |
| 426 | H | CH₂OCH₃ | OCH₃ | H | 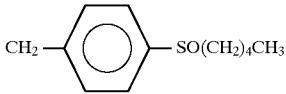 | |

-continued
| | | | | | |
|---|---|---|---|---|---|
| 427 | H | C₂H₅ | Cl | H | 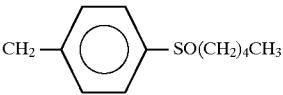 |
| 428 | H | —(CH₂)₄— | | H | 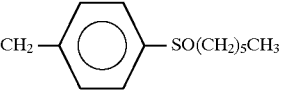 |
| 429 | H | CH₂OCH₃ | OCH₃ | H | 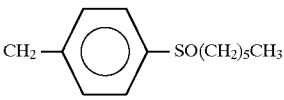 |
| 430 | H | C₂H₅ | Cl | H | 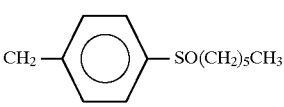 |
| 431 | H | —(CH₂)₄— | | H | 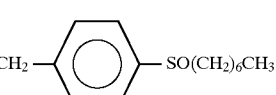 |
| 432 | H | CH₂OCH₃ | OCH₃ | H | 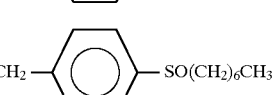 |
| 433 | H | C₂H₅ | Cl | H | 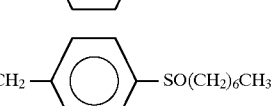 |
| 434 | H | —(CH₂)₄— | | H | 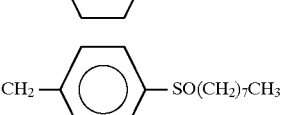 |
| 435 | H | CH₂OCH₃ | OCH₃ | H |  |
| 436 | H | C₂H₅ | Cl | H |  |
| 437 | H | —(CH₂)₄— | | H | 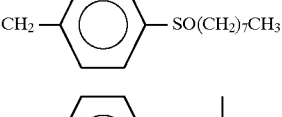 |
| 438 | H | CH₂OCH₃ | OCH₃ | H | 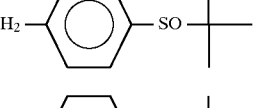 |
| 439 | H | C₂H₅ | Cl | H | 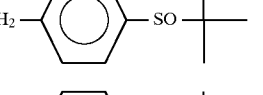 |
| 440 | H | —(CH₂)₄— | | H | 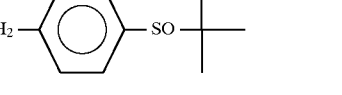 |
| 441 | H | CH₂OCH₃ | OCH₃ | H | 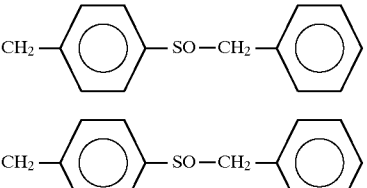 |

-continued
| 442 | H | C₂H₅ | | Cl | H | 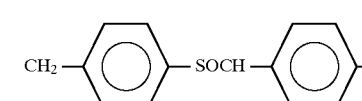 |
| 443 | H | | —(CH₂)₄— | | H | 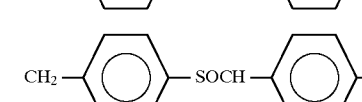 |
| 444 | H | CH₂OCH₃ | | OCH₃ | H | 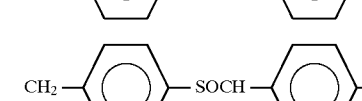 |
| 445 | H | C₂H₅ | | Cl | H | 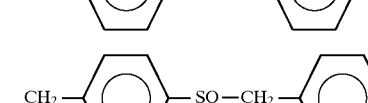 |
| 446 | H | | —(CH₂)₄— | | H | 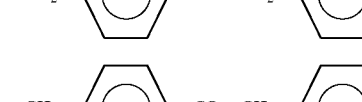 |
| 447 | H | CH₂OCH₃ | | OCH₃ | H | 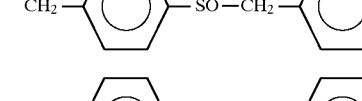 |
| 448 | H | C₂H₅ | | Cl | H | 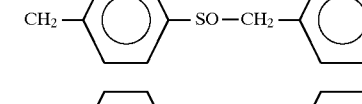 |
| 449 | H | | —(CH₂)₄— | | H | 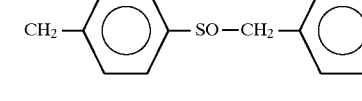 |
| 450 | H | CH₂OCH₃ | | OCH₃ | H | 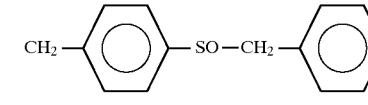 |
| 451 | H | C₂H₅ | | Cl | H | 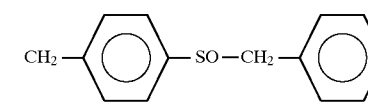 |
| 452 | H | | —(CH₂)₄— | | H | 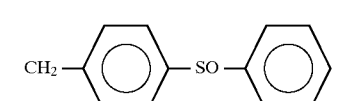 |
| 453 | H | CH₂OCH₃ | | OCH₃ | H | 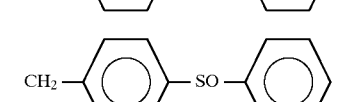 |
| 454 | H | C₂H₅ | | Cl | H | 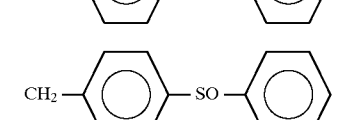 |
| 455 | H | | —(CH₂)₄— | | H |  |
| 456 | H | CH₂OCH₃ | | OCH₃ | H | |

-continued

| | | | | | |
|---|---|---|---|---|---|
| 457 | H | C₂H₅ | Cl | H | CH₂–C₆H₄–SO–C₆H₄–Cl |
| 458 | H | —(CH₂)₄— | | H | CH₂–C₆H₄–SO–C₆H₄–CH₃ |
| 459 | H | CH₂OCH₃ | OCH₃ | H | CH₂–C₆H₄–SO–C₆H₄–CH₃ |
| 460 | H | C₂H₅ | Cl | H | CH₂–C₆H₄–SO–C₆H₄–CH₃ |
| 461 | H | —(CH₂)₄— | | H | CH₂–C₆H₄–SO–C₆H₄–OCH₃ |
| 462 | H | CH₂OCH₃ | OCH₃ | H | CH₂–C₆H₄–SO–C₆H₄–OCH₃ |
| 463 | H | C₂H₅ | Cl | H | CH₂–C₆H₄–SO–C₆H₄–OCH₃ |
| 464 | H | —(CH₂)₄— | | H | CH₂–C₆H₄–SO–C₆H₄–NO₂ |
| 465 | H | CH₂OCH₃ | OCH₃ | H | CH₂–C₆H₄–SO–C₆H₄–NO₂ |
| 466 | H | C₂H₅ | Cl | H | CH₂–C₆H₄–SO–C₆H₄–NO₂ |
| 467 | H | —(CH₂)₄— | | CH₃ | C₆H₄–SO–CH₃ |
| 468 | H | CH₂OCH₃ | OCH₃ | CH₃ | C₆H₄–SO–CH₃ |
| 469 | H | C₂H₅ | Cl | CH₃ | C₆H₄–SO–CH₃ |
| 470 | H | —(CH₂)₄— | | CH₃ | C₆H₄–SO–CH₂CH₃ |
| 471 | H | CH₂OCH₃ | OCH₃ | CH₃ | C₆H₄–SO–CH₂CH₃ |

-continued
| | | | | | |
|---|---|---|---|---|---|
| 472 | H | C$_2$H$_5$ | Cl | CH$_3$ | 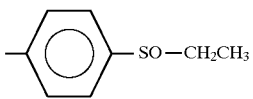 |
| 473 | H | —(CH$_2$)$_4$— | | CH$_3$ | 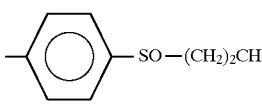 |
| 474 | H | CH$_2$OCH$_3$ | OCH$_3$ | CH$_3$ | 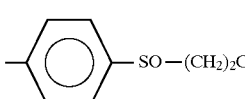 |
| 475 | H | C$_2$H$_5$ | Cl | CH$_3$ | 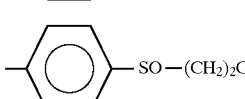 |
| 476 | H | —(CH$_2$)$_4$— | | CH$_3$ | 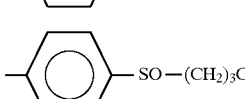 |
| 477 | H | CH$_2$OCH$_3$ | OCH$_3$ | CH$_3$ | 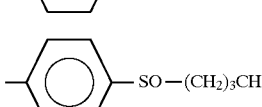 |
| 478 | H | C$_2$H$_5$ | Cl | CH$_3$ | 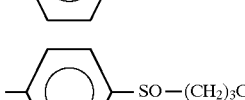 |
| 479 | H | —(CH$_2$)$_4$— | | CH$_3$ | 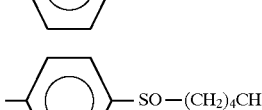 |
| 480 | H | CH$_2$OCH$_3$ | OCH$_3$ | CH$_3$ | 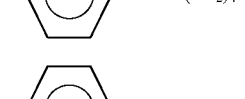 |
| 481 | H | C$_2$H$_5$ | Cl | CH$_3$ | 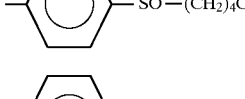 |
| 482 | H | —(CH$_2$)$_4$— | | CH$_3$ | 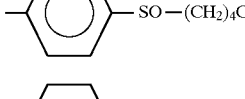 |
| 483 | H | CH$_2$OCH$_3$ | OCH$_3$ | CH$_3$ | 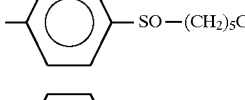 |
| 484 | H | C$_2$H$_5$ | Cl | CH$_3$ | 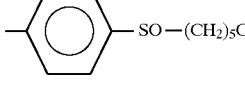 |
| 485 | H | —(CH$_2$)$_4$— | | CH$_3$ | 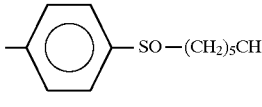 |
| 486 | H | CH$_2$OCH$_3$ | OCH$_3$ | CH$_3$ | 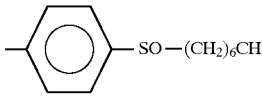 |

-continued

| | | | | | Q |
|---|---|---|---|---|---|
| 487 | H | $C_2H_5$ | Cl | $CH_3$ | —C₆H₄—SO—(CH₂)₆CH₃ |
| 488 | H | —(CH₂)₄— | | $CH_3$ | —C₆H₄—SO—(CH₂)₇CH₃ |
| 489 | H | $CH_2OCH_3$ | $OCH_3$ | $CH_3$ | —C₆H₄—SO—(CH₂)₇CH₃ |
| 490 | H | $C_2H_5$ | Cl | $CH_3$ | —C₆H₄—SO—(CH₂)₇CH₃ |
| 491 | H | —(CH₂)₄— | | $CH_3$ | —C₆H₄—SO—C(CH₃)₃ |
| 492 | H | $CH_2OCH_3$ | $OCH_3$ | $CH_3$ | —C₆H₄—SO—C(CH₃)₃ |
| 493 | H | $C_2H_5$ | Cl | $CH_3$ | —C₆H₄—SO—C(CH₃)₃ |
| 494 | H | —(CH₂)₄— | | $CH_3$ | —C₆H₄—SO—C₆H₅ |
| 495 | H | $CH_2OCH_3$ | $OCH_3$ | $CH_3$ | —C₆H₄—SO—C₆H₅ |
| 496 | H | $C_2H_5$ | Cl | $CH_3$ | —C₆H₄—SO—C₆H₅ |
| 497 | H | —(CH₂)₄— | | $CH_3$ | —C₆H₄—SO—C₆H₄—CH₃ |
| 498 | H | $CH_2OCH_3$ | $OCH_3$ | $CH_3$ | —C₆H₄—SO—C₆H₄—CH₃ |
| 499 | H | $C_2H_5$ | Cl | $CH_3$ | —C₆H₄—SO—C₆H₄—CH₃ |

| Bei-Example No. | $R^1$ | $R^2$ | $R^3$ | $R^4$ | Q | M.p. |
|---|---|---|---|---|---|---|
| 500 | H | —(CH₂)₄— | | $CH_3$ | 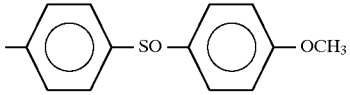 | |

-continued

| | | | | | Q |
|---|---|---|---|---|---|
| 501 | H | CH₂OCH₃ | OCH₃ | CH₃ | -C₆H₄-SO-C₆H₄-OCH₃ |
| 502 | H | C₂H₅ | Cl | CH₃ | -C₆H₄-SO-C₆H₄-OCH₃ |
| 503 | H | —(CH₂)₄— | | CH₃ | -C₆H₄-SO-C₆H₄-OCH₂CH₃ |
| 504 | H | CH₂OCH₃ | OCH₃ | CH₃ | -C₆H₄-SO-C₆H₄-OCH₂CH₃ |
| 505 | H | C₂H₅ | Cl | CH₃ | -C₆H₄-SO-C₆H₄-OCH₂CH₃ |
| 506 | H | —(CH₂)₄— | | CH₃ | -C₆H₄-SO-CH₂-C₆H₅ |
| 507 | H | CH₂OCH₃ | OCH₃ | CH₃ | -C₆H₄-SO-CH₂-C₆H₅ |
| 508 | H | C₂H₅ | Cl | CH₃ | -C₆H₄-SO-CH₂-C₆H₅ |

| Example No. | R¹ | R² | R³ | R⁴ | Q | M.p. |
|---|---|---|---|---|---|---|
| 509 | H | —(CH₂)₄— | | CH₃ | -C₆H₄-SO-CH₂-C₆H₄-Cl | |
| 510 | H | CH₂OCH₃ | OCH₃ | CH₃ | -C₆H₄-SO-CH₂-C₆H₄-Cl | |
| 511 | H | C₂H₅ | Cl | CH₃ | -C₆H₄-SO-CH₂-C₆H₄-Cl | |
| 512 | H | —(CH₂)₄— | | CH₃ | -C₆H₄-SO-CH₂-C₆H₄-C(CH₃)₃ | |
| 513 | H | CH₂OCH₃ | OCH₃ | CH₃ | -C₆H₄-SO-CH₂-C₆H₄-C(CH₃)₃ | |
| 514 | H | C₂H₅ | Cl | CH₃ | -C₆H₄-SO-CH₂-C₆H₄-C(CH₃)₃ | |

-continued
| | | | | | | |
|---|---|---|---|---|---|---|
| 515 | H | —(CH$_2$)$_4$— | | H | 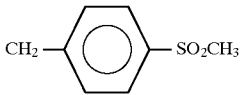 | |
| 516 | H | CH$_2$OCH$_3$ | OCH$_3$ | H | 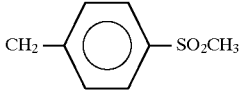 | |
| 517 | H | C$_2$H$_5$ | Cl | H | 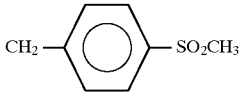 | |
| 518 | H | —(CH$_2$)$_4$— | | H | 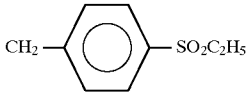 | |
| 519 | H | CH$_2$OCH$_3$ | OCH$_3$ | H | 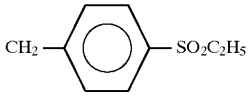 | |
| 520 | H | C$_2$H$_5$ | Cl | H | 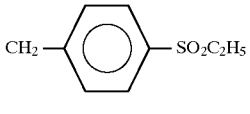 | |
| 521 | H | —(CH$_2$)$_4$— | | H | 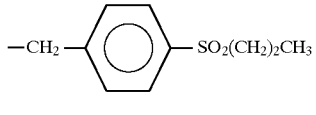 | |
| 522 | H | CH$_2$OCH$_3$ | OCH$_3$ | H | 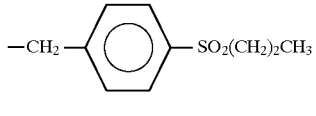 | |
| 523 | H | C$_2$H$_5$ | Cl | H | 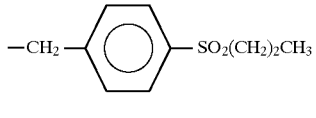 | |
| 524 | H | —(CH$_2$)$_4$— | | H | 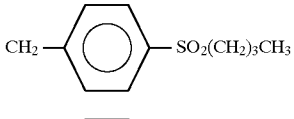 | Oil |
| 525 | H | CH$_2$OCH$_3$ | OCH$_3$ | H | 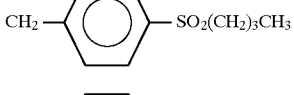 | Oil |
| 526 | H | C$_2$H$_5$ | Cl | H | 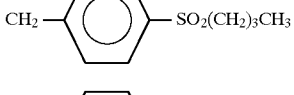 | Oil |
| 527 | H | —(CH$_2$)$_4$— | | H | 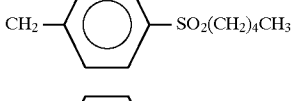 | |
| 528 | H | CH$_2$OCH$_3$ | OCH$_3$ | H | 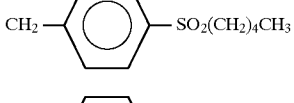 | |
| 529 | H | C$_2$H$_5$ | Cl | H | 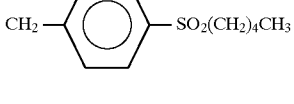 | |

-continued

| | | | | | Q | Fp. |
|---|---|---|---|---|---|---|
| 530 | H | —(CH$_2$)$_4$— | | H | CH$_2$—⟨phenyl⟩—SO$_2$(CH$_2$)$_5$CH$_3$ | |
| 531 | H | CH$_2$OCH$_3$ | OCH$_3$ | H | CH$_2$—⟨phenyl⟩—SO$_2$(CH$_2$)$_5$CH$_3$ | |
| 532 | H | C$_2$H$_5$ | Cl | H | CH$_2$—⟨phenyl⟩—SO$_2$(CH$_2$)$_5$CH$_3$ | |
| 533 | H | —(CH$_2$)$_4$— | | H | CH$_2$—⟨phenyl⟩—SO$_2$(CH$_2$)$_6$CH$_3$ | |
| 534 | H | CH$_2$OCH$_3$ | OCH$_3$ | H | CH$_2$—⟨phenyl⟩—SO$_2$(CH$_2$)$_6$CH$_3$ | |
| 535 | H | C$_2$H$_5$ | Cl | H | CH$_2$—⟨phenyl⟩—SO$_2$(CH$_2$)$_6$CH$_3$ | |

| Example No. | R$^1$ | R$^2$ | R$^3$ | R$^4$ | Q | Fp. |
|---|---|---|---|---|---|---|
| 536 | H | —(CH$_2$)$_4$— | | H | CH$_2$—⟨phenyl⟩—SO$_2$(CH$_2$)$_7$CH$_3$ | |
| 537 | H | CH$_2$OCH$_3$ | OCH$_3$ | H | CH$_2$—⟨phenyl⟩—SO$_2$(CH$_2$)$_7$CH$_3$ | |
| 538 | H | C$_2$H$_5$ | Cl | H | CH$_2$—⟨phenyl⟩—SO$_2$(CH$_2$)$_7$CH$_3$ | |
| 539 | H | —(CH$_2$)$_4$— | | H | CH$_2$—⟨phenyl⟩—SO$_2$—C(CH$_3$)$_3$ | |
| 540 | H | CH$_2$OCH$_3$ | OCH$_3$ | H | CH$_2$—⟨phenyl⟩—SO$_2$—C(CH$_3$)$_3$ | |
| 541 | H | C$_2$H$_5$ | Cl | H | CH$_2$—⟨phenyl⟩—SO$_2$—C(CH$_3$)$_3$ | |
| 542 | H | —(CH$_2$)$_4$— | | H | CH$_2$—⟨phenyl⟩—SO$_2$—CH$_2$—⟨phenyl⟩ | |
| 543 | H | CH$_2$OCH$_3$ | OCH$_3$ | H | CH$_2$—⟨phenyl⟩—SO$_2$—CH$_2$—⟨phenyl⟩ | |

-continued
| | | | | | Q |
|---|---|---|---|---|---|
| 544 | H | C$_2$H$_5$ | Cl | H | 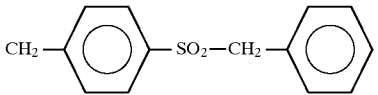 |
| Example No. | R$^1$ | R$^2$ | R$^3$ | R$^4$ | Q | M.p. |
|---|---|---|---|---|---|---|
| 545 | H | —(CH$_2$)$_4$— | | H | 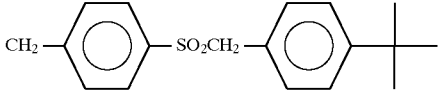 | |
| 546 | H | CH$_2$OCH$_3$ | OCH$_3$ | H | 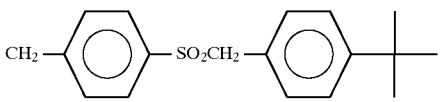 | |
| 547 | H | C$_2$H$_5$ | Cl | H | 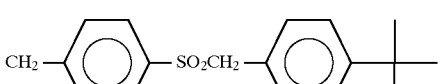 | |
| 548 | H | —(CH$_2$)$_4$— | | H | 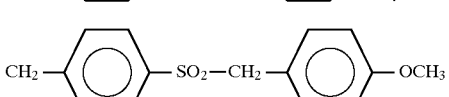 | |
| 549 | H | CH$_2$OCH$_3$ | OCH$_3$ | H | 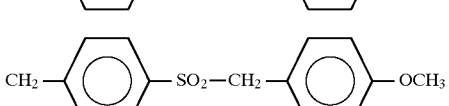 | |
| 550 | H | C$_2$H$_5$ | Cl | H |  | |
| 551 | H | —(CH$_2$)$_4$— | | H |  | |
| 552 | H | CH$_2$OCH$_3$ | OCH$_3$ | H |  | |
| 553 | H | C$_2$H$_5$ | Cl | H | 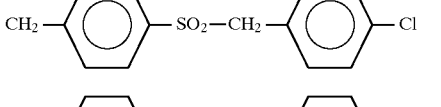 | |
| 554 | H | —(CH$_2$)$_4$— | | H | 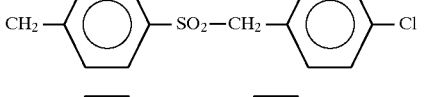 | |
| 555 | H | CH$_2$OCH$_3$ | OCH$_3$ | H | 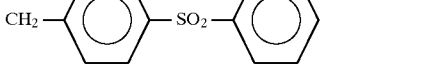 | |
| 556 | H | C$_2$H$_5$ | Cl | H | 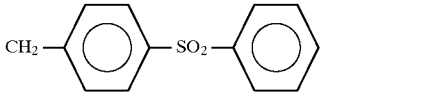 | |
| 557 | H | —(CH$_2$)$_4$— | | H | 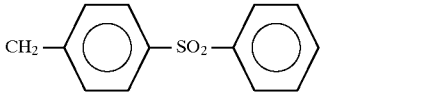 | |

-continued

| | | | | | |
|---|---|---|---|---|---|
| 558 | H | CH₂OCH₃ | OCH₃ | H | CH₂–C₆H₄–SO₂–C₆H₄–Cl |
| 559 | H | C₂H₅ | Cl | H | CH₂–C₆H₄–SO₂–C₆H₄–Cl |
| 560 | H | —(CH₂)₄— | | H | CH₂–C₆H₄–SO₂–C₆H₄–CH₃ |
| 561 | H | CH₂OCH₃ | OCH₃ | H | CH₂–C₆H₄–SO₂–C₆H₄–CH₃ |
| 562 | H | C₂H₅ | Cl | H | CH₂–C₆H₄–SO₂–C₆H₄–CH₃ |
| 563 | H | —(CH₂)₄— | | H | CH₂–C₆H₄–SO₂–C₆H₄–OCH₃ |
| 564 | H | CH₂OCH₃ | OCH₃ | H | CH₂–C₆H₄–SO₂–C₆H₄–OCH₃ |
| 565 | H | C₂H₅ | Cl | H | CH₂–C₆H₄–SO₂–C₆H₄–OCH₃ |
| 566 | H | —(CH₂)₄— | | H | CH₂–C₆H₄–SO₂–C₆H₄–NO₂ |
| 567 | H | CH₂OCH₃ | OCH₃ | H | CH₂–C₆H₄–SO₂–C₆H₄–NO₂ |
| 568 | H | C₂H₅ | Cl | H | CH₂–C₆H₄–SO₂–C₆H₄–NO₂ |
| 569 | H | —(CH₂)₄— | | CH₃ | C₆H₄–SO₂–CH₃ |
| 570 | H | CH₂OCH₃ | OCH₃ | CH₃ | C₆H₄–SO₂–CH₃ |
| 571 | H | C₂H₅ | Cl | CH₃ | C₆H₄–SO₂–CH₃ |
| 572 | H | —(CH₂)₄— | | CH₃ | C₆H₄–SO₂–(CH₂)₂CH₃ |

-continued
| | | | | | |
|---|---|---|---|---|---|
| 573 | H | CH$_2$OCH$_3$ | OCH$_3$ | CH$_3$ | 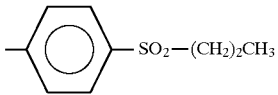 |
| 574 | H | C$_2$H$_5$ | Cl | CH$_3$ | 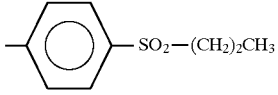 |
| 575 | H | —(CH$_2$)$_4$— | | CH$_3$ | 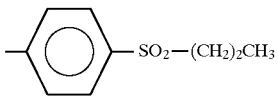 |
| 576 | H | CH$_2$OCH$_3$ | OCH$_3$ | CH$_3$ | 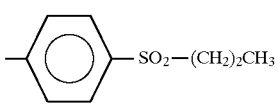 |
| 577 | H | C$_2$H$_5$ | Cl | CH$_3$ | 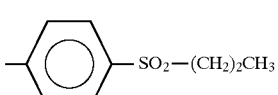 |
| 578 | H | —(CH$_2$)$_4$— | | CH$_3$ | 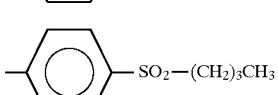 |
| 579 | H | CH$_2$OCH$_3$ | OCH$_3$ | CH$_3$ | 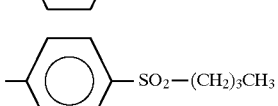 |
| 580 | H | C$_2$H$_5$ | Cl | CH$_3$ | 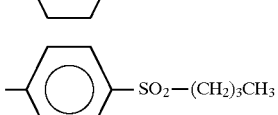 |
| 581 | H | —(CH$_2$)$_4$— | | CH$_3$ |  |
| 582 | H | CH$_2$OCH$_3$ | OCH$_3$ | CH$_3$ |  |
| 583 | H | C$_2$H$_5$ | Cl | CH$_3$ | 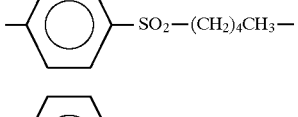 |
| 584 | H | —(CH$_2$)$_4$— | | CH$_3$ | 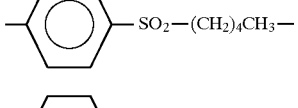 |
| 585 | H | CH$_2$OCH$_3$ | OCH$_3$ | CH$_3$ | 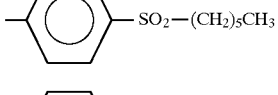 |
| 586 | H | C$_2$H$_5$ | Cl | CH$_3$ | 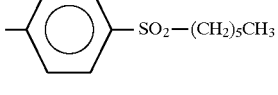 |
| 587 | H | —(CH$_2$)$_4$— | | CH$_3$ | 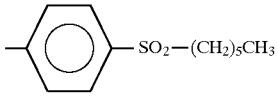 |

-continued
| | | | | | |
|---|---|---|---|---|---|
| 588 | H | CH₂OCH₃ | OCH₃ | CH₃ | 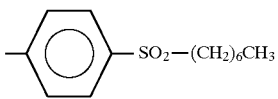 |
| 589 | H | C₂H₅ | Cl | CH₃ | 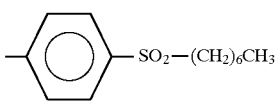 |
| 590 | H | —(CH₂)₄— | | CH₃ | 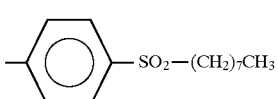 |
| 591 | H | CH₂OCH₃ | OCH₃ | CH₃ | 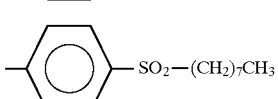 |
| 592 | H | C₂H₅ | Cl | CH₃ | 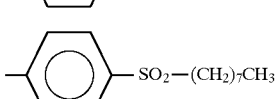 |
| 593 | H | —(CH₂)₄— | | CH₃ | 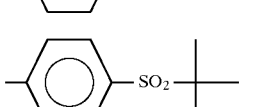 |
| 594 | H | CH₂OCH₃ | OCH₃ | CH₃ | 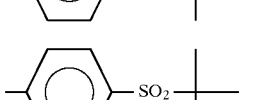 |
| 595 | H | C₂H₅ | Cl | CH₃ | 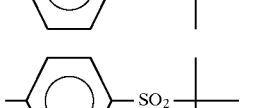 |
| 596 | H | —(CH₂)₄— | | CH₃ | 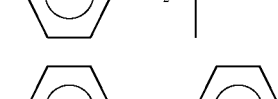 |
| 597 | H | CH₂OCH₃ | OCH₃ | CH₃ | 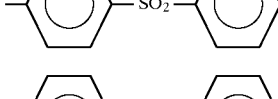 |
| 598 | H | C₂H₅ | Cl | CH₃ | 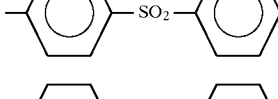 |
| 599 | H | —(CH₂)₄— | | CH₃ | 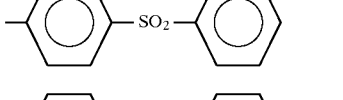 |
| 600 | H | CH₂OCH₃ | OCH₃ | CH₃ | 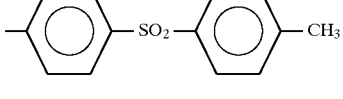 |
| 601 | H | C₂H₅ | Cl | CH₃ | 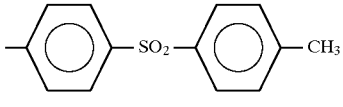 |
| 602 | H | —(CH₂)₄— | | CH₃ | 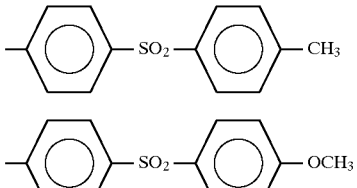 |

-continued
| | | | | | |
|---|---|---|---|---|---|
| 603 | H | CH₂OCH₃ | OCH₃ | CH₃ | 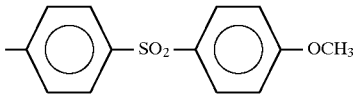 |
| 604 | H | C₂H₅ | Cl | CH₃ | 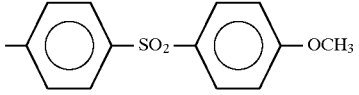 |
| 605 | H | —(CH₂)₄— | | CH₃ | 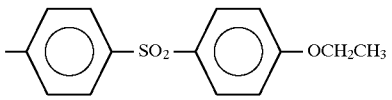 |
| 606 | H | CH₂OCH₃ | OCH₃ | CH₃ | 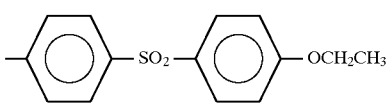 |
| 607 | H | C₂H₅ | Cl | CH₃ | 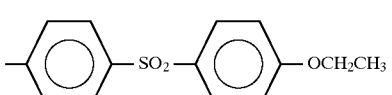 |
| 608 | H | —(CH₂)₄— | | CH₃ | 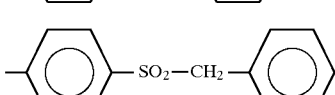 |
| 609 | H | CH₂OCH₃ | OCH₃ | CH₃ | 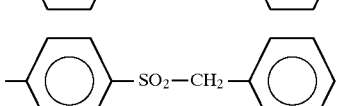 |
| 610 | H | C₂H₅ | Cl | CH₃ | 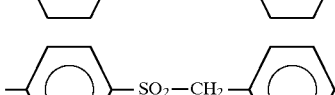 |
| 611 | H | —(CH₂)₄— | | CH₃ | 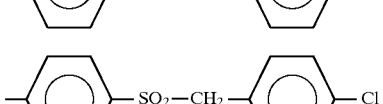 |
| 612 | H | CH₂OCH₃ | OCH₃ | CH₃ |  |
| 613 | H | C₂H₅ | Cl | CH₃ | 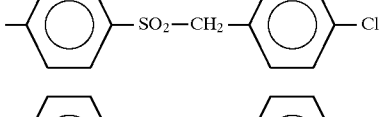 |
| 614 | H | —(CH₂)₄— | | CH₃ | 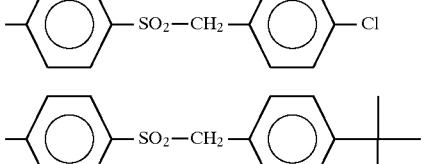 |
| 615 | H | CH₂OCH₃ | OCH₃ | CH₃ | 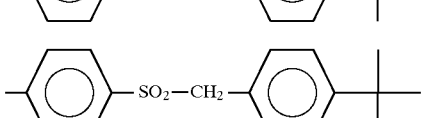 |
| 616 | H | C₂H₅ | Cl | CH₃ |  |
| 617 | H | —(CH₂)₄— | | CH₃ | 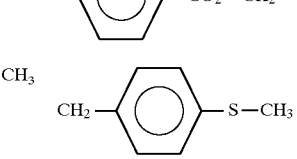 |

| | | | | | |
|---|---|---|---|---|---|
| 618 | H | CH₂OCH₃ | OCH₃ | CH₃ | 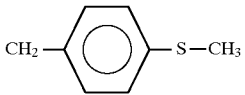 |
| 619 | H | C₂H₅ | Cl | CH₃ | 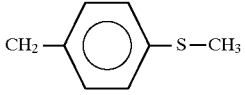 |
| 620 | H | —(CH₂)₄— | | CH₃ | 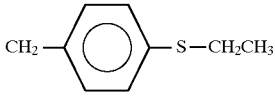 |
| 621 | H | CH₂OCH₃ | OCH₃ | CH₃ | 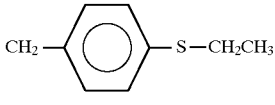 |
| 622 | H | C₂H₅ | Cl | CH₃ | 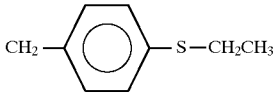 |
| 623 | H | —(CH₂)₄— | | CH₃ | 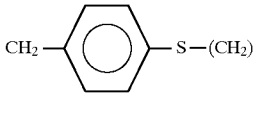 |
| 624 | H | CH₂OCH₃ | OCH₃ | CH₃ | 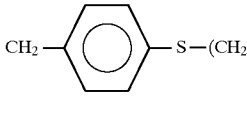 |
| 625 | H | C₂H₅ | Cl | CH₃ | 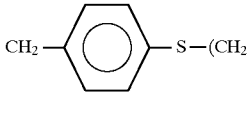 |
| 626 | H | —(CH₂)₄— | | CH₃ | 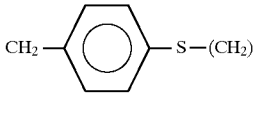 |
| 627 | H | CH₂OCH₃ | OCH₃ | CH₃ | 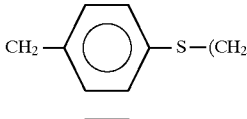 |
| 628 | H | C₂H₅ | Cl | CH₃ | 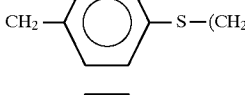 |
| 629 | H | —(CH₂)₄— | | CH₃ | 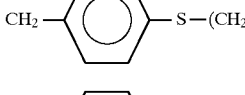 |
| 630 | H | CH₂OCH₃ | OCH₃ | CH₃ | 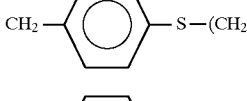 |
| 631 | H | C₂H₅ | Cl | CH₃ | 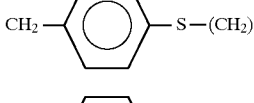 |
| 632 | H | —(CH₂)₄— | | CH₃ | 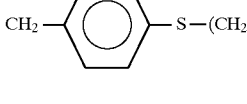 |

-continued

| | | | | | |
|---|---|---|---|---|---|
| 633 | H | CH$_2$OCH$_3$ | OCH$_3$ | CH$_3$ | CH$_2$—C$_6$H$_4$—S—(CH$_2$)$_5$CH$_3$ |
| 634 | H | C$_2$H$_5$ | Cl | CH$_3$ | CH$_2$—C$_6$H$_4$—S—(CH$_2$)$_5$CH$_3$ |
| 635 | H | —(CH$_2$)$_4$— | | CH$_3$ | CH$_2$—C$_6$H$_4$—S—(CH$_2$)$_6$CH$_3$ |
| 636 | H | CH$_2$OCH$_3$ | OCH$_3$ | CH$_3$ | CH$_2$—C$_6$H$_4$—S—(CH$_2$)$_6$CH$_3$ |
| 637 | H | C$_2$H$_5$ | Cl | CH$_3$ | CH$_2$—C$_6$H$_4$—S—(CH$_2$)$_6$CH$_3$ |
| 638 | H | —(CH$_2$)$_4$— | | CH$_3$ | CH$_2$—C$_6$H$_4$—S—(CH$_2$)$_7$CH$_3$ |
| 639 | H | CH$_2$OCH$_3$ | OCH$_3$ | CH$_3$ | CH$_2$—C$_6$H$_4$—S—(CH$_2$)$_7$CH$_3$ |
| 640 | H | C$_2$H$_5$ | Cl | CH$_3$ | CH$_2$—C$_6$H$_4$—S—(CH$_2$)$_7$CH$_3$ |
| 641 | H | —(CH$_2$)$_4$— | | CH$_3$ | CH$_2$—C$_6$H$_4$—S—C(CH$_3$)$_3$ |
| 642 | H | CH$_2$OCH$_3$ | OCH$_3$ | CH$_3$ | CH$_2$—C$_6$H$_4$—S—C(CH$_3$)$_3$ |
| 643 | H | C$_2$H$_5$ | Cl | CH$_3$ | CH$_2$—C$_6$H$_4$—S—C(CH$_3$)$_3$ |
| 644 | H | —(CH$_2$)$_4$— | | CH$_3$ | CH$_2$—C$_6$H$_4$—S—C$_6$H$_5$ |
| 645 | H | CH$_2$OCH$_3$ | OCH$_3$ | CH$_3$ | CH$_2$—C$_6$H$_4$—S—C$_6$H$_5$ |
| 646 | H | C$_2$H$_5$ | Cl | CH$_3$ | CH$_2$—C$_6$H$_4$—S—C$_6$H$_5$ |
| 647 | H | —(CH$_2$)$_4$— | | CH$_3$ | CH$_2$—C$_6$H$_4$—S—C$_6$H$_4$—CH$_3$ |

-continued

| | | | | | |
|---|---|---|---|---|---|
| 648 | H | CH₂OCH₃ | OCH₃ | CH₃ | CH₂–⟨C₆H₄⟩–S–⟨C₆H₄⟩–CH₃ |
| 649 | H | C₂H₅ | Cl | CH₃ | CH₂–⟨C₆H₄⟩–S–⟨C₆H₄⟩–CH₃ |
| 650 | H | —(CH₂)₄— | | CH₃ | CH₂–⟨C₆H₄⟩–S–⟨C₆H₄⟩–OCH₃ |
| 651 | H | CH₂OCH₃ | OCH₃ | CH₃ | CH₂–⟨C₆H₄⟩–S–⟨C₆H₄⟩–OCH₃ |
| 652 | H | C₂H₅ | Cl | CH₃ | CH₂–⟨C₆H₄⟩–S–⟨C₆H₄⟩–OCH₃ |
| 653 | H | —(CH₂)₄— | | CH₃ | CH₂–⟨C₆H₄⟩–S–⟨C₆H₄⟩–OCH₂CH₃ |
| 654 | H | CH₂OCH₃ | OCH₃ | CH₃ | CH₂–⟨C₆H₄⟩–S–⟨C₆H₄⟩–OCH₂CH₃ |
| 655 | H | C₂H₅ | Cl | CH₃ | CH₂–⟨C₆H₄⟩–S–⟨C₆H₄⟩–OCH₂CH₃ |
| 656 | H | —(CH₂)₄— | | CH₃ | CH₂–⟨C₆H₄⟩–S–CH₂–⟨C₆H₅⟩ |
| 657 | H | CH₂OCH₃ | OCH₃ | CH₃ | CH₂–⟨C₆H₄⟩–S–CH₂–⟨C₆H₅⟩ |
| 658 | H | C₂H₅ | Cl | CH₃ | CH₂–⟨C₆H₄⟩–S–CH₂–⟨C₆H₅⟩ |
| 659 | H | —(CH₂)₄— | | CH₃ | CH₂–⟨C₆H₄⟩–S–CH₂–⟨C₆H₄⟩–Cl |
| 660 | H | CH₂OCH₃ | OCH₃ | CH₃ | CH₂–⟨C₆H₄⟩–S–CH₂–⟨C₆H₄⟩–Cl |
| 661 | H | C₂H₅ | Cl | CH₃ | CH₂–⟨C₆H₄⟩–S–CH₂–⟨C₆H₄⟩–Cl |
| 662 | H | —(CH₂)₄— | | CH₃ | CH₂–⟨C₆H₄⟩–S–CH₂–⟨C₆H₄⟩–C(CH₃)₃ |

| | | | | | |
|---|---|---|---|---|---|
| 663 | H | CH₂OCH₃ | OCH₃ | CH₃ | 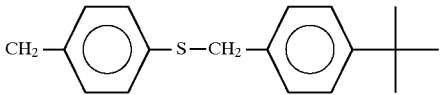 |
| 664 | H | C₂H₅ | Cl | CH₃ | 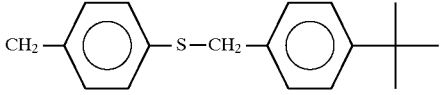 |
| 665 | H | —(CH₂)₄— | | CH₃ | 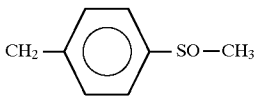 |
| 666 | H | CH₂OCH₃ | OCH₃ | CH₃ | 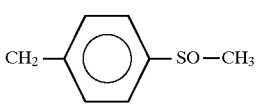 |
| 667 | H | C₂H₅ | Cl | CH₃ | 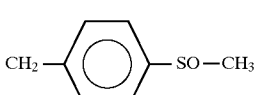 |
| 668 | H | —(CH₂)₄— | | CH₃ | 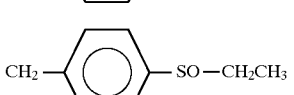 |
| 669 | H | CH₂OCH₃ | OCH₃ | CH₃ | 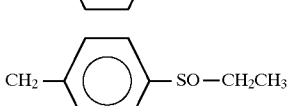 |
| 670 | H | C₂H₅ | Cl | CH₃ | 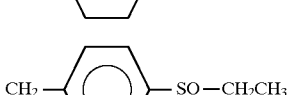 |
| 671 | H | —(CH₂)₄— | | CH₃ | 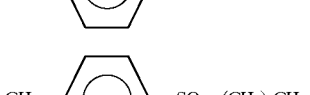 |
| 672 | H | CH₂OCH₃ | OCH₃ | CH₃ |  |
| 673 | H | C₂H₅ | Cl | CH₃ | 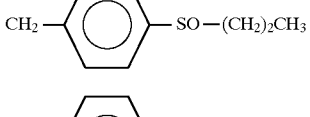 |
| 674 | H | —(CH₂)₄— | | CH₃ | 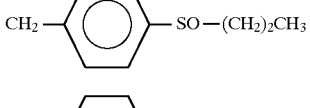 |
| 675 | H | CH₂OCH₃ | OCH₃ | CH₃ | 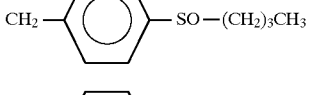 |
| 676 | H | C₂H₅ | Cl | CH₃ | 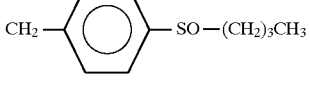 |
| 677 | H | —(CH₂)₄— | | CH₃ | 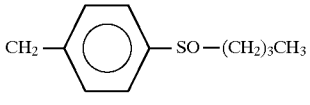 |

-continued
| | | | | | |
|---|---|---|---|---|---|
| 678 | H | CH₂OCH₃ | OCH₃ | CH₃ | 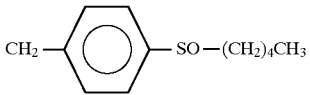 |
| 679 | H | C₂H₅ | Cl | CH₃ | 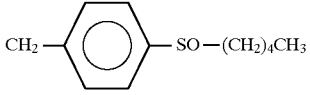 |
| 680 | H | —(CH₂)₄— | | CH₃ | 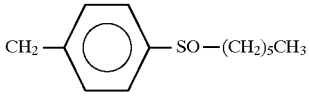 |
| 681 | H | CH₂OCH₃ | OCH₃ | CH₃ | 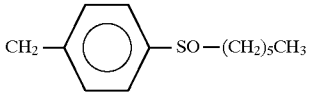 |
| 682 | H | C₂H₅ | Cl | CH₃ | 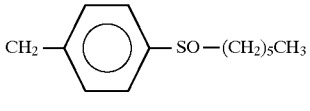 |
| 683 | H | —(CH₂)₄— | | CH₃ | 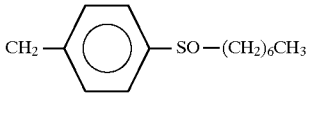 |
| 684 | H | CH₂OCH₃ | OCH₃ | CH₃ | 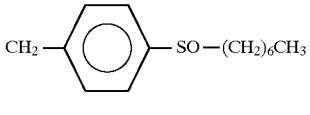 |
| 685 | H | C₂H₅ | Cl | CH₃ | 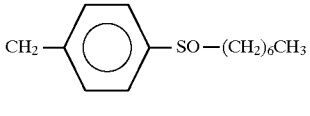 |
| 686 | H | —(CH₂)₄— | | CH₃ | 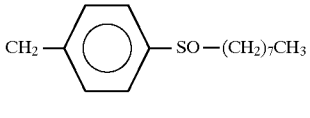 |
| 687 | H | CH₂OCH₃ | OCH₃ | CH₃ | 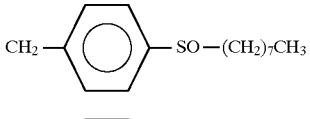 |
| 688 | H | C₂H₅ | Cl | CH₃ | 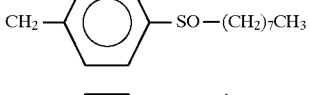 |
| 689 | H | —(CH₂)₄— | | CH₃ | 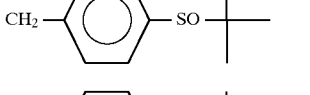 |
| 690 | H | CH₂OCH₃ | OCH₃ | CH₃ | 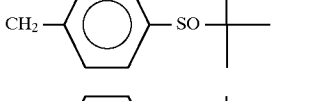 |
| 691 | H | C₂H₅ | Cl | CH₃ | 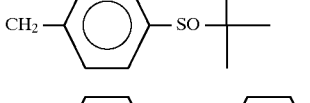 |
| 692 | H | —(CH₂)₄— | | CH₃ | 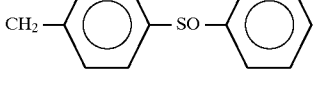 |

| | | | | | |
|---|---|---|---|---|---|
| 693 | H | CH₂OCH₃ | OCH₃ | CH₃ | CH₂—⟨C₆H₄⟩—SO—⟨C₆H₅⟩ |
| 694 | H | C₂H₅ | Cl | CH₃ | CH₂—⟨C₆H₄⟩—SO—⟨C₆H₅⟩ |
| 695 | H | —(CH₂)₄— | | CH₃ | CH₂—⟨C₆H₄⟩—SO—⟨C₆H₄⟩—CH₃ |
| 696 | H | CH₂OCH₃ | OCH₃ | CH₃ | CH₂—⟨C₆H₄⟩—SO—⟨C₆H₄⟩—CH₃ |
| 697 | H | C₂H₅ | Cl | CH₃ | CH₂—⟨C₆H₄⟩—SO—⟨C₆H₄⟩—CH₃ |
| 698 | H | —(CH₂)₄— | | CH₃ | CH₂—⟨C₆H₄⟩—SO—⟨C₆H₄⟩—OCH₃ |
| 699 | H | CH₂OCH₃ | OCH₃ | CH₃ | CH₂—⟨C₆H₄⟩—SO—⟨C₆H₄⟩—OCH₃ |
| 700 | H | C₂H₅ | Cl | CH₃ | CH₂—⟨C₆H₄⟩—SO—⟨C₆H₄⟩—OCH₃ |
| 701 | H | —(CH₂)₄— | | CH₃ | CH₂—⟨C₆H₄⟩—SO—⟨C₆H₄⟩—CH₂CH₃ |
| 702 | H | CH₂OCH₃ | OCH₃ | CH₃ | CH₂—⟨C₆H₄⟩—SO—⟨C₆H₄⟩—CH₂CH₃ |
| 703 | H | C₂H₅ | Cl | CH₃ | CH₂—⟨C₆H₄⟩—SO—⟨C₆H₄⟩—CH₂CH₃ |
| 704 | H | —(CH₂)₄— | | CH₃ | CH₂—⟨C₆H₄⟩—SO—CH₂—⟨C₆H₅⟩ |
| 705 | H | CH₂OCH₃ | OCH₃ | CH₃ | CH₂—⟨C₆H₄⟩—SO—CH₂—⟨C₆H₅⟩ |
| 706 | H | C₂H₅ | Cl | CH₃ | CH₂—⟨C₆H₄⟩—SO—CH₂—⟨C₆H₅⟩ |
| 707 | H | —(CH₂)₄— | | CH₃ | CH₂—⟨C₆H₄⟩—SO—CH₂—⟨C₆H₄⟩—Cl |

| | | | | | |
|---|---|---|---|---|---|
| 708 | H | CH₂OCH₃ | OCH₃ | CH₃ | CH₂—⟨C₆H₄⟩—SO—CH₂—⟨C₆H₄⟩—Cl |
| 709 | H | C₂H₅ | Cl | CH₃ | CH₂—⟨C₆H₄⟩—SO—CH₂—⟨C₆H₄⟩—Cl |
| 710 | H | —(CH₂)₄— | | CH₃ | CH₂—⟨C₆H₄⟩—O—CH₂—⟨C₆H₄⟩—C(CH₃)₃ |
| 711 | H | CH₂OCH₃ | OCH₃ | CH₃ | CH₂—⟨C₆H₄⟩—O—CH₂—⟨C₆H₄⟩—C(CH₃)₃ |
| 712 | H | C₂H₅ | Cl | CH₃ | CH₂—⟨C₆H₄⟩—O—CH₂—⟨C₆H₄⟩—C(CH₃)₃ |
| 713 | H | —(CH₂)₄— | | CH₃ | CH₂—⟨C₆H₄⟩—SO₂CH₃ |
| 714 | H | CH₂OCH₃ | OCH₃ | CH₃ | CH₂—⟨C₆H₄⟩—SO₂CH₃ |
| 715 | H | C₂H₅ | Cl | CH₃ | CH₂—⟨C₆H₄⟩—SO₂CH₃ |
| 716 | H | —(CH₂)₄— | | CH₃ | CH₂—⟨C₆H₄⟩—SO₂—CH₂CH₃ |
| 717 | H | CH₂OCH₃ | OCH₃ | CH₃ | CH₂—⟨C₆H₄⟩—SO₂—CH₂CH₃ |
| 718 | H | C₂H₅ | Cl | CH₃ | CH₂—⟨C₆H₄⟩—SO₂—CH₂CH₃ |
| 719 | H | —(CH₂)₄— | | CH₃ | CH₂—⟨C₆H₄⟩—SO₂(CH₂)₂CH₃ |
| 720 | H | CH₂OCH₃ | OCH₃ | CH₃ | CH₂—⟨C₆H₄⟩—SO₂(CH₂)₂CH₃ |
| 721 | H | C₂H₅ | Cl | CH₃ | CH₂—⟨C₆H₄⟩—SO₂(CH₂)₂CH₃ |
| 722 | H | —(CH₂)₄— | | CH₃ | CH₂—⟨C₆H₄⟩—SO₂(CH₂)₃CH₃ |

-continued

| | | | | | |
|---|---|---|---|---|---|
| 723 | H | CH$_2$OCH$_3$ | OCH$_3$ | CH$_3$ | CH$_2$—⟨C$_6$H$_4$⟩—SO$_2$(CH$_2$)$_3$CH$_3$ |
| 724 | H | C$_2$H$_5$ | Cl | CH$_3$ | CH$_2$—⟨C$_6$H$_4$⟩—SO$_2$(CH$_2$)$_3$CH$_3$ |
| 725 | H | —(CH$_2$)$_4$— | | CH$_3$ | CH$_2$—⟨C$_6$H$_4$⟩—SO$_2$(CH$_2$)$_4$CH$_3$ |
| 726 | H | CH$_2$OCH$_3$ | OCH$_3$ | CH$_3$ | CH$_2$—⟨C$_6$H$_4$⟩—SO$_2$(CH$_2$)$_4$CH$_3$ |
| 727 | H | C$_2$H$_5$ | Cl | CH$_3$ | CH$_2$—⟨C$_6$H$_4$⟩—SO$_2$(CH$_2$)$_4$CH$_3$ |
| 728 | H | —(CH$_2$)$_4$— | | CH$_3$ | CH$_2$—⟨C$_6$H$_4$⟩—SO$_2$(CH$_2$)$_5$CH$_3$ |
| 729 | H | CH$_2$OCH$_3$ | OCH$_3$ | CH$_3$ | CH$_2$—⟨C$_6$H$_4$⟩—SO$_2$(CH$_2$)$_5$CH$_3$ |
| 730 | H | C$_2$H$_5$ | Cl | CH$_3$ | CH$_2$—⟨C$_6$H$_4$⟩—SO$_2$(CH$_2$)$_5$CH$_3$ |
| 731 | H | —(CH$_2$)$_4$— | | CH$_3$ | CH$_2$—⟨C$_6$H$_4$⟩—SO$_2$(CH$_2$)$_6$CH$_3$ |
| 732 | H | CH$_2$OCH$_3$ | OCH$_3$ | CH$_3$ | CH$_2$—⟨C$_6$H$_4$⟩—SO$_2$(CH$_2$)$_6$CH$_3$ |
| 733 | H | C$_2$H$_5$ | Cl | CH$_3$ | CH$_2$—⟨C$_6$H$_4$⟩—SO$_2$(CH$_2$)$_6$CH$_3$ |
| 734 | H | —(CH$_2$)$_4$— | | CH$_3$ | CH$_2$—⟨C$_6$H$_4$⟩—SO$_2$(CH$_2$)$_7$CH$_3$ |
| 735 | H | CH$_2$OCH$_3$ | OCH$_3$ | CH$_3$ | CH$_2$—⟨C$_6$H$_4$⟩—SO$_2$(CH$_2$)$_7$CH$_3$ |
| 736 | H | C$_2$H$_5$ | Cl | CH$_3$ | CH$_2$—⟨C$_6$H$_4$⟩—SO$_2$(CH$_2$)$_7$CH$_3$ |
| 737 | H | —(CH$_2$)$_4$— | | CH$_3$ | CH$_2$—⟨C$_6$H$_4$⟩—SO$_2$—C(CH$_3$)$_3$ |

-continued
| | | | | | |
|---|---|---|---|---|---|
| 738 | H | CH₂OCH₃ | OCH₃ | CH₃ | 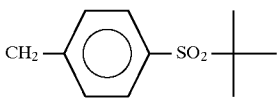 |
| 739 | H | C₂H₅ | Cl | CH₃ | 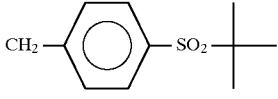 |
| 740 | H | —(CH₂)₄— | | CH₃ | 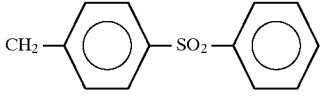 |
| 741 | H | CH₂OCH₃ | OCH₃ | CH₃ | 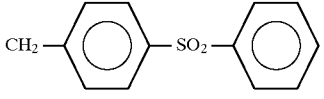 |
| 742 | H | C₂H₅ | Cl | CH₃ | 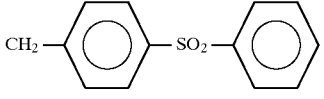 |
| 743 | H | —(CH₂)₄— | | CH₃ | 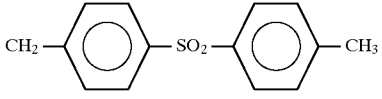 |
| 744 | H | CH₂OCH₃ | OCH₃ | CH₃ | 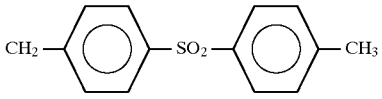 |
| 745 | H | C₂H₅ | Cl | CH₃ | 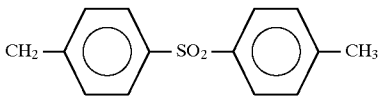 |
| 746 | H | —(CH₂)₄— | | CH₃ | 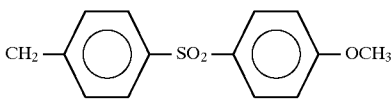 |
| 747 | H | CH₂OCH₃ | OCH₃ | CH₃ | 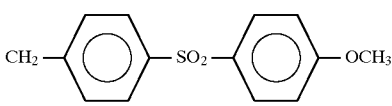 |
| 748 | H | C₂H₅ | Cl | CH₃ | 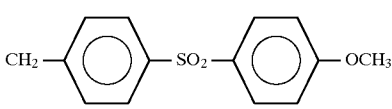 |
| 749 | H | —(CH₂)₄— | | CH₃ | 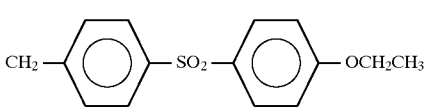 |
| 750 | H | CH₂OCH₃ | OCH₃ | CH₃ | 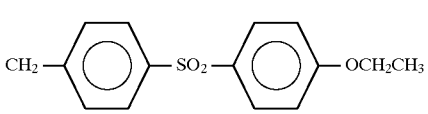 |
| 751 | H | C₂H₅ | Cl | CH₃ | 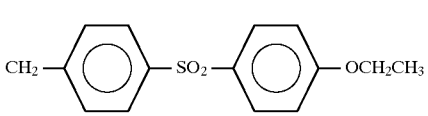 |
| 752 | H | —(CH₂)₄— | | CH₃ | 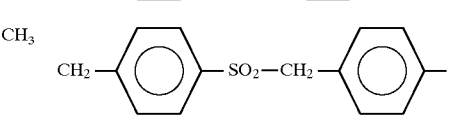 |

| # | | | | | Structure | |
|---|---|---|---|---|---|---|
| 753 | H | $CH_2OCH_3$ | $OCH_3$ | $CH_3$ | $CH_2$-C$_6$H$_4$-SO$_2$-CH$_2$-C$_6$H$_4$- | |
| 754 | H | $C_2H_5$ | Cl | $CH_3$ | $CH_2$-C$_6$H$_4$-SO$_2$-CH$_2$-C$_6$H$_4$- | |
| 755 | H | $-(CH_2)_4-$ | | $CH_3$ | $CH_2$-C$_6$H$_4$-SO$_2$-CH$_2$-C$_6$H$_4$-Cl | |
| 756 | H | $CH_2OCH_3$ | $OCH_3$ | $CH_3$ | $CH_2$-C$_6$H$_4$-SO$_2$-CH$_2$-C$_6$H$_4$-Cl | |
| 757 | H | $C_2H_5$ | Cl | $CH_3$ | $CH_2$-C$_6$H$_4$-SO$_2$-CH$_2$-C$_6$H$_4$-Cl | |
| 758 | H | $-(CH_2)_4-$ | | $CH_3$ | $CH_2$-C$_6$H$_4$-SO$_2$CH$_2$-C$_6$H$_4$-t-Bu | |
| 759 | H | $CH_2OCH_3$ | $OCH_3$ | $CH_3$ | $CH_2$-C$_6$H$_4$-SO$_2$CH$_2$-C$_6$H$_4$-t-Bu | |
| 760 | H | $C_2H_5$ | Cl | $CH_3$ | $CH_2$-C$_6$H$_4$-SO$_2$CH$_2$-C$_6$H$_4$-t-Bu | |
| 761 | H | $-(CH_2)_4-$ | | H | $CH_2$-(2-thienyl) | Oil |
| 762 | H | $CH_2OCH_3$ | $OCH_3$ | H | $CH_2$-(2-thienyl) | Oil |
| 763 | H | $C_2H_5$ | Cl | H | $CH_2$-(2-thienyl) | Oil |
| 764 | H | $-(CH_2)_4-$ | | H | $CH_2$-(2-thienyl) | 69° C. |
| 765 | H | $-(CH_2)_4-$ | | H | $CH_2$-(2-furyl) | |
| 766 | H | $CH_2OH_3$ | $OCH_3$ | H | $CH_2$-(2-furyl) | |
| 767 | H | $C_2H_5$ | Cl | H | $CH_2$-(2-furyl) | |
| 768 | H | $-(CH_2)_4-$ | | H | $CH_2$-C$_6$H$_4$-C$_6$H$_5$ | Oil |

-continued
| | | | | | |
|---|---|---|---|---|---|
| 769 | H | −CH₂(CH₃)−CH₂CH₂CH₂− | H | 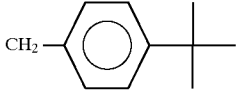 | Oil |
| 770 | H | −(CH₂)₃−S− | H | 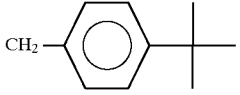 | 62–66° C. |
| 771 | H | −CH₂−S−CH₂− | H | 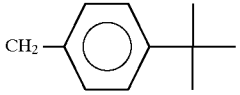 | Oil |
| 772 | H | −CH₂CH₂−S−CH₂− | H | 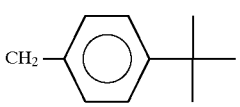 | Oil |
| 773 | H | −(CH₂)₃−S− | H | 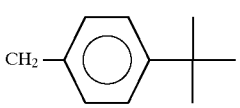 | 99–102° C. |
| 774 | H | −(CH₂)₂−S−CH₂− | H | 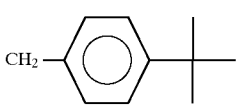 | 97–99° C. |
| 775 | H | −(CH₂)₄− | H | 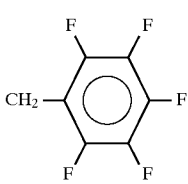 | |
| 776 | H | CH₂OH₂ | OCH₃ | H | 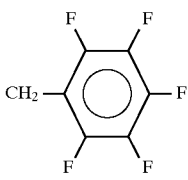 |
| 777 | H | C₂H₅ | Cl | H | 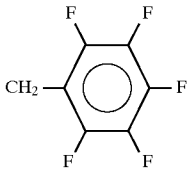 |
| 778 | H | −(CH₂)₄− | H | 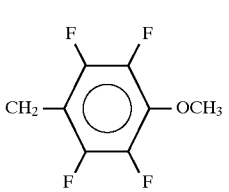 | |
| 779 | H | CH₂OCH₃ | OCH₃ | H | 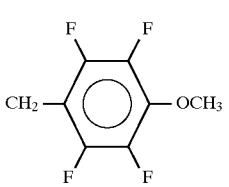 |

-continued
| | | | | | |
|---|---|---|---|---|---|
| 780 | H | C₂H₅ | Cl | H | 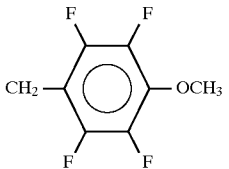 |
| 781 | H | —(CH₂)₄— | | H | 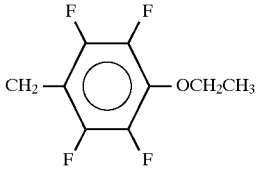 |
| 782 | H | CH₂OCH₃ | OCH₃ | H | 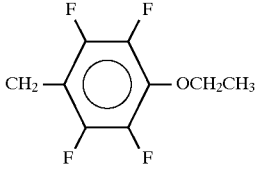 |
| 783 | H | C₂H₅ | Cl | H | 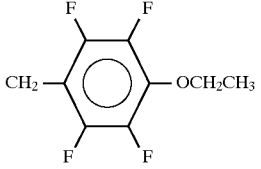 |
| 784 | H | —(CH₂)₄— | | H | 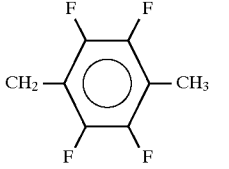 |
| 785 | H | CH₂OCH₃ | OCH₃ | H | 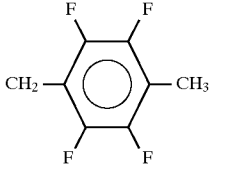 |
| 786 | H | C₂H₅ | Cl | H | 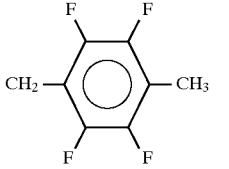 |
| 787 | H | —(CH₂)₄— | | H | 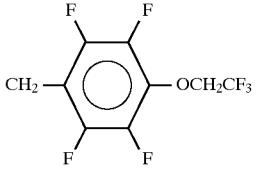 |
| 788 | H | CH₂OCH₃ | OCH₃ | H | 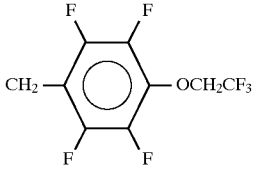 |

-continued
| 789 | H | C₂H₅ | | Cl | H | 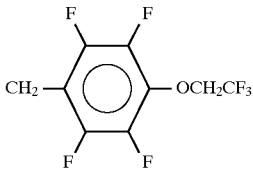 |
| --- | --- | --- | --- | --- | --- | --- |
| 790 | H | —(CH₂)₄— | | | H | 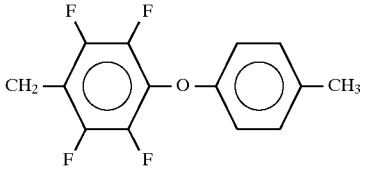 |
| 791 | H | CH₂OCH₃ | | OCH₃ | H | 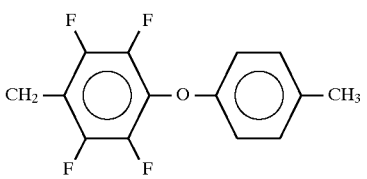 |
| 792 | H | C₂H₅ | | Cl | H | 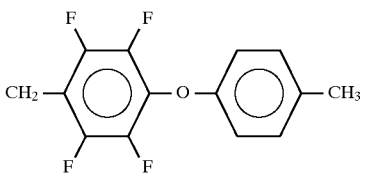 |
| 793 | H | —(CH₂)₄— | | | CH₃ | 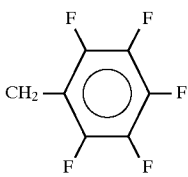 |
| 794 | H | CH₂OCH₃ | | OCH₃ | CH₃ | 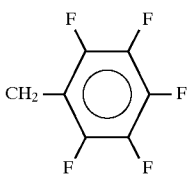 |
| 795 | H | C₂H₅ | | Cl | CH₃ | 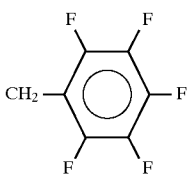 |
| 796 | H | —(CH₂)₄— | | | CH₃ | 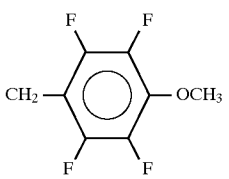 |
| 797 | H | CH₂OCH₃ | | OCH₃ | CH₃ | 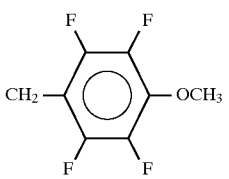 |

-continued
| | | | | | |
|---|---|---|---|---|---|
| 798 | H | C₂H₅ | Cl | CH₃ | 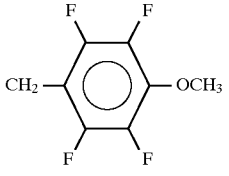 |
| 799 | H | —(CH₂)₄— | | CH₃ | 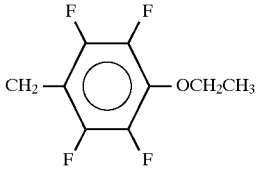 |
| 800 | H | CH₂OCH₃ | OCH₃ | CH₃ | 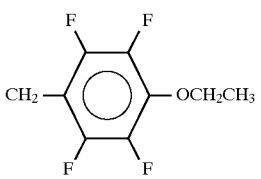 |
| 801 | H | C₂H₅ | Cl | CH₃ | 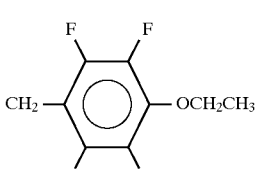 |
| 802 | H | —(CH₂)₄— | | CH₃ | 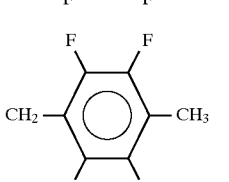 |
| 803 | H | CH₂OCH₃ | OCH₃ | CH₃ | 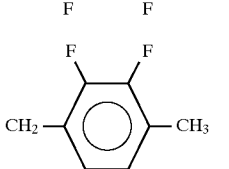 |
| 804 | H | C₂H₅ | Cl | CH₃ | 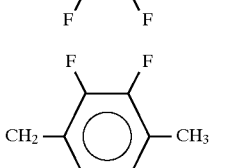 |
| 805 | H | —(CH₂)₄— | | CH₃ | 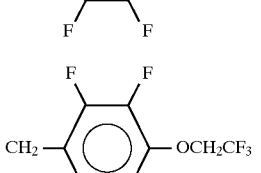 |
| 806 | H | CH₂OCH₃ | OCH₃ | CH₃ | 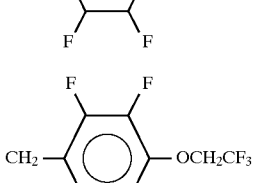 |

| | | | | | | |
|---|---|---|---|---|---|---|
| 807 | H | C₂H₅ | Cl | CH₃ | 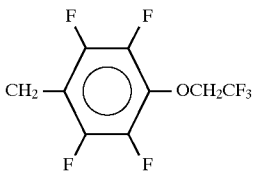 | |
| 808 | H | —(CH₂)₄— | | CH₃ | 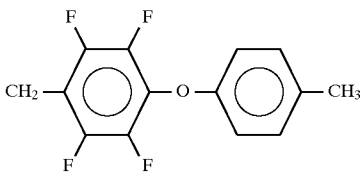 | |
| 809 | H | CH₂OCH₃ | OCH₃ | CH₃ | 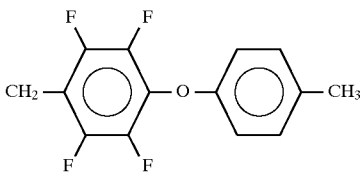 | |
| 810 | H | C₂H₅ | Cl | CH₃ | 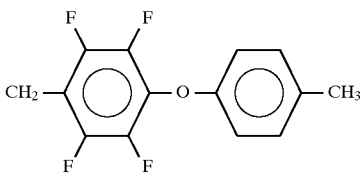 | |
| 811 | H | —(CH₂)₄— | | H | 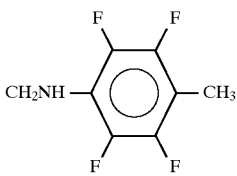 | Oil |
| 812 | H | CH₂OCH₃ | OCH₃ | H | 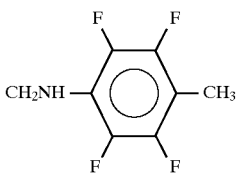 | Oil |
| 813 | H | C₂H₅ | Cl | H | 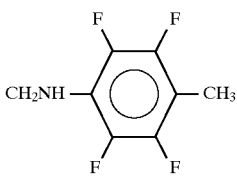 | Oil |
| 814 | H | —(CH₂)₄— | | H | 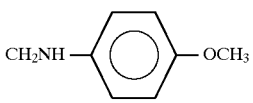 | 71–73° C. |
| 815 | H | CH₂OCH₃ | OCH₃ | H | 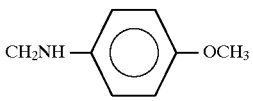 | Oil |
| 816 | H | C₂H₅ | Cl | H | 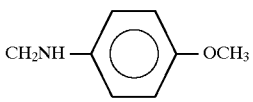 | Oil |

-continued
| Nr. | R¹ | R² | R³ | R⁴ | Q | Fp. |
|---|---|---|---|---|---|---|
| 817 | H | —(CH₂)₄— | | H |  | 142–144° C. |
| 818 | H | CH₂OCH₃ | OCH₃ | H | 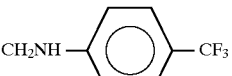 | Oil |
| 819 | H | C₂H₅ | Cl | H |  | Oil |
| 820 | H | —(CH₂)₄— | | H |  | Oil |
| 821 | H | CH₂OCH₃ | OCH₃ | H |  | Oil |
| 822 | H | C₂H₅ | Cl | H |  | Oil |
| 823 | H | —(CH₂)₄— | | H |  | 123–125° C. |
| 824 | H | CH₂OCH₃ | OCH₃ | H | 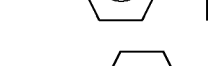 | Oil |
| 825 | H | C₂H₅ | Cl | H | 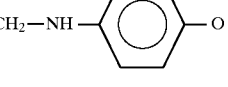 | Oil |
| Example No. | R¹ | R² | R³ | R⁴ | Q | M.p. |
|---|---|---|---|---|---|---|
| 826 | H | —(CH₂)₄— | | H | 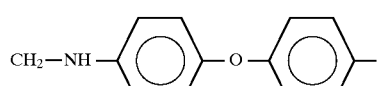 | 108–110° C. |
| 827 | H | CH₂OCH₃ | OCH₃ | H |  | Öl |
| 828 | H | C₂H₅ | Cl | H | 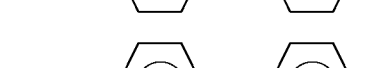 | Öl |
| 829 | H | —(CH₂)₄— | | H | 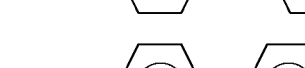 | 102° C. |

-continued

| | | | | | | |
|---|---|---|---|---|---|---|
| 830 | H | CH$_2$OCH$_3$ | OCH$_3$ | H | 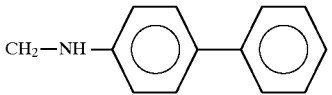 | Öl |
| 831 | H | C$_2$H$_5$ | Cl | H | 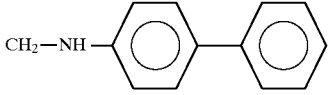 | Öl |

Table II comprises compounds of the formula

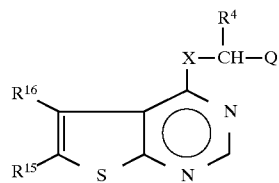

which is derived from formula I.

TABLE 2

| Example No. | R$^{15}$ | R$^{16}$ | R$^4$ | X | Q | B.p. [°C.] |
|---|---|---|---|---|---|---|
| 832 | CH$_3$ | H | H | O |  | Oil |
| 833 | C$_2$H$_5$ | H | H | O |  | Oil |
| 834 | C$_2$H$_5$ | H | H | O | 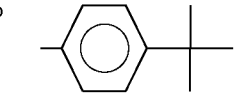 | Oil |
| 835 | CH$_3$ | CH$_3$ | H | O | 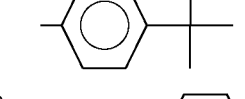 | Oil |
| 836 | C$_2$H$_5$ | H | H | O | 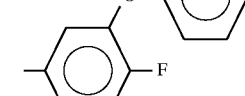 | Oil |

TABLE 2-continued

| Example No. | R$^{15}$ | R$^{16}$ | R$^4$ | X | Q | B.p. [°C.] |
|---|---|---|---|---|---|---|
| 837 | CH$_3$ | CH$_3$ | H | O | 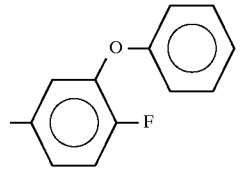 | Oil |
| 838 | CH$_3$ | H | H | O | 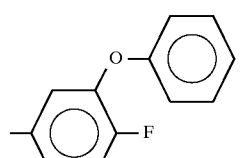 | Oil |

Table III comprises compounds of the formula

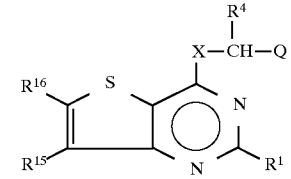

which is derived from formula I.

TABLE 3

| Example No. | R$^1$ | R$^{15}$ | R$^{16}$ | R$^4$ | X | Q | B.p. [°C.] |
|---|---|---|---|---|---|---|---|
| 839 | H | H | H | H | O | (CH$_2$)$_6$CH$_3$ | Oil |
| 840 | H | H | H | H | O |  | Oil |

TABLE 3-continued

| Example No. | R$^1$ | R$^{15}$ | R$^{16}$ | R$^4$ | X | Q | B.p. [°C.] |
|---|---|---|---|---|---|---|---|
| 841 | H | H | H | H | O | CH$_2$—⟨phenyl⟩—O—⟨phenyl⟩ | Oil |
| 842 | H | H | H | H | O | CH$_2$—⟨phenyl⟩—⟨phenyl⟩ | Oil |
| 843 | H | H | H | H | O | CH$_2$—⟨phenyl⟩—C(CH$_3$)$_3$ | Oil |

C) Biological Examples

EXAMPLE 1

Barley plants in the 3-leaf stage were severely inoculated with conidia of powdery mildew of barley (*Erysiphe graminis f.* sp. hordei) and placed in a greenhouse at 20° C. under relative atmospheric humidity of 90–95%. 24 hours after the inoculation, the plants were wetted uniformly with the compounds listed in Table IV in the active substance concentrations indicated. After an incubation time of 10 days, the plants were examined for attack by powdery mildew of barley. The disease level was expressed in % attacked leaf area relative to untreated infected control plants (=100% disease). The result is compiled in Table IV.

TABLE IV

| Compounds according to Example No. | Leaf area attacked by powdery mildew of barley in % at mg of active substance/liter spray liquor | |
|---|---|---|
| | 500 | 250 |
| 4 | 0 | 0 |
| 34 | 0 | 0 |
| 40 | 0 | 0 |
| 43 | 0 | 0 |
| 45 | 0 | 0 |
| 46 | 0 | 0 |
| 65 | 0 | 3 |
| untreated, infected plants | | 100 |

EXAMPLE 2

Wheat plants cv. "Jubilar" in the 2-leaf stage were treated to runoff point with aqueous suspensions of the preparations indicated in Table V.

After the spray coating had dried on, the plants were inoculated with an aqueous pycnospore suspension of Leptosphaeria nodorum and incubated in a controlled- environment cabinet for several hours at a relative atmospheric humidity of 100%. The plants were grown on in the greenhouse at a relative atmospheric humidity of approx. 90% until the symptoms became apparent. The disease level was expressed in % infested leaf area compared with untreated, infected control plants. The result is compiled in Table V.

TABLE V

| Compounds according to Example No. | Leaf area attacked by *Leptosphaeria nodorum* in % at mg of active substance/liter spray liquor | | |
|---|---|---|---|
| | 500 | 250 | 125 |
| 5 | 0 | 3 | 5 |
| 41 | 0 | 0 | 0 |
| 61 | 0 | 5 | — |
| 64 | 0 | 0 | 3 |
| 72 | 0 | 0 | — |
| 74 | 0 | 0 | 0 |
| 75 | 0 | 0 | 0 |
| 76 | 0 | 0 | 0 |
| 78 | 0 | 0 | 5 |
| 83 | 0 | 5 | — |
| 100 | 0 | 5 | — |
| untreated, infected plants | | 100 | |

EXAMPLE 3

Barley plants cv. "Igri" in the 2-leaf stage were treated to runoff point with an aqueous suspension of the claimed compounds.

After the spray coating had dried on, the plants were inoculated with an aqueous spore suspension of Pyrenophora teres and incubated for 16 hours in a controlled-environment cabinet at a relative atmospheric humidity of 100%. The infected plants were subsequently grown on in the greenhouse at 25° C. and 80% relative atmospheric humidity.

The disease was evaluated approx. 1 week after inoculation. The disease level was scored as % attacked leaf area compared with the untreated, infected control and can be found in Table VI.

TABLE VI

| Compounds according to Example No. | % of leaf area attacked by *Pyrenophora teres* in % at mg of active substance/liter spray liquor | | |
|---|---|---|---|
| | 500 | 250 | 125 |
| 3 | 0 | 0 | — |
| 4 | 0 | 0 | 5 |
| 5 | 0 | 0 | 0 |
| 15 | 0 | 0 | 0 |

TABLE VI-continued

| Compounds according to Example No. | % of leaf area attacked by Pyrenophora teres in % at mg of active substance/liter spray liquor | | |
|---|---|---|---|
| | 500 | 250 | 125 |
| 34 | 0 | 0 | 0 |
| 42 | 0 | 0 | — |
| 66 | 0 | 0 | 0 |
| 67 | 0 | 0 | 3 |
| 74 | 0 | 0 | 0 |
| 75 | 0 | 0 | 0 |
| 76 | 0 | 0 | 0 |
| 77 | 0 | 0 | 0 |
| 81 | 0 | 0 | 5 |
| 82 | 0 | 0 | 0 |
| 98 | 0 | 0 | 0 |
| untreated, infected plants | | 100 | |

EXAMPLE 4

Wheat cv. "Jubilar" in the 2-leaf stage was treated to runoff point with aqueous suspensions of the claimed compounds.

After the spray coating had dried on, the plants were inoculated with an aqueous spore suspension of *Puccinia recondita*. The dripping wet plants were placed for approx. 16 hours into a controlled-environment cabinet at 20° C. and a relative atmospheric humidity of approx. 100%. The infected plants were then grown on in a greenhouse at a temperature of 22°–25° C. and a relative atmospheric humidity of 50–70%.

After an incubation time of approx. 2 weeks, the fungus sporulated over the entire leaf area of the untreated control plants so that it was possible to evaluate the disease level of the test plants. The disease level was expressed in % attacked leaf area compared with untreated, infected control plants and can be found in

TABLE VII

| Compounds according to Example No. | Leaf area attacked by Puccinia recondita in % at mg of active substance/liter spray liquor | | |
|---|---|---|---|
| | 500 | 250 | 125 |
| 1 | 0 | 0 | — |
| 4 | 0 | 0 | — |
| 5 | 0 | 0 | 0 |
| 8 | 0 | 0 | — |
| 16 | 0 | 0 | — |
| 31 | 0 | 0 | — |
| 61 | 0 | 0 | 5 |
| 63 | 0 | 5 | 10 |
| 64 | 0 | — | — |
| 65 | 0 | 0 | 0 |
| 77 | 0 | 0 | — |
| 78 | 0 | 0 | — |
| 99 | 0 | 0 | — |

EXAMPLE 5

Bean plants (*Phaseolus v.*) which were heavily infested with the two-spotted spider mite (*Tetranychus urticae*, full population) were sprayed with the aqueous dilution of a wettable powder concentrate which contained 250 ppm of the active substance in question. The mortality of the mites was checked after 7 days. A mortality of 100% was achieved with the compounds according to Example 4, 5, 14, 23, 42, 43, 46, 47, 49, 50, 51, 65, 69, 73, 74, 75, 82, 90, 92, 95, 100, 102 and 840.

EXAMPLE 6

Field beans (*Vicia faba*) which were heavily infested with the black bean aphid (*Aphis fabae*) were sprayed to beginning runoff point with aqueous dilutions of wettable powder concentrates containing 250 ppm of active substance. The mortality of the aphids was determined after 3 days. Using the compounds according to Example 4, 5, 42, 46, 49, 65, 66, 73, 74, 75, 77, 87 and 102, it was possible to achieve a mortality of 100%.

EXAMPLE 7

On the inside of the lid and the bottom of a Petri dish, in each case 1 ml of the formulation to be tested was emulsified and applied uniformly in water, and, after the coating had dried on, in each case 10 imagines of the common housefly (*Musca domestics*) were introduced. The dishes were sealed and then stored at room temperature, and the mortality of the test animals was determined after 3 hours. At 250 ppm (based on active substance content), a good action (100% mortality) against the common housefly was shown by preparations 4, 15, 16, 46, 49, 59, 63, 72, 73, 77, 78, 79, 98, 99 and 841.

EXAMPLE 8

Filter paper disks on which eggs of the large milkweed bug (*Oncopeltus fasciatus*) were placed, were treated with in each case 0.5 ml of aqueous dilution of the formulation to be tested. After the coating had dried on, the Petri dish was sealed, and the atmospheric humidity inside was kept at a maximum. The dishes were kept at room temperature, and the ovicidal action was determined after 7 days. Using an active substance content of 250 ppm, a 100% mortality was achieved with the compounds according to Example 1, 2, 4, 5, 14, 15, 16, 30, 33, 34, 35, 40, 41, 43, 45 to 50, 53, 58, 59, 61, 64, 65, 66, 72, 73, 74, 76, 77, 83, 84, 87, 89, 90, 95, 102, 839 and 841.

We claim:

1. A substituted 4-alkoxypyrimidine of the formula I

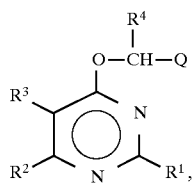

in which

R$^1$ is hydrogen, halogen, (C$_1$–C$_4$)alkyl or (C$_3$–C$_6$)cycloalkyl,

R$^2$ is methoxymethyl,

R$^3$ is methoxy

R$^4$ is hydrogen, (C$_1$–C$_4$)alkyl, (C$_3$–C$_6$)cycloalkyl or (C$_1$–C$_4$)haloalkyl, Q has the meaning of Q$^1$ and Q$^1$ is (C$_1$–C$_{15}$) unbranched or branched hydrocarbon and which is optionally substituted by one, two or three halogen atoms, a (C$_1$–C$_{15}$)alkoxy-(C$_1$–C$_{15}$)alkoxy group, a (C$_1$–C$_{15}$)alkylthio group, a (C$_1$–C$_{15}$)alkylsulfinyl group, a (C$_1$–C$_{15}$)alkylsulfonyl group, a (C$_1$–C$_{15}$)alkanoyl group, a (C$_4$–C$_8$)cycloalkylalkoxy group, a (C$_4$–C$_8$)cycloalkylalkylthio group, a benzyloxy or a phenoxybenzyloxy group, or Q has the meaning of Q$^2$ and $Q^2$ is a group of the formula IIa–IIj

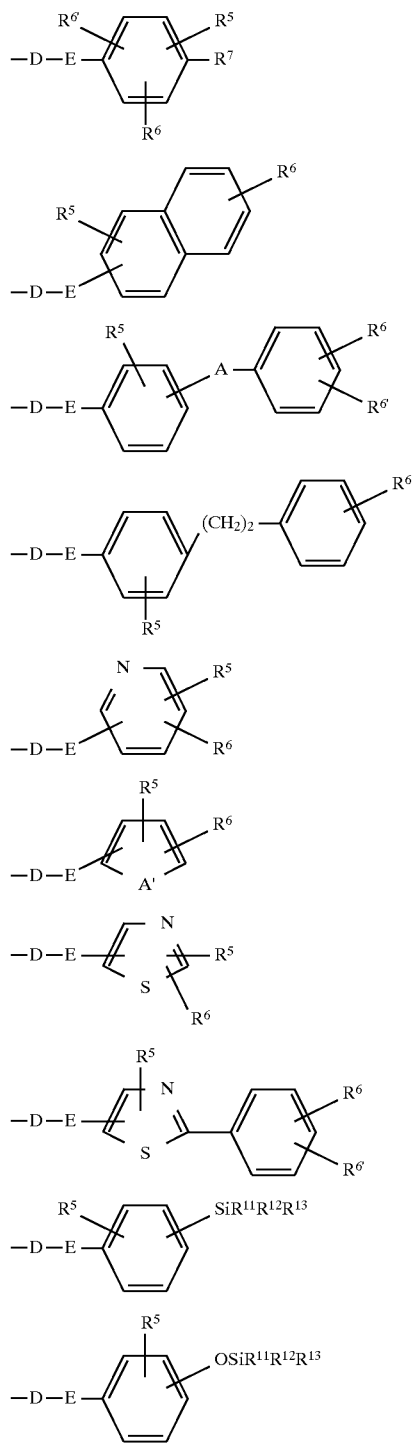

in which
A is oxygen, —O—CH$_2$—, sulfur, sulfinyl or sulfonyl,
A' is oxygen or sulfur,
D is a (C$_1$–C$_6$)alkylene group,
E is a direct bond,
R$^5$, R$^6$ and R$^{6'}$ are identical or different and are in each case hydrogen, halogen, (C$_1$–C$_8$)alkyl, (C$_2$–C$_8$)alkenyl, (C$_2$–C$_8$)alkynyl, (C$_3$–C$_6$)cycloalkyl, (C$_1$–C$_8$)haloalkyl, (C$_1$–C$_8$)alkoxy, (C$_1$–C$_8$)alkylthio, (C$_1$–C$_8$) alkylsulfinyl, (C$_1$–C$_8$)alkylsulfonyl, (C$_1$–C$_4$) dialkylamino or nitro, R$^7$ is halogen, (C$_1$–C$_8$)alkyl, (C$_2$–C$_8$)alkenyl, (C$_2$–C$_8$) alkynyl, (C$_3$–C$_6$)cycloalkyl, (C$_1$–C$_8$)haloalkyl, (C$_1$–C$_8$)alkoxy, (C$_1$–C$_8$)alkylthio, (C$_1$–C$_8$) alkylsulfinyl, (C$_1$–C$_8$)alkylsulfonyl, (C$_1$–C$_4$) dialkylamino, nitro, (C$_1$–C$_4$)alkoxy-(C$_1$–C$_4$)alkyl, (C$_1$–C$_4$)alkoxycarbonyl, (C$_1$–C$_8$)alkanoyl or a group of the formula III

in which X and Y are identical or different and are in each case sulfur or oxygen and R$^8$ is hydrogen or (C$_1$–C$_4$)alkyl, or Q has the meaning of Q$^3$ and Q$^3$, is a group of the formula IV

in which R$^5$ and R$^6$ have the abovementioned meanings,

U is a direct bond, sulfur, sulfinyl, sulfonyl or methylene,

R$^9$ is phenyl or a heterocyclic radical, where each of the two abovementioned radicals can be unsubstituted or substituted with one or two substituents and these substituents are identical or different and are in each case halogen, (C$_1$–C$_4$)alkyl, trifluoromethyl, nitro, (C$_1$–C$_4$)alkoxy, (C$_1$–C$_4$)alkylthio, (C$_1$–C$_4$) alkylsulfinyl, (C$_1$–C$_4$)alkylsulfonyl, (C$_1$–C$_4$)alkoxy-(C$_1$–C$_4$)alkyl, phenyl, phenoxy, (C$_1$–C$_4$) alkoxyphenoxy, halophenoxy or (C$_1$–C$_4$)alkylphenoxy, or U is oxygen and R$^9$ is as defined above or is (C$_1$–C$_4$) haloalkyl or a group of the formula V

in which

W is nitrogen or a group CR$^{10}$ in which

R$^{10}$ is hydrogen, fluorine, cyano, formyl, acetyl, nitro, methyl, methoxy or 1,3-dioxolan-2-yl, R$^{11}$, R$^{12}$ and R$^{13}$ are identical or different and ar (C$_1$–C$_{15}$) alkyl which is optionally monosubstituted or polysubstituted by halogen, or is

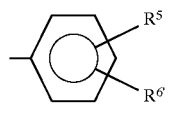

or

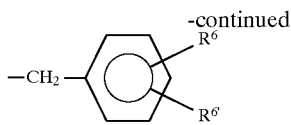

-continued in which $R^6$ and $R^{6'}$ are as defined above, and the salts and stereoisomers thereof.

2. A compound as claimed in claim 1, wherein, in formula I,
   $R^1$ is hydrogen, chlorine or methyl,
   $R^4$ is hydrogen, methyl, ethyl, trifluoromethyl or cyclopropyl.

3. A compound as claimed in claim 1, wherein, in formula I,
   $R^1$ is hydrogen or methyl,
   $R^4$ is hydrogen, methyl, ethyl, trifluoromethyl or cyclopropyl.

4. A compound as claimed in claim 1, wherein, in formula I,
   $R^1$ is hydrogen,
   $R^4$ is hydrogen, methyl or ethyl.

5. A compound as claimed in claim 1, wherein, in formula I,
   $R^1$ is hydrogen,
   $R^4$ is hydrogen, methyl or ethyl.

6. A compound as claimed in claim 1, wherein, in formula I,
   $R^1$ is hydrogen,
   $R^4$ is hydrogen or methyl,
   $Q^1$ is a $(C_4-C_{10})$alkyl group or a $(C_1-C_3)$alkyl group which is substituted by a $(C_4-C_8)$cycloalkylalkoxy group or a $(C_4-C_8)$cycloalkylalkylthio group.

7. A compound as claimed in claim 1, wherein, in formula I,
   $R^1$ is hydrogen,
   $R^4$ is hydrogen or methyl,
   $Q^2$ is a group of the formulae IIa–IIj, in which D is a methylene group and E is a direct bond, $R^5$, $R^6$ and $R^{6'}$ are hydrogen, $(C_1-C_8)$alkyl, $(C_1-C_4)$alkoxy, cyclohexyl or trifluoromethyl, and
   $R^7$ is methoxyethyl or ethoxyethyl.

8. A compound as claimed in claim 1, wherein, in formula I,
   $R^1$ is hydrogen,
   $R^4$ is methyl, ethyl or cyclopropyl,
   Q has the meaning of $Q^3$,
   $R^5$ and $R^6$ are hydrogen,
   U is oxygen,
   $R^9$ is phenyl or heterocycle, which are optionally substituted with one or two substituents and these substituents are identical or different and are halogen, $(C_1-C_4)$alkyl, trifluoromethyl, nitro, $(C_1-C_4)$alkoxy, $(C_1-C_4)$alkylthio or $(C_1-C_4)$alkoxy-$(C_1-C_4)$alkyl.

9. An insecticidal or acaricidal agent which comprises an effective amount of a compound of the formula I as claimed in claim 1.

10. A fungicidal agent which comprises an effective amount of a compound of the formula I as claimed in claim 1.

11. A nematocidal agent which comprises an effective amount of a compound of the formula I as claimed in claim 1.

12. A method for controlling insect pests and acarids, which comprises applying an effective amount of a compound of the formula I as claimed in claim 1 to these insect pests and acarids or to the plants, areas or substrates infested with them.

13. A method for controlling fungal pests, which comprises applying an effective amount of a compound of the formula I as claimed in claim 1 to these fungal pests or to the plants, areas or substrates attacked by them.

14. A method for controlling nematodes, which comprises applying an effective amount of a compound of the formula I as claimed in claim 1 to these nematodes or to the plants, areas or substrates infested with them.

* * * * *